(12) United States Patent
Dichtel et al.

(10) Patent No.: US 11,965,068 B2
(45) Date of Patent: Apr. 23, 2024

(54) CROSS-LINKED POLYMER NETWORKS AND METHODS OF MAKING AND USING SAME

(71) Applicant: Cornell University, Ithaca, NY (US)

(72) Inventors: William R. Dichtel, Wilmette, IL (US); Deepti Gopalakrishnan, Ithaca, NY (US)

(73) Assignee: Cornell University, Ithaca, NY (US)

( * ) Notice: Subject to any disclaimer, the term of this patent is extended or adjusted under 35 U.S.C. 154(b) by 637 days.

(21) Appl. No.: 16/998,987

(22) Filed: Aug. 20, 2020

(65) Prior Publication Data

US 2020/0377679 A1 Dec. 3, 2020

Related U.S. Application Data

(63) Continuation of application No. 14/770,234, filed as application No. PCT/US2014/019437 on Feb. 28, 2014, now Pat. No. 10,787,551.

(60) Provisional application No. 61/770,482, filed on Feb. 28, 2013.

(51) Int. Cl.
| | |
|---|---|
| C08J 5/00 | (2006.01) |
| C08J 5/18 | (2006.01) |
| C09K 11/06 | (2006.01) |
| G01N 21/64 | (2006.01) |
| G01N 33/00 | (2006.01) |

(52) U.S. Cl.
CPC .......... *C08J 5/18* (2013.01); *C09K 11/06* (2013.01); *G01N 21/6428* (2013.01); *G01N 33/0057* (2013.01); *C08J 2325/08* (2013.01); *C09K 2211/1425* (2013.01); *C09K 2211/1466* (2013.01); *G01N 2021/6432* (2013.01)

(58) Field of Classification Search
CPC .......................................................... C08J 5/18
USPC ............................................................. 436/98
See application file for complete search history.

(56) References Cited

U.S. PATENT DOCUMENTS

| | | |
|---|---|---|
| 2001/0037681 A1 | 11/2001 | Shibue et al. |
| 2004/0116650 A1 | 6/2004 | Swager et al. |
| 2007/0111321 A1 | 5/2007 | Deans et al. |
| 2008/0145660 A1 | 6/2008 | Wang et al. |
| 2009/0246881 A1 | 1/2009 | Toal et al. |

OTHER PUBLICATIONS

Sun, L., et al., Luminescent microporous organic polymers containing 1,3,5-tri(4-ethenylphenly)benzene unit constructed by Heck coupling reaction, Polymer Chemistry, 2013, vol. 4, pp. 1932-1938.
Xu, Y., Conjugated Microporous Polymers (CMPs) in 2013, JOurnal Meeting @ Jiang Group, Jan. 24, 2014, 49 pages.
(Continued)

*Primary Examiner* — Christine T Mui
*Assistant Examiner* — Emily R. Berkeley
(74) *Attorney, Agent, or Firm* — Hodgson Russ LLP

(57) ABSTRACT

Cross-linked polymer networks that are at least partially conjugated (e.g., phenylene vinylene polymer networks). The cross-linked polymer networks may be thin-films disposed on a substrate. The cross-linked polymer network may be covalently bonded to the substrate. The cross-linked polymer networks can be used, for example, in methods of detecting explosives (e.g., RDX (cyclotrimethylenetrinitramine)) and degradation products thereof.

30 Claims, 36 Drawing Sheets

(56) References Cited

OTHER PUBLICATIONS

Shin, R., et al., Electron-Accepting Conjugated Materials Based on 2-Vinyl-4,5-dicyanoimidazoles for Application in Organic Electronics, J. Org. Chem., 2009, vol. 74, pp. 3293-3298.

Lupton, J.M., et al., Exciton confinement in organic dendrimer quantum wells for opto-electronic applications, The Journal of Chemical Physics, Jan. 8, 2002, vol. 116, No. 2, pp. 455-459.

CROSS-LINKED POLYMER NETWORKS AND METHODS OF MAKING AND USING SAME

CROSS-REFERENCE TO RELATED APPLICATIONS

This application is a continuation of U.S. patent application Ser. No. 14/770,234, filed Aug. 25, 2015, which is a National Phase of International application no. PCT/US2014/019437, filed Feb. 28, 2014, which claims priority to U.S. provisional patent application No. 61/770,482, filed Feb. 28, 2013, the disclosures of each of which are incorporated herein by reference.

STATEMENT REGARDING FEDERALLY SPONSORED RESEARCH

This invention was made with government support under contract no. CHE-1056657 awarded by the National Science Foundation. The government has certain rights in the invention.

FIELD OF THE DISCLOSURE

The present disclosure generally relates to conjugated cross-linked polymer networks. More particularly, the present disclosure relates to arylene vinylene cross-linked polymer networks.

BACKGROUND OF THE DISCLOSURE

Low-volatility explosives such as 1,3,5-trinitro-1,3,5-triazine (RDX), 1,3,5-trinitrotoluene (TNT) and pentaerythritol tetranitrate (PETN) pose major security risks and safety hazards throughout the world. RDX in particular is one of the most common components of plastic explosives and has been used in recent terrorist activities. The detection of trace amounts of these compounds, ideally from the vapor phase, is essential for identifying explosive devices and individuals who handle explosive devices. Vapor detection of 1,3-dinitrotoluene (DNT) and TNT has been studied extensively for the last two decades, resulting in several technologically relevant solutions. However, detecting RDX vapor remains an important and difficult challenge, as it is three orders of magnitude less volatile than TNT and is a weaker electron acceptor than nitroaromatic explosives.

Analytical techniques that have been applied for trace RDX sensing include colorimetric immunoassays, surface enhanced Raman spectroscopy, ion mobility spectroscopy, and changes in the surface plasmon resonance of Au nanoparticles. Many of these techniques require specialized equipment and/or require preconcentration strategies. It was previously reported that dihydroacridine derivatives show a "turn-on" fluorescence response to nitration induced by the photodegradation of RDX and PETN. This strategy demonstrated 100 pg sensitivity to RDX, similar to current swab-based transportation security systems. However, we are unaware of colorimetric or fluorescent chemical systems capable of direct RDX vapor detection.

Fluorescence quenching of conjugated polymers by appropriate analytes is a highly sensitive phenomenon that enables the direct detection of explosive vapors. In addition to its high sensitivity, the simplicity of photoemission measurements facilitates the design of stand-off detection devices. Many conjugated polymers fluoresce intensely upon exposure to visible light. Following light absorption, excited states, or excitons, diffuse along and among polymer chains, where they may encounter the analyte of interest. The analyte non-radiatively deactivates the mobile excitons, interrupting the fluorescence of the material. Since excitons sample many polymer chains during their lifetimes, a small amount of the analyte quenches the fluorescence of many polymer chains; this amplification strategy provides the high sensitivity necessary for vapor phase detection. The most sensitive conjugated polymers sense TNT at parts per quadrillion levels, and these materials have been commercialized for military and security use. Recently developed material classes with high surface area to interact with analytes, including metal organic frameworks (MOFs), conjugated microporous polymers, and self-assembled π-electron systems have shown promise for detecting energetic compounds. However, most of these materials respond to TNT or more volatile nitroaromatics; none of these materials have demonstrated a response to RDX.

BRIEF SUMMARY OF THE DISCLOSURE

In an aspect, the present disclosure provides cross-linked polymer networks. The networks can be formed by polymerizing a monomer or monomers, in which at least one monomer has 3 or more polymerizable groups. For example, the monomers are polymerized using a olefin metathesis catalyst (e.g., a Grubbs $2^{nd}$ generation olefin metathesis catalyst). Examples of suitable cross-linked polymer networks include cross-linked arylene vinylene-linked polymer networks, such as phenylene vinylene-linked polymer networks (e.g., trisphenylene vinylene-linked polymer networks).

The cross-linked polymer network may be present as a thin film on a substrate. The polymer thin films are amorphous. The cross-linked polymer network may be covalently bound to a substrate.

In an aspect, the present disclosure provides a method of making cross-linked polymer networks. In an embodiment, the method of making cross-linked polymer networks comprises the steps of contacting one or more monomers and catalyst (e.g., a Grubbs $2^{nd}$ generation olefin metathesis catalyst) such that a cross-linked polymer network is formed. Optionally, one or more monomers and catalyst are contacted in the presence of a substrate (e.g., an alkene functionalized substrate). The one or more monomers and catalyst may be contacted in a solvent.

The presence of a substrate in the reaction mixture comprising the monomer and catalyst results in formation of an amorphous thin-film of a cross-linked polymer network that is disposed on a substrate. The substrate may be an alkene functionalized substrate. The presence of an alkene functionalized substrate in the reaction results in a thin-film of a cross-linked polymer network disposed on a substrate where the cross-linked polymer network is covalently bound to the substrate.

In an aspect, the present disclosure provides methods for detecting explosive compounds using the cross-linked polymer networks. The methods are based on fluorescence quenching of such polymer networks by the explosives. The explosives (or degradation products of the explosives) can be detected at least at low ng levels (e.g., 1 ng) and without pre-concentration of the test sample.

In an embodiment, the method for detecting explosives in a test sample comprises the steps of contacting the cross-linked polymer network with a test sample and determining a change (e.g., a decrease) in fluorescence emitted from the cross-linked polymer network, wherein the change (e.g., a decrease) in fluorescence correlates to the amount of explosive present in the sample. In another embodiment, the method for detecting explosives comprises the steps of a)rcontacting a test sample with a cross-linked polymer network comprising a plurality of cross-linked trivinyl benzene moieties (e.g., a plurality of cross-linked trivinyl benzene moieties covalently bonded to a fully conjugated core); b) measuring the fluorescence of the cross-linked polymer network, where a change (e.g., a decrease) in the fluorescence of the cross-linked polymer network in the presence of the test sample is indicative of the presence of the explosive in the sample. In yet another embodiment, where a change (e.g., a decrease) in the fluorescence of the cross-linked polymer network in the presence of the test sample relative to the fluorescence of the cross-linked polymer network in the absence of the test sample is indicative of the presence of the explosive in the test sample. In yet another embodiment, where no significant change in the fluorescence of the cross-linked polymer network in the presence of the test sample relative to the fluorescence of the cross-linked polymer network in the absence of the test sample is indicative of the absence of the explosive in the test sample.

The cross-linked polymer networks may be present as thin films disposed on a substrate as described herein. For example, the cross-linked polymer network is covalently bonded to the substrate.

A wide variety of samples can be used. For example, the sample can be a vapor. The vapor can be the headspace above a liquid or solid sample (such as a swab used in airport screening). The sample comprises an explosive compound (e.g., nitramines (such as Research Department Explosive (RDX) (i.e., cyclotrimethylenetrinitramine)) and nitroesters (such as pentaerythritol tetranitrate (PETN), trinitrotoluene (TNT), dinitrotoluene (DNT), 2,4,6-triamino-1,3,5-trinitrobenzene (TATB), 2,3-dimethyl-2,3-dinitrobutane (DMNB), and octahydro-1,3,5,7-tetranitro-1,3,5,7-tetrazocine (HMX)), a degradation product thereof (e.g., photodegradation product), or a combination thereof.

The explosive compound and/or degradation product may be detected at attogram amounts or less. The presence of an explosive compound and/or degradation product can be detected at from 1 nanogram to 1 attogram, including all values and ranges therebetween. The explosive compound or degradation product can be detected in the presence of other commonly present volatile compounds. The sample may not be pre-concentrated.

DETAILED DESCRIPTION OF THE DISCLOSURE

Figure 1:
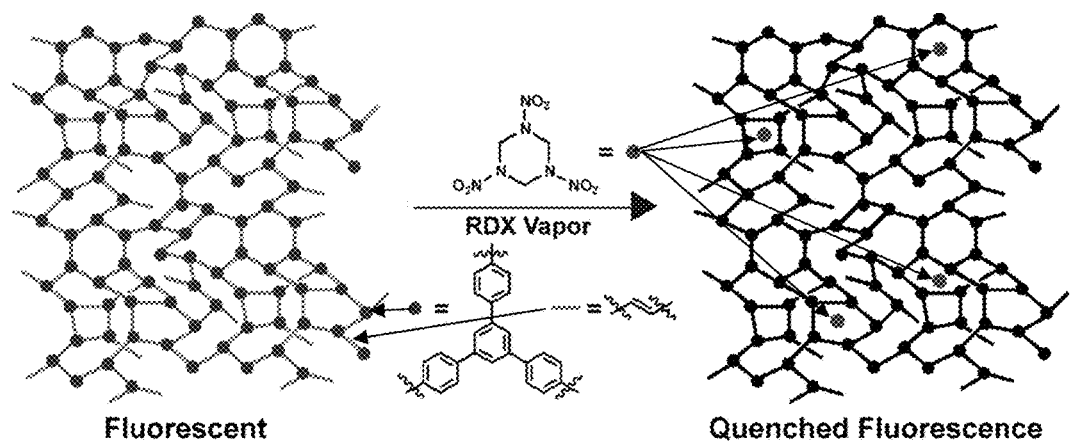
FIG. 1. An example of a schematic of RDX vapor detection by a trisphenylene vinylene (TPV) conjugated polymer network.

The present disclosure provides cross-linked polymer networks. Also provided are methods of making and using the cross-linked polymer networks. For example, the cross-linked polymer networks are used in methods of detecting explosives.

In an aspect, the present disclosure provides cross-linked polymer networks. The polymer networks are at least partially conjugated. The networks can be formed by polymerizing a monomer or monomers, in which at least one monomer has 3 or more polymerizable groups. For example, the polymerizable group(s) is/are an olefin having E or Z geometry. The monomer has a conjugated core. The monomers may be fully conjugated. The monomer may have one or more heterocycles. Examples of suitable monomers include porphyrins, trivinyl benzenes, carbazoles, thiophenes, pyridines, benzothiadiazoles, dialkoxybenzenes, diaminobenzenes, quinones, and fused acenes. The degree of reaction (i.e., how many of the polymerizable groups have reacted) is dependent on factors such as reaction time.

The monomers can be polymerized using methods known in the art. In an embodiment, the monomers are polymerized using a olefin metathesis catalyst (e.g., a Grubbs 2$^{nd}$ generation olefin metathesis catalyst).

Examples of suitable cross-linked polymer networks include cross-linked arylene vinylene-linked polymer networks, such as phenylene vinylene-linked polymer networks (e.g., trisphenylene vinylene-linked polymer networks). In an embodiment, the cross-linked polymer network comprises a plurality of cross-linked trivinyl benzene moieties (e.g., a plurality of cross-linked trivinyl benzene moieties covalently bonded to a fully conjugated core). For example, the core is an aryl moiety such as a benzene moiety. For example, a trisphenylene vinylene-linked polymer network is formed using trivinyl benzene monomers having the following general structure:

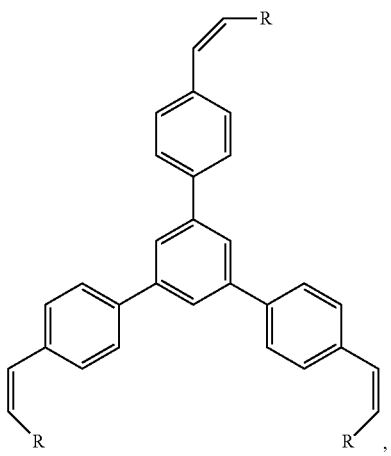

where the R groups independently at each occurrence in the monomer are selected from hydrogen, C1 to C15 aliphatic groups (which may be linear or branched and/or substituted or unsubstituted), or aromatic groups or silicon protecting groups (such as trimethylsilyl (TMS), triethylsilyl (TES), tert-butyldimethylsilyl (TBS), or tert-butyldiphenylsilyl (TBDPS)). One or more of the aromatic rings may be substituted. One or more of the phenyl rings may be heterocyclic aromatic rings (e.g., N-containing rings). The R groups may be those known in the art to facilitate olefin metathesis reactions. While the olefin geometry is depicted as Z, it may be E or Z.

The degree of reaction of the monomers is the ratio of the number of polymerizable groups (e.g., the number of alkenes that have reacted with an alkene on another monomer) that have reacted in cross-linked polymer network to the number of polymerizable groups (e.g., the number of alkenes that have reacted with an alkene on another monomer) that are available to so react in the cross-linked polymer network. For example, the degree of reaction of cross-linked polymer network formed from a monomer having three polymerizable groups is 33% to 100%, including all integer % values and ranges therebetween. The extent of reaction can be determined by, for example, ultraviolet spectroscopy or infrared spectroscopy.

The cross-linked polymer network may be present as a thin film on a substrate. Accordingly, in an embodiment the present disclosure provides a thin film of a cross-linked polymer network (e.g., comprising a plurality of trivinyl benzene moieties) disposed on a substrate as described herein.

The cross-linked polymer thin films are amorphous. In an embodiment, the cross-linked polymer network is disposed on a substrate. The polymer network thin film can have a thickness of 2 nm to 10 microns, including all integer nm values and ranges therebetween.

For example, the cross-linked polymer network is present as a thin film disposed on a substrate such as fused silica, silicon, gold, silver, platinum, copper, nickel, glass, sapphire, mica, or plastic (e.g., polymer) substrates. The substrates may be transparent. It is desirable that the substrate have greater than 80% transmittance for wavelengths of 225 nm to 800 nm. The substrate can be planar (a square or disc) or non-planar (e.g., a capillary).

The cross-linked polymer network may be covalently bound to a substrate. In an embodiment, the cross-linked polymer network is bound to the substrate by a plurality of covalent bonds between the network and substrate. The cross-linked polymer network is covalently bound to the substrate (e.g., silica substrate) via a linker group. In an embodiment, the linker group is an alkyl group. For example, the cross-linked polymer network is be bound to a substrate by an alkyl linker group. The alkyl linker group may be a C1 to C15 aliphatic group (which may be linear or branched and/or substituted or unsubstituted). In another embodiment, the linker group comprises one or more alkyl moieties and one or more a 5 or 6 member aromatic ring moiety. The polymerizable moiety is covalently bonded to the alkyl moiety or aromatic ring moiety. The alkyl moiety may be a C1 to C15, including all integer number of carbons and ranges therebetween, aliphatic group (which may be linear or branched and/or substituted or unsubstituted).

In an aspect, the present disclosure provides a method of making cross-linked polymer networks. In an embodiment, the cross-linked polymer network is made by a method of the present disclosure.

In an embodiment, the method of making cross-linked polymer networks comprises the steps of contacting one or more monomers (e.g., one, two, or three different monomers) and catalyst such that a cross-linked polymer network is formed. Optionally, one or more monomers and catalyst are contacted in the presence of a substrate (e.g., an alkene functionalized substrate).

The monomer has a conjugated core. The monomers may be fully conjugated. The monomers have 2 or more polymerizable groups. At least one monomer has 3 or more polymerizable groups. For example, the polymerizable group(s) is/are an olefin having E or Z geometry. The monomer may have one or more heterocycles. Examples of suitable monomers include porphyrins, trivinyl benzenes, carbazoles, thiophenes, pyridines, benzothiadiazoles, dialkoxybenzenes, diaminobenzenes, quinones, and fused acenes.

In an embodiment, the monomer comprises a plurality of cross-linked trivinyl benzene moieties covalently bonded to a fully conjugated core. For example, the core is an aryl moiety such as a benzene moiety.

For example, a monomer is a trivinyl benzene monomer having the following general structure:

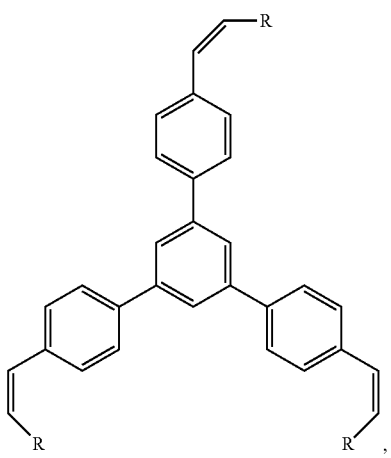

where the R groups independently at each occurrence in the monomer are selected from hydrogen, C1 to C15 aliphatic groups (which may be linear or branched and/or substituted or unsubstituted), or aromatic groups. The R groups can be silicon protecting groups such as trimethylsilyl (TMS), triethylsilyl (TES), tert-butyldimethylsilyl (TBS), or tert-butyldiphenylsilyl (TBDPS). One or more of the aromatic rings can be substituted. One or more of the phenyl rings can be heterocyclic aromatic rings (e.g., N-containing rings). The R groups can be those known in the art to facilitate olefin metathesis reactions. While the olefin geometry is depicted as Z, it can be E or Z. These monomers can be used to form trisphenylene vinylene-linked polymer networks.

The one or more monomers and catalyst may be contacted in a solvent. Examples of suitable solvents include chlorinated solvents (e.g., methylene chloride), 1,2-dichlorobenzene, 1,2,4-trichlorobenzene, 1,2-dichloroethane, 1,1,2,2-tetrachloroethane, 1,1,2-trichloroethane, carbon tetrachloride, chloroform, trichloroethylene, 1,1,1-trichloroethane, 1,2,3-trichloropropane, and 1,2-ichloropropane. Mixtures of solvents may be used. The solvent may comprise a co-solvent. Examples of suitable co-solvents include organic solvents such as ethers, alkanes, and alcohols.

The catalyst is any catalyst that catalyzes a reaction between a first alkene moiety on a monomer and a second alkene moiety on a different monomer (i.e., olefin metathesis). In an embodiment, the catalyst catalyzes a plurality of reactions between alkene moieties on different monomers. In an embodiment, the catalyst is an olefin metathesis catalyst. Examples of suitable olefin metathesis catalysts include ruthenium alkylidene catalysts (e.g., Grubbs 2nd generation olefin metathesis catalysts). The catalyst can be present at 0.01 mol % to 20 mol %, including all mol % values to the 0.01 and ranges therebetween.

The one or more monomers and catalyst are contacted such that a cross-linked polymer network is formed. For example, the monomer(s) and catalyst are contacted under solvothermal conditions. The one or more monomers and catalyst can be contacted for a selected time and temperature. In an embodiment, the monomer(s) and catalyst are contacted, for example, for 1 hour to 72 hours at a temperature of 0° C. to 120° C., including all integer hour values and ranges therebetween and all integer ° C. values and ranges therebetween and all combinations of such hours and temperatures. The monomer(s) and catalyst are contacted, for example, for 1 hour to 72 hours at a temperature of 0° C. to 120° C. or for 10 hours to 80 hours at a temperature of 45° C. Generally, longer contact times and/or higher temperatures provide cross-linked polymer networks having a higher degree of conjugation (e.g., a larger fraction of the alkenes on a monomer have reacted with an alkene on another monomer).

The reaction (i.e., contacting one or more monomers and catalyst) may be carried out under an inert atmosphere. For example, the reaction is carried out under a nitrogen or argon atmosphere.

The presence of a substrate in the reaction mixture comprising the monomer and catalyst results in formation of an amorphous thin-film of a cross-linked polymer network that is disposed on a substrate. The substrates can be as described herein.

The substrate may be a functionalized substrate (e.g., an alkene functionalized substrate). The functionalized substrate has a plurality of polymerizable groups (e.g., alkene moieties) that can react with a polymerizable group (e.g., alkene moieties) of the monomer and/or cross-linked polymer network. For example, the functionalized substrate is an alkene functionalized substrate. In an embodiment, the functionalized substrate provides a plurality of free alkene moieties for covalently binding to the growing cross-linked polymer (e.g., TPV polymer) during the above reaction conditions. The presence of a functionalized substrate in the reaction results in a thin-film of a cross-linked polymer network disposed on a substrate where the cross-linked polymer network is covalently bound to the substrate. In an embodiment, the cross-linked polymer network is bound to the substrate by a plurality of covalent bonds between the network and substrate.

The alkene functionalized substrates have a plurality of alkene moieties covalently bonded to the substrate. The alkene moiety is covalently bonded to the substrate via a linker group that is covalently bonded to the substrate and alkene moiety. Examples of suitable alkene functionalized substrates include substrates such as silica substrates functionalized with an allyl trialkoxy silane or alkenyl trialkoxy silane. The alkenyl trialkoxy silane has an alkenyl moiety (which may be linear or branched and/or substituted or unsubstituted) having a carbon-carbon double bond. The carbon-carbon bond may be a terminal carbon-carbon bond or an internal carbon-carbon double bond. The alkenyl moiety has 3 to 15 carbons, including all integer number of carbons and ranges therebetween. In an embodiment, the allyl trialkoxy silane is allyltrimethoxy silane.

The steps of the methods of making the cross-linked polymer networks described in the various embodiments and examples disclosed herein are sufficient to carry out the methods. Thus, in an embodiment, the method consists essentially of a combination of the steps of the methods disclosed herein. In another embodiment, the method consists of such steps.

In an aspect, the present disclosure provides methods for detecting explosive compounds (or degradation products of the explosives) using the cross-linked polymer networks. The methods are based on, for example, fluorescence quenching of such polymer networks by the explosives (or degradation products of the explosives). The change (e.g., decrease) in the fluorescence of the cross-linked polymer network is indicative of the presence of the explosives (or degradation products of the explosives). In an embodiment, the change (e.g., decrease) in the fluorescence of the cross-linked polymer network correlates (e.g., linearly or non-linearly) with the amount of explosives (or degradation products of the explosives) present in the test sample. The explosives (or degradation products of the explosives) can be detected at least at low ng levels (e.g., 1 ng) and without pre-concentration of the sample. In an embodiment, the sample is not subjected to a pre-concentration step. The cross-linked polymer networks may be present as thin films disposed on a substrate as described herein.

In an embodiment, the method for detecting explosives (or degradation product(s) of the explosives) in a test sample comprises the steps of contacting the contacting the cross-linked polymer network with a test sample (that may or may not comprise an explosive or degradation product thereof), and determining the change (e.g., decrease) in fluorescence emitted from the cross-linked polymer network, wherein the change (e.g., decrease) in fluorescence is indicative of (e.g., correlates linearly or non-linearly to) the amount of explosive (or degradation product(s) of the explosives) present in the test sample.

In another embodiment, the method for detecting explosives comprises the steps of a) contacting a test sample (that may or may not comprise an explosive or degradation product thereof) with a cross-linked polymer network comprising a plurality of cross-linked trivinyl benzene moieties (e.g., a plurality of cross-linked trivinyl benzene moieties covalently bonded to a fully conjugated core (e.g., an aryl moiety such as a benzene moiety)); b) measuring the fluorescence of the cross-linked polymer network, where a change (e.g. decrease) in the fluorescence of the cross-linked polymer network in the presence of the test sample is indicative of (e.g. correlates linearly or non-linearly with) the presence of the explosive (or degradation product(s) of the explosives) in the sample. In yet another embodiment, where a decrease in the fluorescence of the cross-linked polymer network in the presence of the test sample relative to the fluorescence of the cross-linked polymer network in the absence of the test sample (or in the presence of a reference sample) is indicative of (e.g., correlates linearly or non-linearly with) the presence of the explosive (or degradation product(s) of the explosives) in the test sample. In yet another embodiment, no significant change in the fluorescence of the cross-linked polymer network in the presence of the test sample relative to the fluorescence of the cross-linked polymer network the absence of the test sample (or in the presence of a reference sample) is indicative of (e.g., correlates linearly or non-linearly with) the absence of the explosive (or degradation product(s) of the explosives) in the test sample.

The lack of a significant change in the fluorescence the cross-linked polymer network in the presence of the test sample relative to the fluorescence of the cross-linked polymer network in the absence of the reference sample is indicative of the absence of the explosive in the sample. By significant change is meant that there is no change greater than typical measurement-to-measurement variation. In an embodiment, where there is no significant change in the fluorescence the cross-linked polymer network in the presence of the test sample relative to the fluorescence of the cross-linked polymer network in the absence of the reference sample is indicative of the absence of the explosive in the sample.

The energy of the conduction band of the cross-linked polymer network is greater than the lowest unoccupied molecular orbital of the analyte (e.g., explosive compound or degradation product thereof).

A wide variety of test samples can be used. The test sample may or may not comprise an explosive compound or degradation product (e.g. thermal degradation or photochemical degradation product) thereof. The explosive or degradation product thereof may be present in the gas phase in the test sample. For example, the explosive or degradation product is a vapor. The vapor can be the headspace above a liquid or solid sample (such as a swab used in airport screening). The test sample may be a gas phase sample. For example, the test sample is ambient air, the gas phase headspace above a liquid or solid sample (such as a swab used in airport screening), or a gas flowing over a liquid or solid sample that may comprise an explosive compound or degradation product thereof that is contacted with the cross-linked polymer network. In an embodiment, the test sample is not subjected to a pre-concentration step. In an embodiment, the test sample is a solution that may comprise the explosive compound or degradation product thereof. For example, the solution can be contacted with the cross-linked polymer network (e.g., thin film of cross-linked polymer network) and the solvent evaporated leaving the explosive compound or degradation product thereof, if present, as a solid sample in contact with the cross-linked polymer network. A reference sample is a test sample without an explosive compound or degradation product thereof.

Any explosive that quenches the fluorescence of the cross-linked polymer network can be detected. The explosives may be low-volatility explosives. Examples of explosives or explosives taggants that can be detected include nitramines (such as Research Department Explosive (RDX) (i.e., cyclotrimethylenetrinitramine)) and nitroesters (such as pentaerythritol tetranitrate (PETN), trinitrotoluene (TNT), dinitrotoluene (DNT), 2,4,6-triamino-1,3,5-trinitrobenzene (TATB), 2,3-dimethyl-2,3-dinitrobutane (DMNB)), and octahydro-1,3,5,7-tetranitro-1,3,5,7-tetrazocine (HMX). Examples of degradation products include thermal degradation products and photochemical degradation products.

Without intending to be bound by any particular theory, it is considered that the explosive compound or degradation product interacts with the cross-linked polymer network such that the fluorescence of the cross-linked polymer network is quenched. The quenching results in a significant (i.e., detectable) change in the fluorescence of the cross-linked polymer network in the presence of the test sample relative to the fluorescence of the cross-linked polymer network in the absence of the reference sample. For example, the fluorescence of the cross-linked polymer network is decreased by 0.1% to 100%, including all 0.1% values and ranges therebetween. The decrease in fluorescence can be non-linear with respect to the amount of analyte present.

The test sample may comprise an explosive compound or degradation production thereof and one or more commonly present volatile compounds (i.e., non-explosive compound or non-explosive compound degradation product). Examples of such commonly present volatile compounds include solvents, outgassed vapors from lipstick and sunscreen, organic compounds such as, for example, ethanol, pyridine, triethylamine, N-methylpiperidine, and aniline.

The explosive compound or degradation product can be detected at attogram amounts or less. The presence of an explosive compound or degradation product can be detected at from 1 nanogram to 1 attogram, including all values and ranges therebetween. The explosive compound or degradation product can be detected in the presence of other commonly present volatile compounds. In various embodiments, the presence of an explosive compound or degradation product can be detected at 1 picogram or less, 1 femtogram or less, or 1 attogram or less. In various embodiments, the presence of an explosive compound or degradation product in the gas phase can be detected at 1 picogram or less, or 1 femtogram or less, or 1 attogram or less. In an embodiment, the presence of an explosive compound or degradation product can be detected at the equilibrium vapor pressure or sub-equilibrium vapor pressure of the explosive compound or degradation product.

The steps of the methods of detecting explosives using the cross-linked polymer networks of the present disclosure described in the various embodiments and examples disclosed herein are sufficient to carry out the methods. Thus, in an embodiment, the method consists essentially of a combination of the steps of the methods disclosed herein. In another embodiment, the method consists of such steps.

In an aspect, the present disclosure provides a cross-linked polymer network that is a cross-linked porphyrin network (e.g., a porphyrin covalent organic framework (COF)) (also referred to herein as Porphyrin COF). The cross-linked porphyrin network is formed from a monomer comprising a plurality of polymerizable groups (e.g., alkene moieties) and a porphyrin moiety. The cross-linked polymer network is a cross-linked polymer network comprising a plurality of cross-linked porphyrin molecules.

In an embodiment, the cross-linked porphyrin network is an alkene-linked porphyrin covalent organic framework. The alkene-linked porphyrin covalent organic framework is formed from a monomer comprising a plurality of alkene moieties and a porphyrin moiety. For example, the alkene cross-linked porphyrin network is formed from an alkene functionalized porphyrin molecule (e.g., a porphyrin molecule having four alkene moieties). In an embodiment, an alkene-linked porphyrin covalent organic framework is a crystalline material and/or a powder and/or a porous (e.g., permanently porous) material.

The cross-linked porphyrin network is a crystalline material. For example, the cross-linked porphyrin network forms crystallites (i.e., discrete structures) where the longest dimension of the crystallites is 50 nm to 10 microns, including all values to the nanometer and ranges of nanometers therebetween. In various embodiments, the cross-linked porphyrin network comprises at least 2 unit cells, at least 5 unit cells, and at least 10 unit cells.

Figure 61:
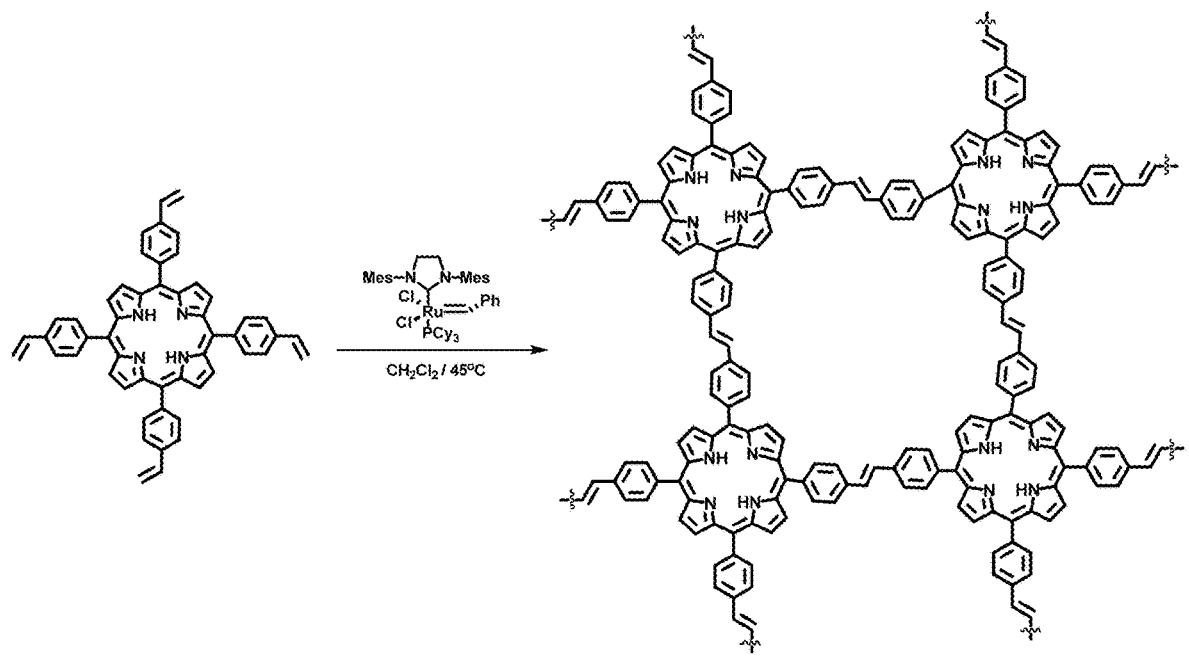
FIG. 61. Structure of an example of a porphyrin covalent organic framework (Porphyrin-COF).

In an embodiment, the cross-linked porphyrin network is that shown in FIG. 61, or a substituted analog thereof. In another embodiment, the cross-linked porphyrin network is formed from the monomer shown in FIG. 61, or a substituted analog thereof.

The cross-linked porphyrin networks have a porous (e.g., microporous (pores with a longest dimension of less than 2 nm) or mesoporous structure (pores with a longest dimension of 2 nm to 50 nm). The porous structure forms a repeating pattern (i.e., not a random distribution of pores) based at least in part on the structure of the monomer that makes up the cross-linked porphyrin network. In an 15 embodiment, the framework has pores, where the pores run parallel to the stacked aromatic moieties. In an embodiment, the pores have a longest dimension (e.g., a diameter) of from 2 nm to 6 nm, including all values to the 0.05 nm and ranges to the 0.1 nm therebetween. In one example, the pores are 2.3 nm in diameter.

The cross-linked porphyrin networks can have high surface area. For examples, the cross-linked porphyrin network can have a surface area 100 m$^2$/g to 2500 m$^2$/g, including all values to the m 2/g and ranges of surface area therebetween. The surface area of the cross-linked porphyrin network can be determined by methods known in the art, for example, by BET analysis of gas (e.g., nitrogen) adsorption isotherms.

The cross-linked porphyrin networks can exhibit desirable properties. For example, cross-linked porphyrin network can absorb light having a wavelength of from 200 nm to 1500 nm, including all values to the nanometer and ranges of nanometers therebetween. As another example, cross-linked porphyrin network can be semiconductors (e.g., exhibit semiconducting properties). As another example, cross-linked porphyrin network are thermally stable at temperatures of from 20° C. to 500° C., including all values to the degree Celsius and ranges of degrees Celsius therebetween.

The cross-linked porphyrin network can be used as, for example, catalysts, light absorbing materials, and in devices such as solar cells, photodetectors, and charge storage devices.

The following examples are presented to illustrate the present disclosure. They are not intended to be limiting in any manner.

EXAMPLE 1

In this example, a cross-linked phenylene vinylene-linked polymer network whose fluorescence is quenched by trace amounts of RDX introduced from solution or the vapor phase is demonstrated. Fluorescence quenching is reduced, but remains significant, when partially degraded RDX is employed, suggesting that the polymer responds to RDX itself. Pure solvents and outgassed vapors from lipstick or sunscreen do not quench polymer fluorescence.

1,3,5-trinitro-1,3,5-triazine (RDX) is a principal component of plastic explosives used in acts of terrorism and within improvised explosive devices (LEDs). Approaches to detect RDX compatible with remote, "stand-off" sampling that do not require preconcentration strategies, such as the swabs commonly employed in airports, will benefit military and civilian security. Such detection remains a significant challenge because RDX is $10^3$ less volatile than 1,3,5-trinitrotoluene (TNT), corresponding to a parts-per-trillion vapor pressure under ambient conditions. Therefore, while fluorescence quenching of conjugated polymers is sufficiently sensitive to detect TNT vapors, RDX vapor detection has previously been undemonstrated.

A conjugated polymer network was prepared using olefin metathesis. Polymer films exhibit fluorescence quenching when exposed to RDX delivered from solution and vapor phase (FIG. 1). This quenching response is not observed for solvent vapors or volatile compounds outgassed from common household items.

Figure 2:
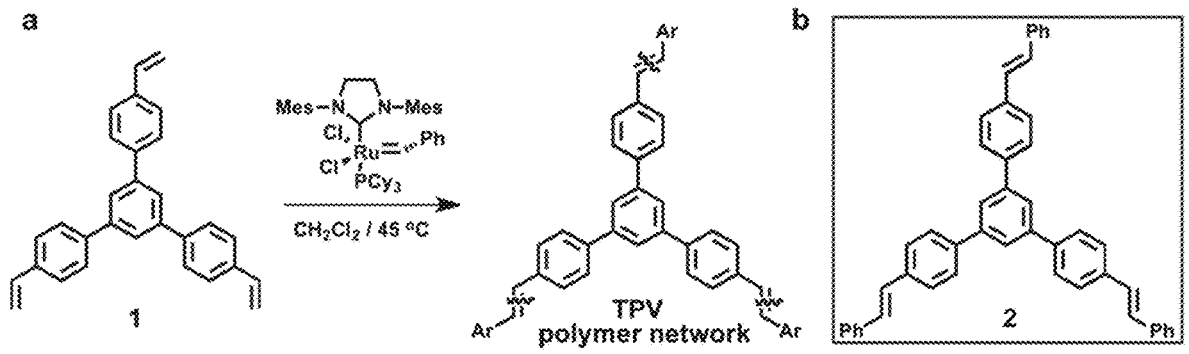
FIG. 2. Representative TPV synthesis a) Synthesis of a TPV network under ADMET reaction conditions, b) Structure of soluble model compound 2.
Figure 3:
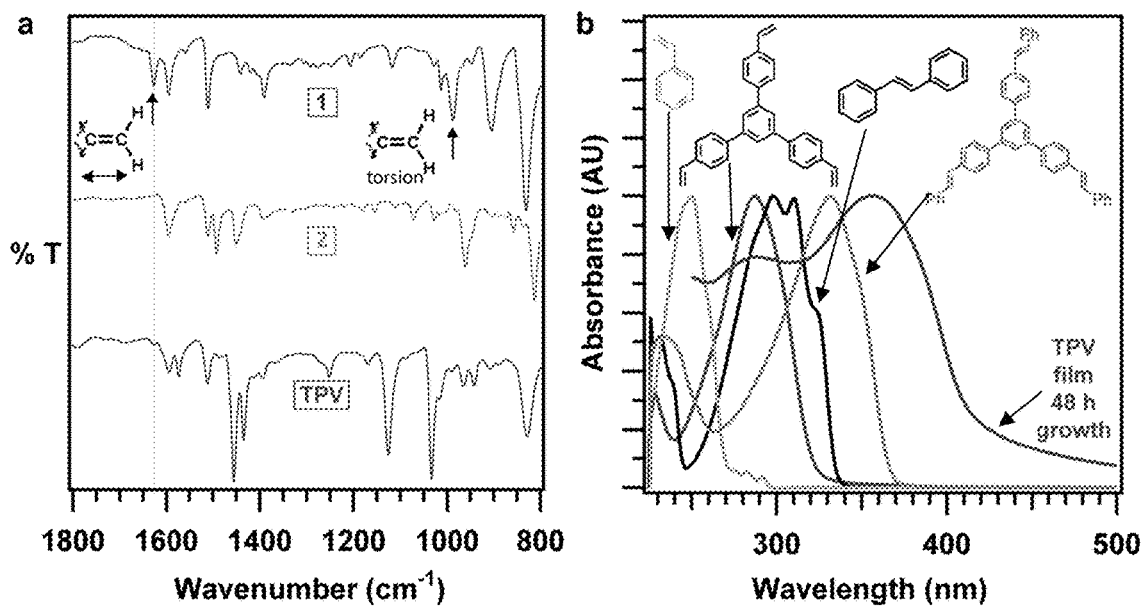
FIG. 3. Extent of reaction and increasing conjugation. a) Infrared spectra of 1, 2, TPV powder, b) Normalized UV-Vis spectra of styrene, 1, stilbene, 2 (each in $CH_2Cl_2$) and TPV film grown on fused $SiO_2$.
Figure 8:
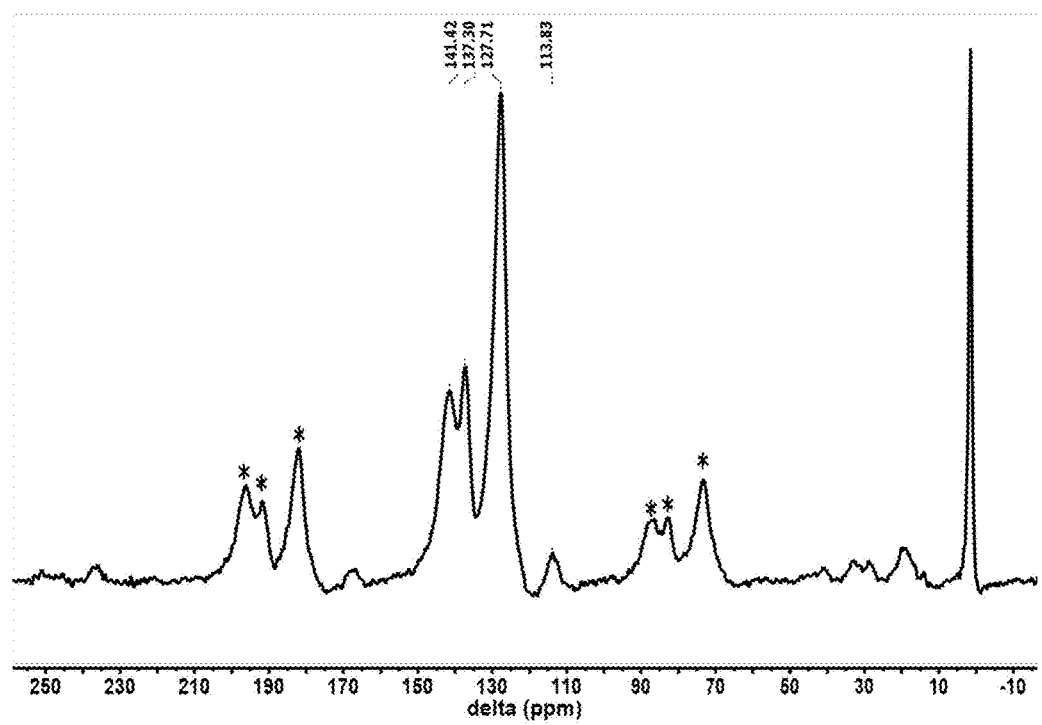
FIG. 8. $^{13}C$-CPMAS solid state NMR of a TPV powder.
Figure 9:
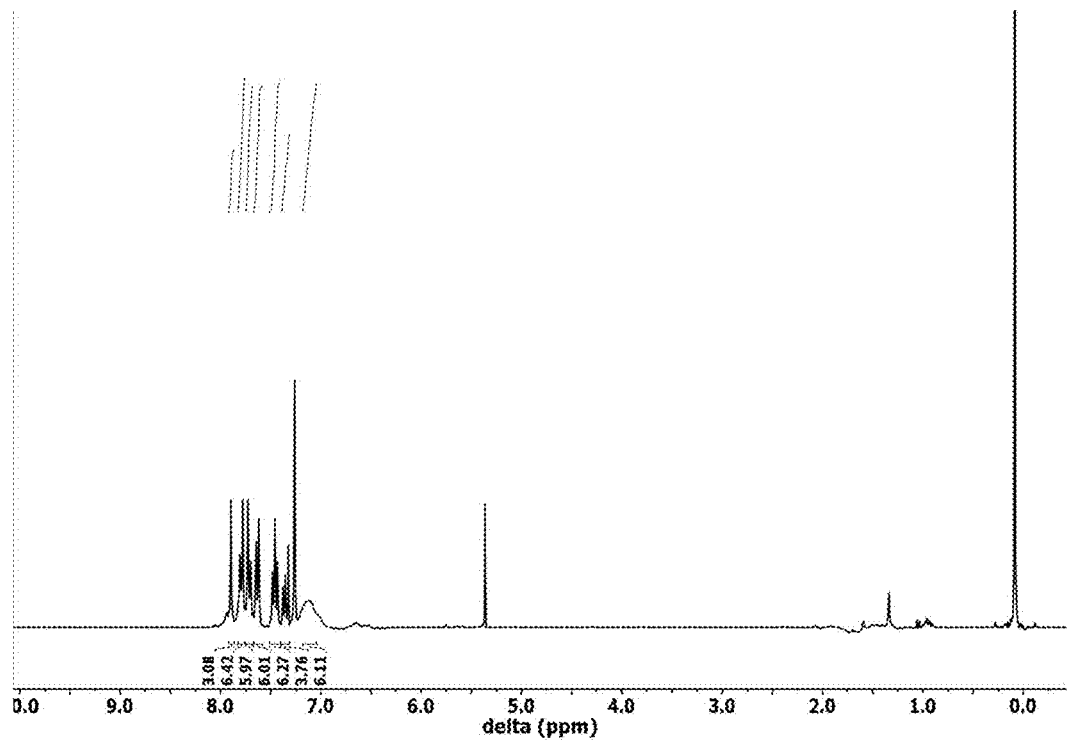
FIG. 9. $^1H$ NMR of 1,3,5-tris(stilbenyl) benzene 2 (300 MHz, $CDCl_3$, 298K) Spinning side-bands are denoted by "*".
Figure 10:
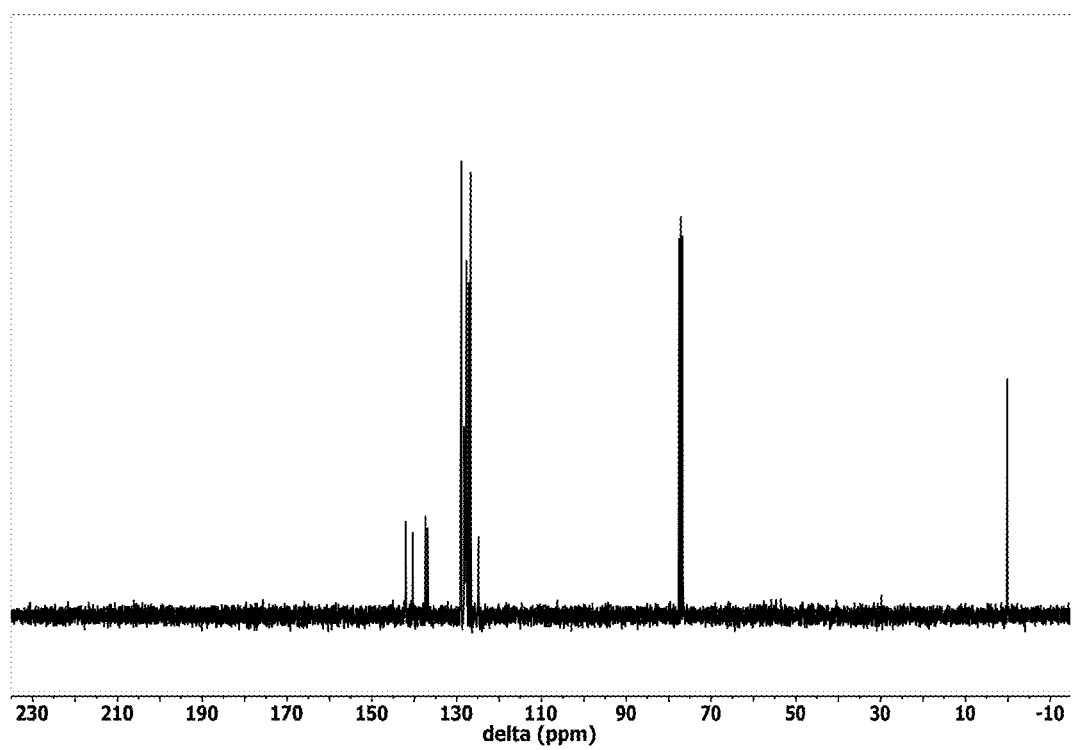
FIG. 10. $^{13}C$ NMR of 1,3,5-tris(stilbenyl) benzene 2 (75 MHz, $CDCl_3$, 298K).
Figure 17:
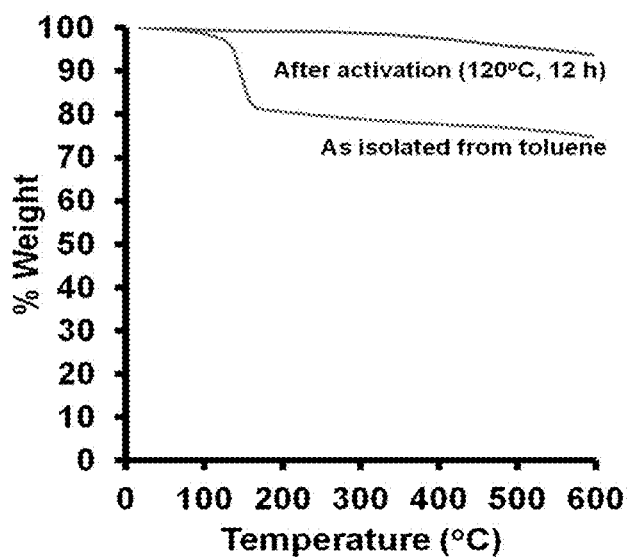
FIG. 17. Representative thermal gravimetric analysis (TGA) of a TPV powder.
Figure 18:
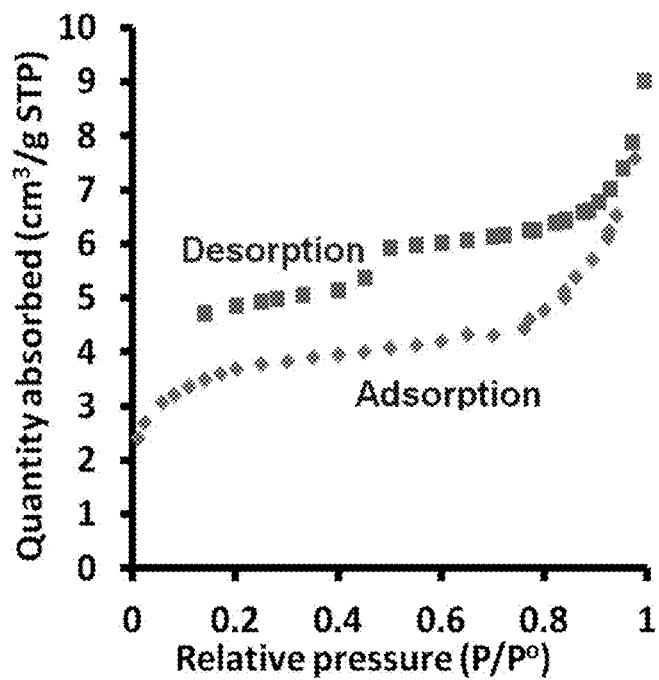
FIG. 18. Surface Area. Representative nitrogen adsorption isotherm of a TPV powder at 77K.
Figure 19:
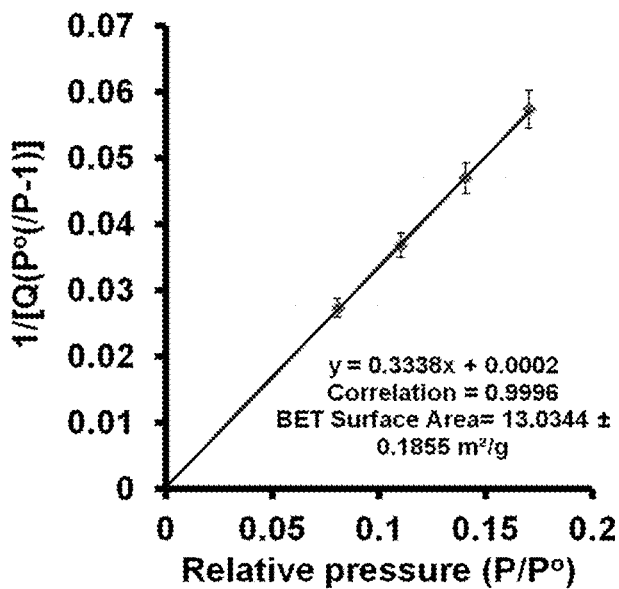
FIG. 19. Representative BET surface area plot calculated from isotherm data.
Figure 20:
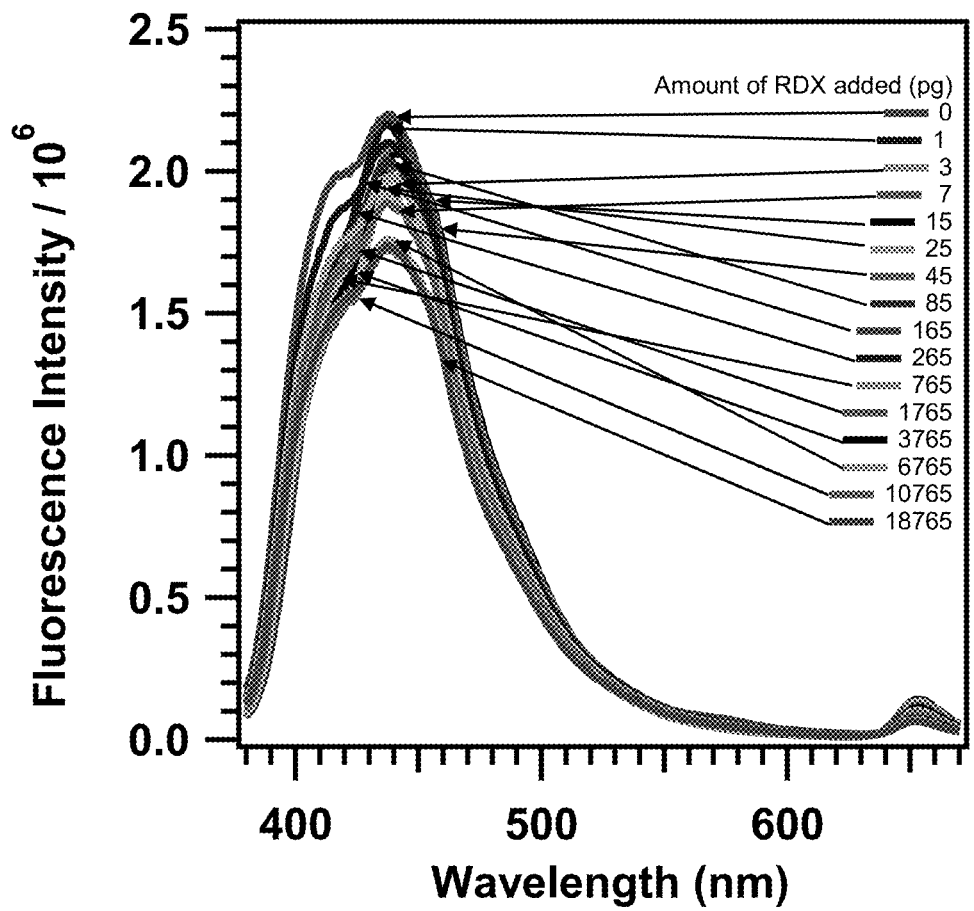
FIG. 20. Representative fluorescence response to extracted RDX 4 in 1:1 MeOH:$CH_3CN$, 24 hours growth, sample 2.
Figure 21:
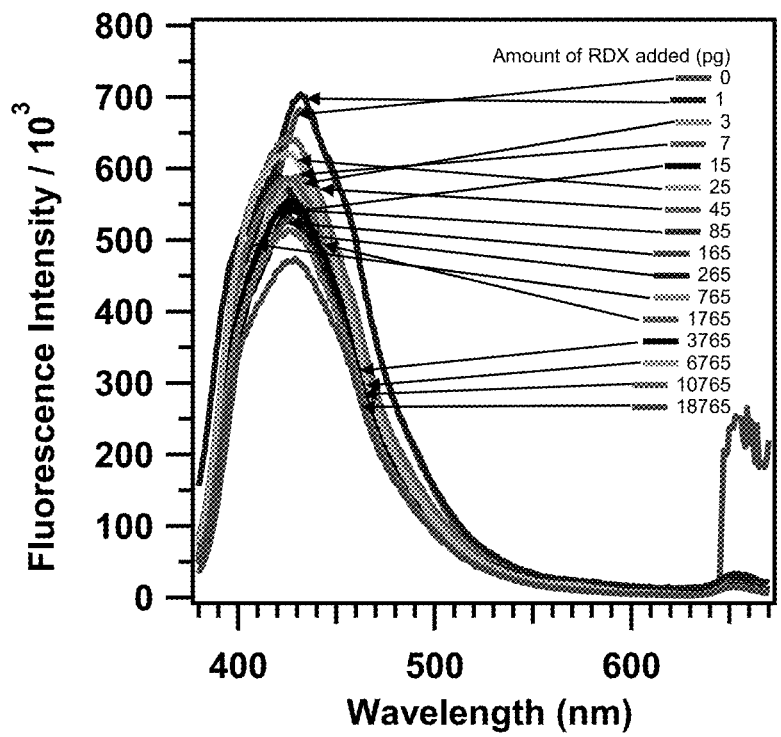
FIG. 21. Representative fluorescence response to extracted RDX 4 in 1:1 MeOH:$CH_3CN$, 24 hours growth, sample 3.
Figure 22:
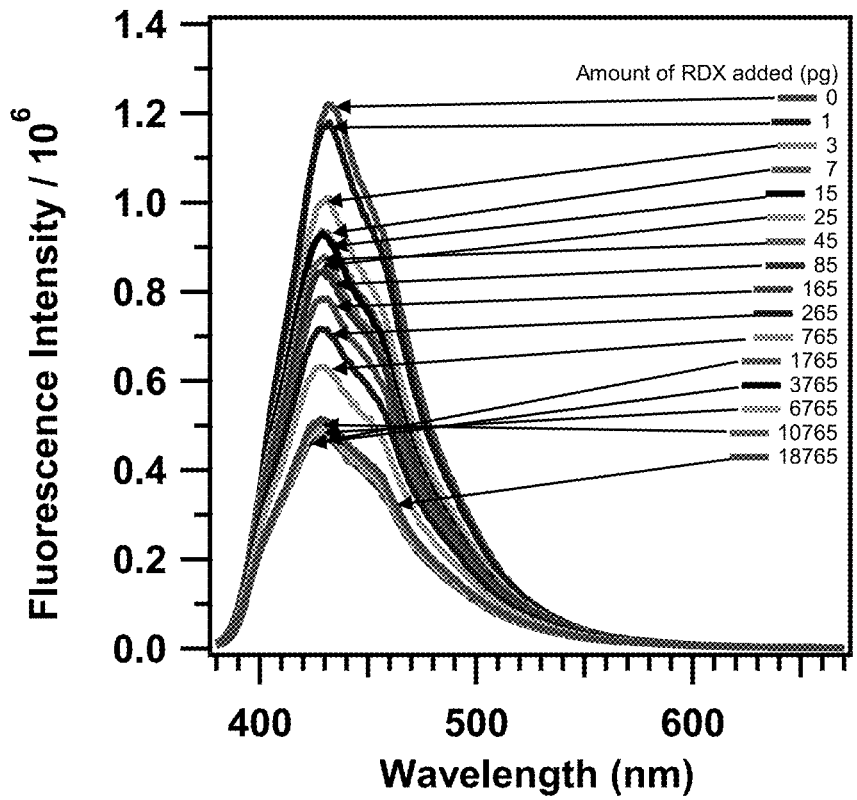
FIG. 22. Representative fluorescence response to extracted RDX 4 in 1:1 MeOH:$CH_3CN$, 48 hours growth, sample 2.
Figure 23:
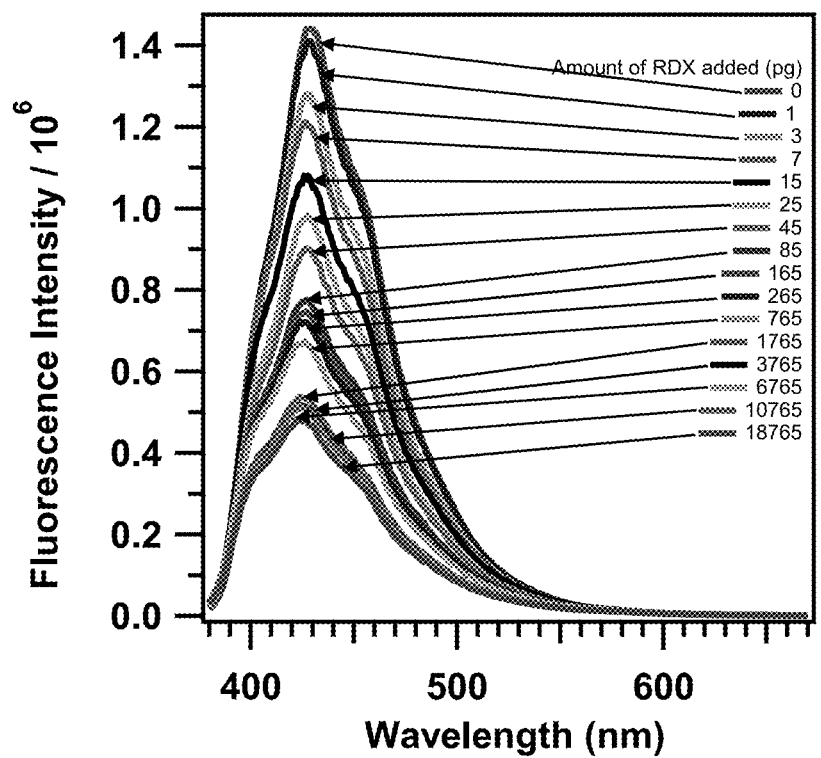
FIG. 23. Representative fluorescence response to extracted RDX 4 in 1:1 MeOH:$CH_3CN$, 48 hours growth, sample 3.
Figure 24:
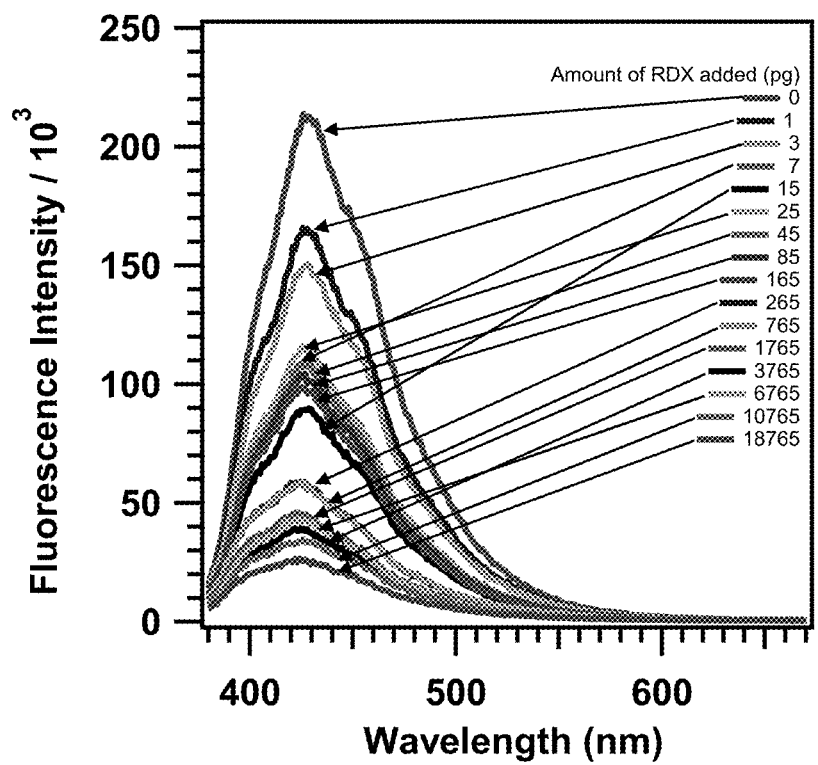
FIG. 24. Representative fluorescence response to extracted RDX 4 in 1:1 MeOH:$CH_3CN$, 72 hours growth, sample 2.
Figure 25:
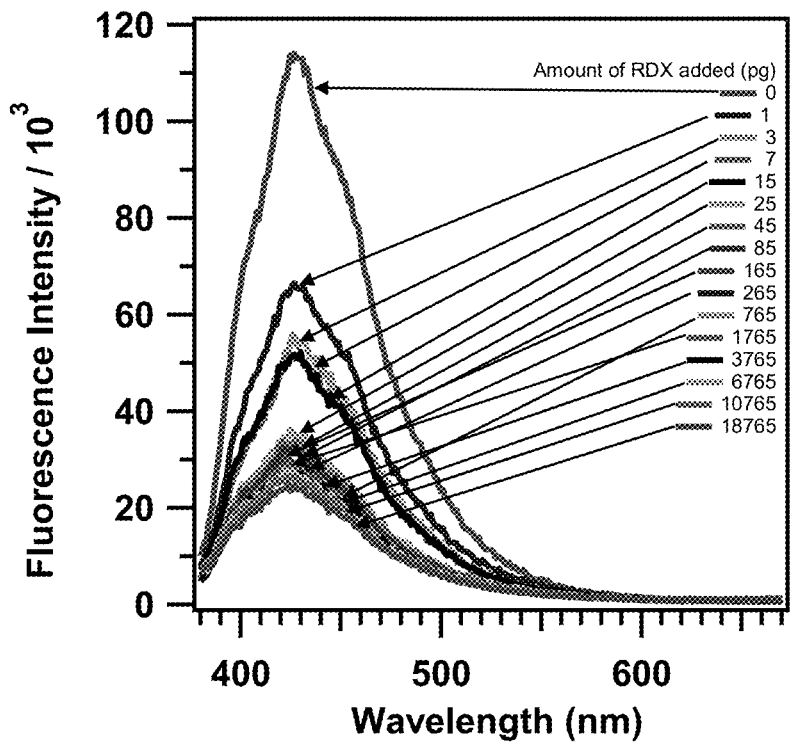
FIG. 25. Representative fluorescence response to extracted RDX 4 in 1:1 MeOH:$CH_3CN$, 72 hours growth, sample 3.

Conjugated networks were synthesized through an acyclic diene metathesis (ADMET) polymerization of a trifunctional styrene derivative 1 (FIG. 2). Olefin metathesis was chosen for its high functional group tolerance, mild reaction conditions, benign stoichiometric byproducts (ethylene) and synthetically convenient monomers. Derivative 1 was polymerized under solvothermal conditions in CH$_2$Cl$_2$ at 45° C. in the presence of 6 mol % of the Grubbs 2$^{nd}$ Generation olefin metathesis catalyst, which provided tris (phenylene)vinylene TPV as an insoluble amorphous powder. The TPV powders exhibited FT-IR spectra consistent with the formation of a network linked by stilbene moieties whereas monomer 1 exhibits bands corresponding to terminal alkene stretches and torsion peaks at 1627 cm$^{-1}$ and 987 cm$^{-1}$, respectively (FIG. 3a). These peaks are greatly attenuated in the TPV powders, in which most of these moieties are transformed into stilbene linkages. Tris(1,3,5-stilbenyl) benzene 2 (FIG. 2) was prepared as a model of the TPV network, which did not absorb at these wavenumbers. TPV powders were also characterized by solid-state $^{13}$C cross-polarization magic angle spinning (CP-MAS) NMR, which was also consistent with the expected stilbene-linked structure. The spectrum indicates two broad aromatic resonances centered at 141 and 137 ppm, as well as a peak corresponding to the vinylic carbons at 128 ppm (FIG. 8). Despite the known reversibility of olefin metathesis, which might give rise to a crystalline network, all samples of TPV prepared under these conditions are amorphous and non-porous, as indicated by their low N2 uptake (FIGS. 18-19). They may be heated to 600° C. before decomposing to volatile products, as determined by thermogravimetric analysis (FIG. 17).

Figure 13:
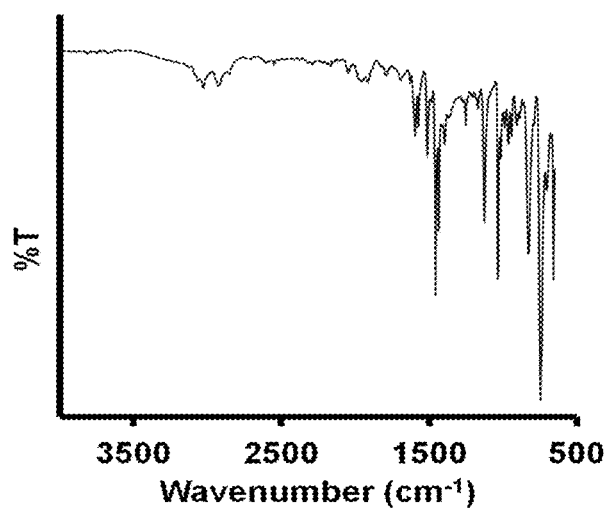
FIG. 13. Representative FT-IR spectra of a TPV powder.
Figure 14:
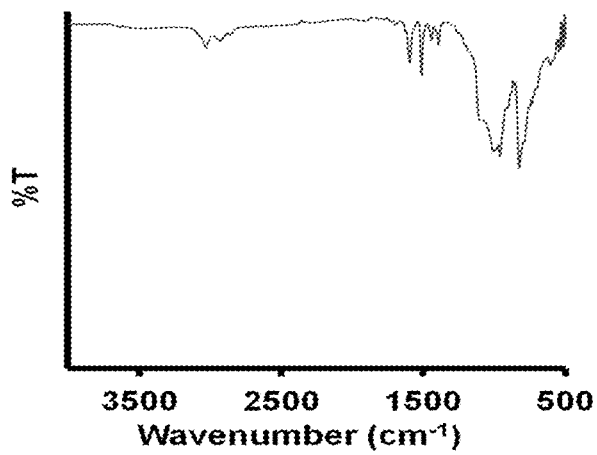
FIG. 14. Representative FT-IR microscopy of a TPV thin film on single layer graphene (SLG)/$SiO_2$.
Figure 15:
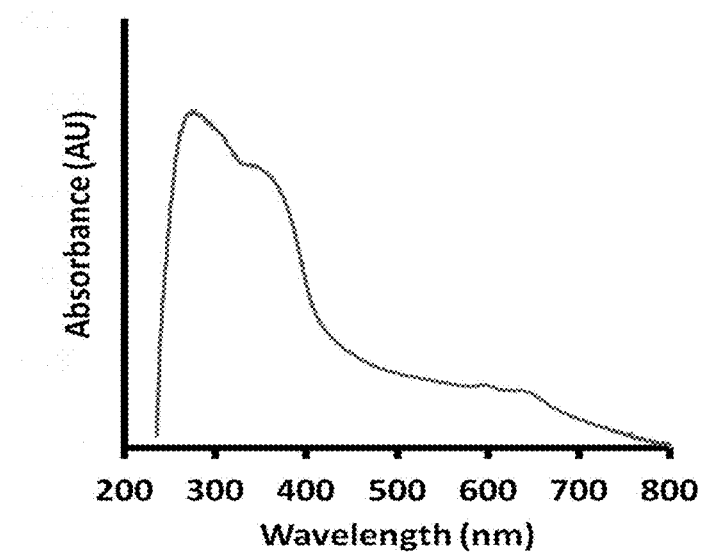
FIG. 15. Representative diffuse reflectance UV/Vis spectrum of a TPV powder.
Figure 16:
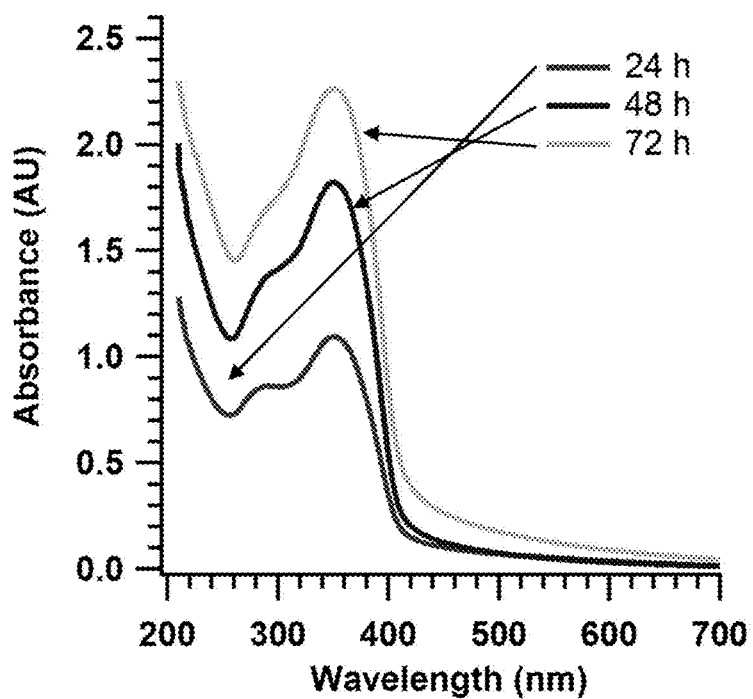
FIG. 16. Representative UV of examples of TPV films grown under different reaction times.
Figure 57:
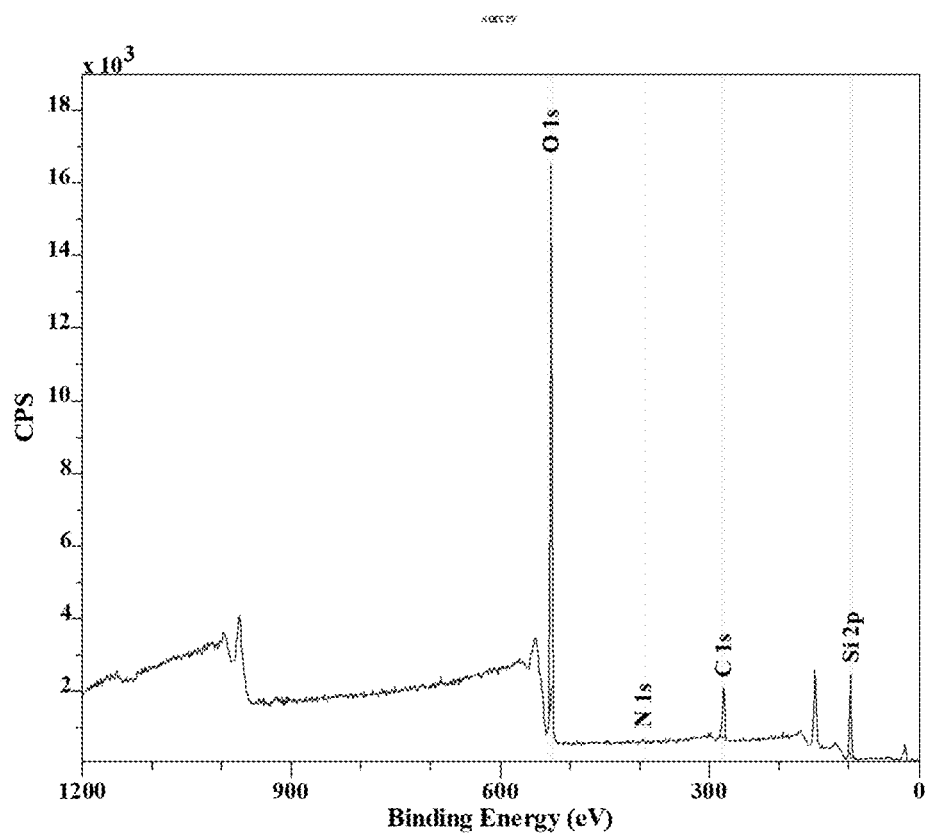
FIG. 57. Representative X-ray Photoelectron Spectroscopy of a TPV thin film on $SiO_2$.
Figure 58:
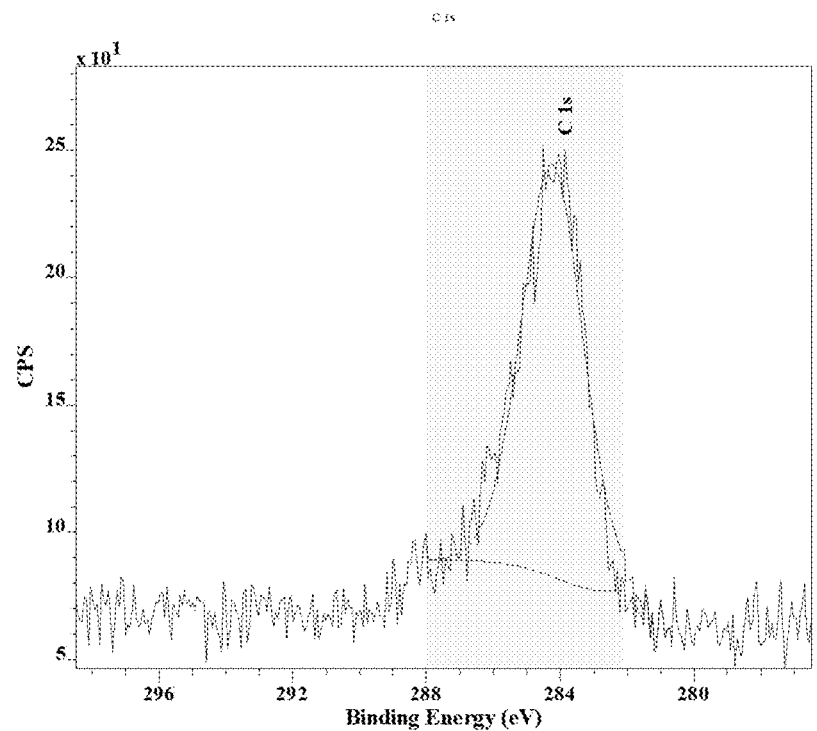
FIG. 58. Representative X-ray Photoelectron Spectroscopy of a TPV thin film on $SiO_2$. C1s spectrum.
Figure 59:
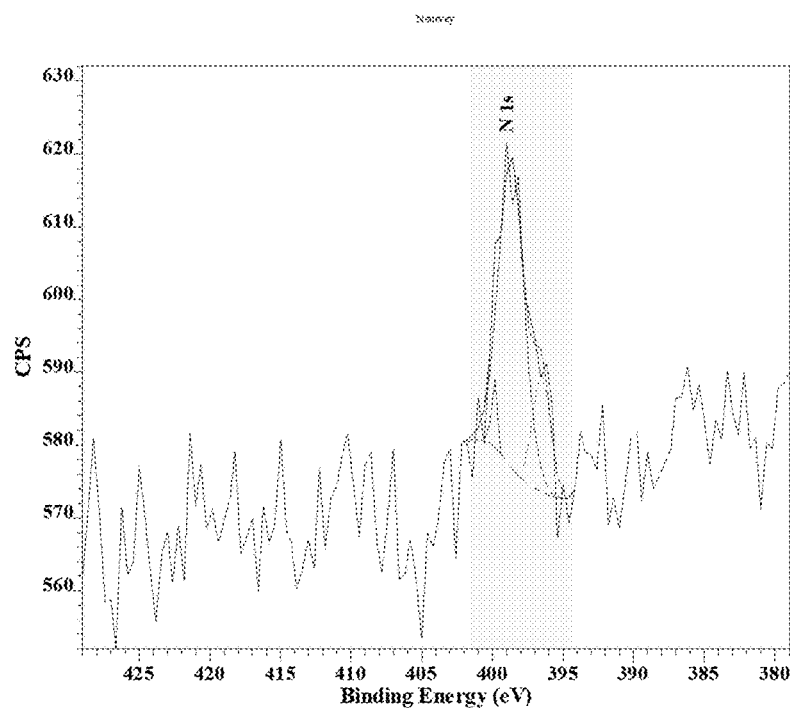
FIG. 59. Representative X-ray Photoelectron Spectroscopy of a TPV thin film on $SiO_2$. N1s spectrum.

Although characterizing the powder form of 1 provides confirmation of the network structure, these powders strongly scatter light and are not ideal for detecting explosives via fluorescence quenching. Linear conjugated polymers are readily processed into films using solution-based methods, such as spin-coating or drop-casting. In contrast, cross-linked networks are inherently insoluble. Thin films of TPV by including a fused $SiO_2$ substrate in the reaction vessel during its synthesis were prepared instead. The resulting films were washed extensively with $CH_2Cl_2$ to remove soluble byproducts and then activated by solvent evaporation under ambient conditions. The films show similar FT-IR spectra (FIG. 13) as the TPV powders and are also amorphous, as determined by grazing incidence X-ray diffraction at the Cornell High Energy Synchrotron Source (CHESS). X-ray photoelectron spectroscopy indicated a narrow carbon signal centered at 284 eV, corresponding to the sp 2-hybridized carbons within the TPV network. Strong Si and O peaks were also observed that originate from the fused $SiO_2$ substrate. Peaks corresponding to Ru were not observed, and only trace N was detected, indicating low amounts of catalyst decomposition products in the films (FIGS. 57-59).

The electronic absorption and fluorescence of the films show subtle but reproducible differences as a function of the reaction time, which also proved to strongly impact their RDX response. UV/Vis spectra of the TPV films yield local maxima at 287 and 358 nm. The 358 nm peak increases in intensity relative to that of 287 nm as a function of reaction time. Films grown for 1 hour showed as $I_{358}/I_{287}$ ratio of 0.87, which increased to ~1.2 at 24 and 48 hours reaction times. The 287 nm peak of films grown for 72 hours typically appeared only as a shoulder of the 358 nm peak (Table 1). These spectral changes are attributed to increased conversion of styrene to stilbene moieties in the films. This conclusion was further supported by the solution absorption spectra of relevant model compounds. The $\lambda_{max}$ of styrene (250 nm) and monomer 1 (287 nm) correspond to the 287 nm absorption observed in the TPV film. The spectra of stilbene (298 nm) and model compound 2 (332 nm) indicative of extended conjugation (FIG. 3b). These peaks correspond well to the 358 nm absorption of the TPV film, which is red-shifted further due to its greater conjugation and/or aggregated thin-film structure. In summary, UV/Vis spectroscopy provides a qualitative indication of the extent of the olefin metathesis reaction in the TPV films and suggests increased conversion of the metathesis reaction over reaction times up to 72 hours.

Figure 4:
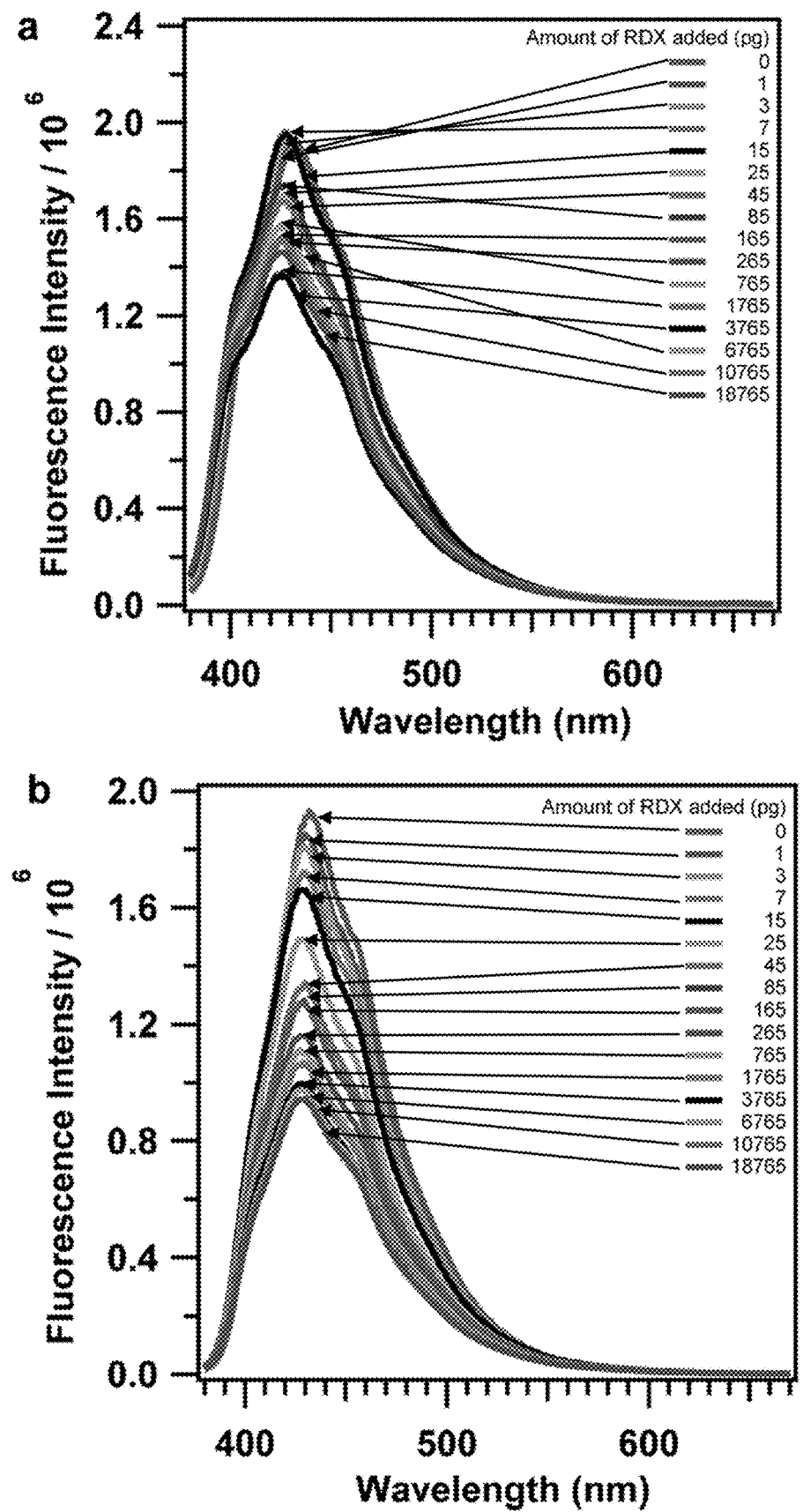
FIG. 4. Representative example of detection of RDX introduced from a 1:1 $CH_3CN$:MeOH solution, a) Quenching of fluorescence of a TPV film grown for 24 hours, b) Quenching of fluorescence of a TPV film grown for 48 hours, c) Quenching of fluorescence of a TPV film grown for 72 hours, d) example of relative quenching % of TPV films on exposure to RDX in solution with varying time of reaction, e) example of fluorescence quenching % of TPV films grown for 72 hours in response to attogram (ag) quantities of RDX, f) Response of 72 hours TPV films to 1:1 v/v $CH_3CN$:MeOH solution in the absence of RDX.
Figure 4:
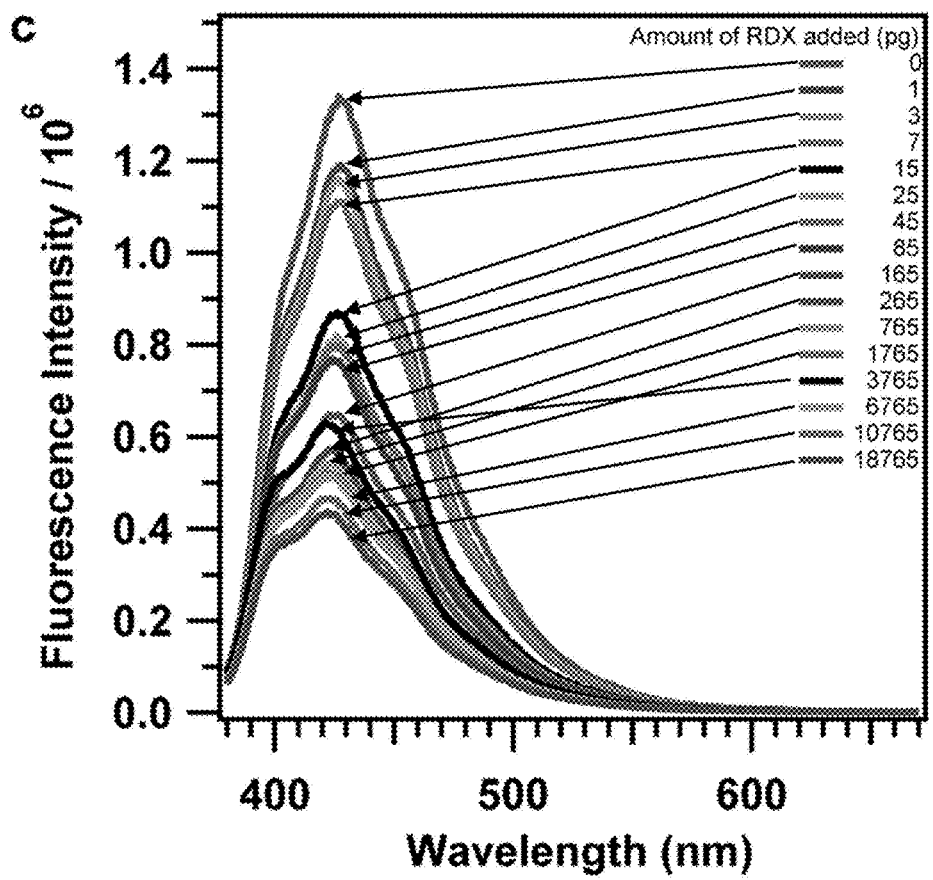
Figure 4:
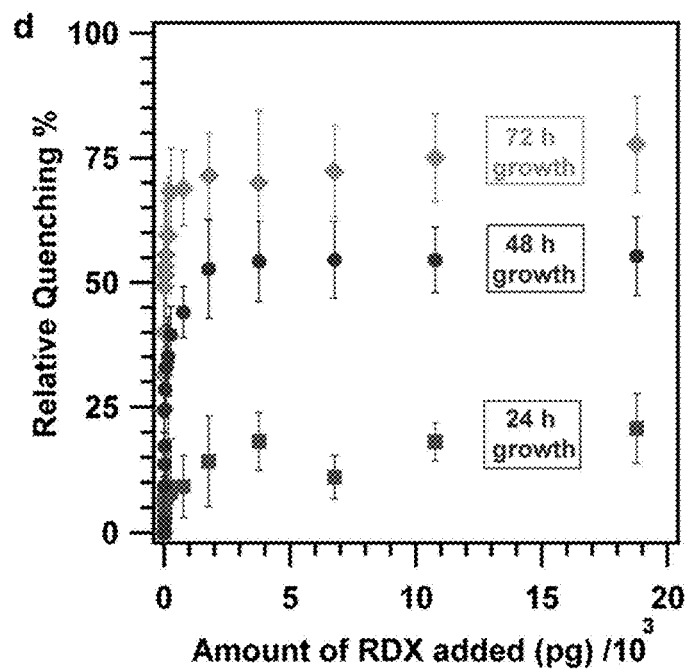
Figure 4:
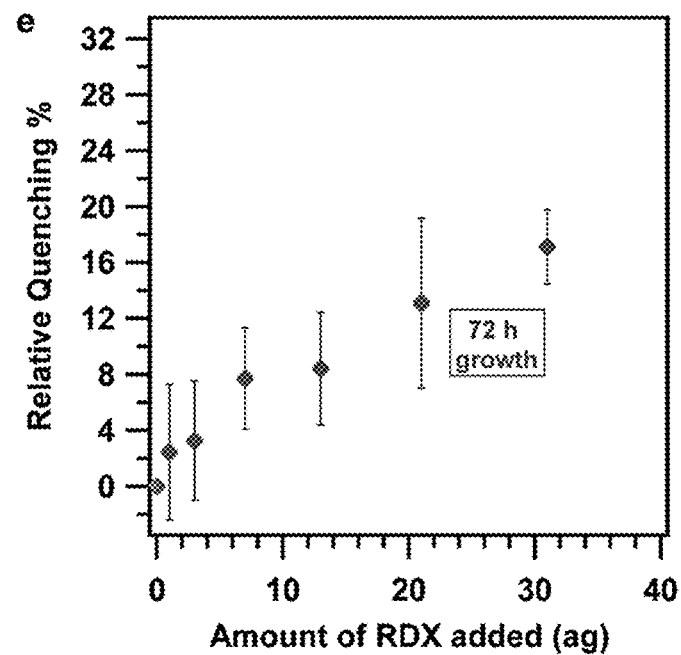
Figure 4:
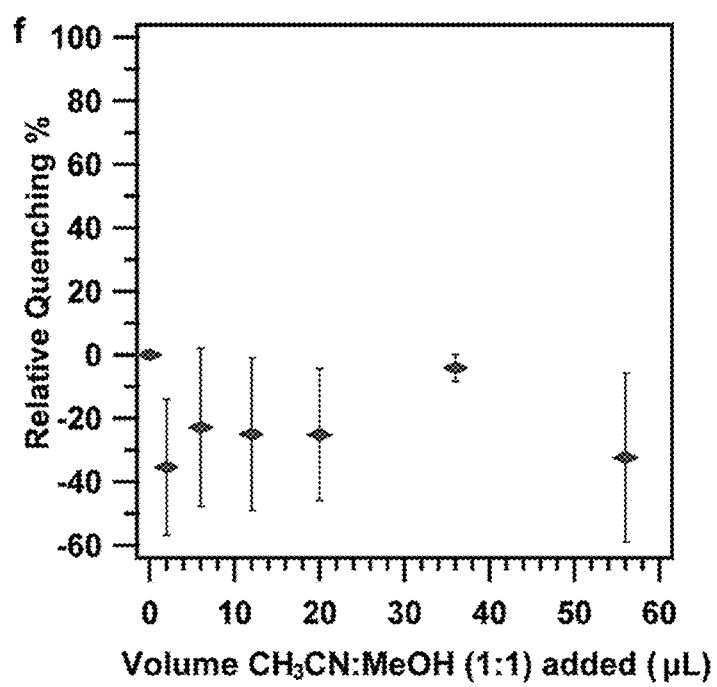
Figure 5:
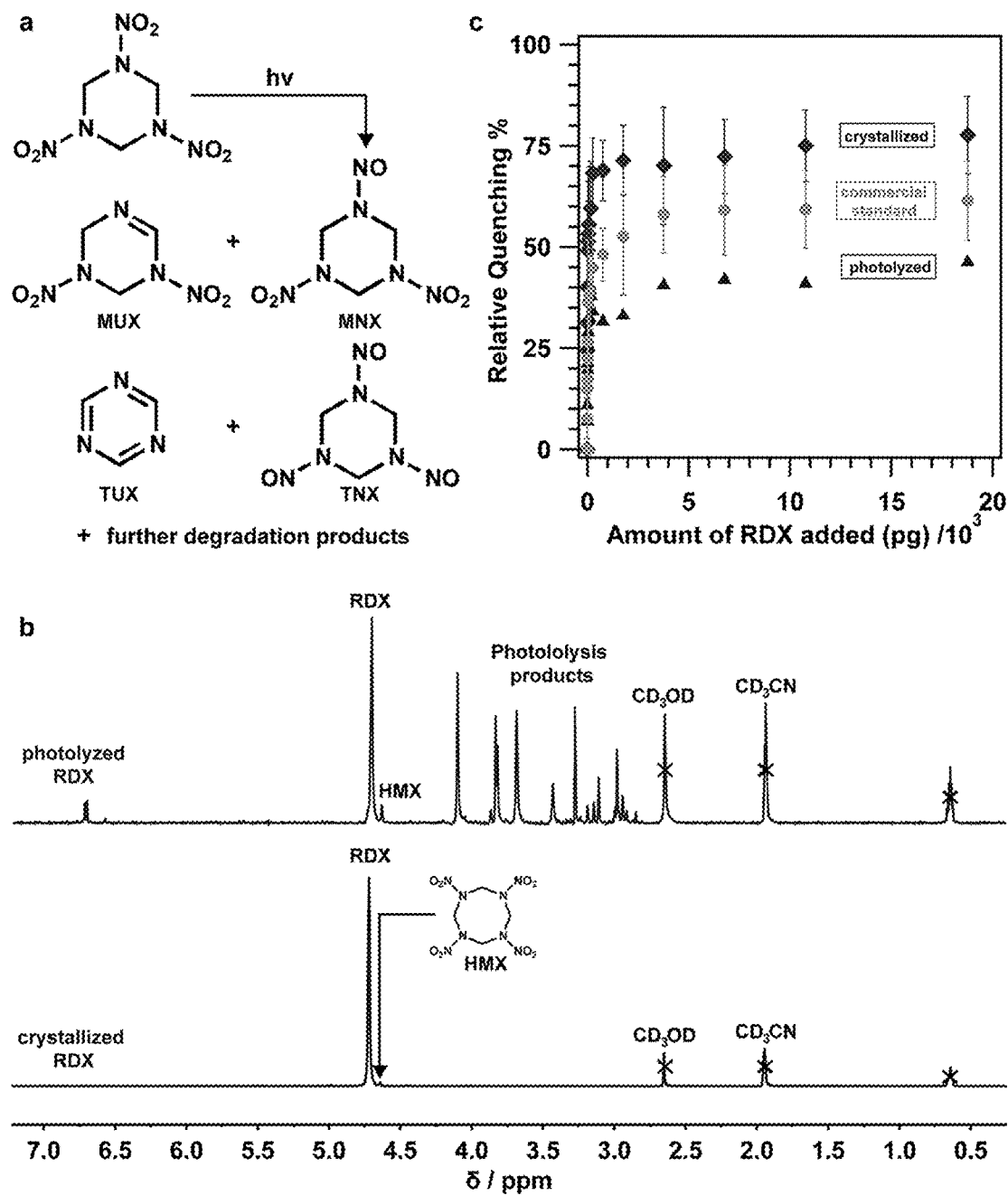
FIG. 5. Representative response of TPV films to photolyzed RDX, a) Schematic of several possible RDX photolysis products, b) Partial $^1H$ NMR spectra (300 MHz 1:1 CD 3 CN:$CD_3OD$, 298 K) of crystallized RDX before and after irradiation with UV light. The photolyzed spectrum shows clear evidence of RDX degradation, c) Fluorescence quenching curves of examples of 72 hours TPV films exposed to solutions of crystallized, photolyzed and a RDX commercial standard.
Figure 6:
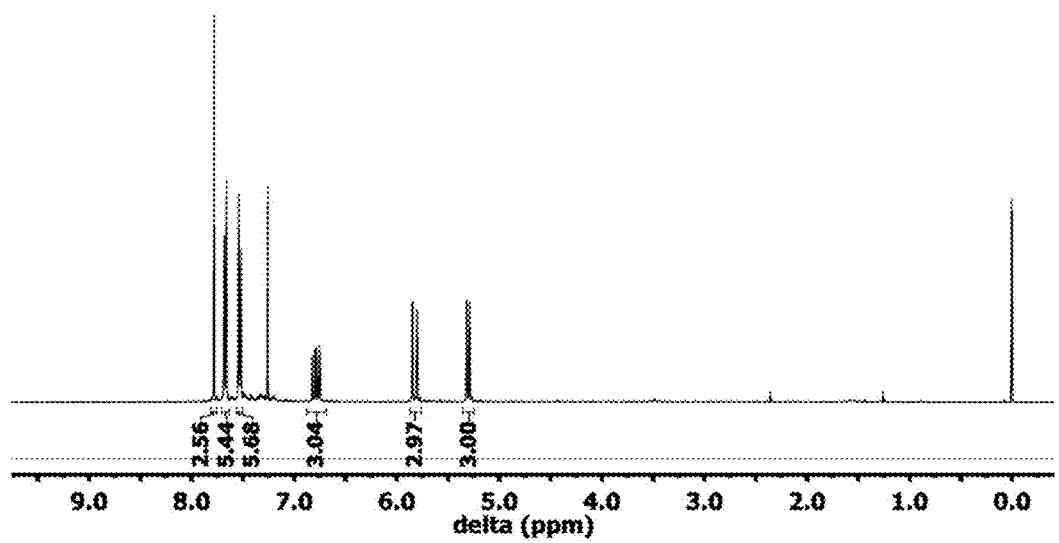
FIG. 6. $^1H$ NMR of 1,3,5-tri(4-vinylphenyl)-benzene 1 (400 MHz, $CDCl_3$, 298K).
Figure 7:
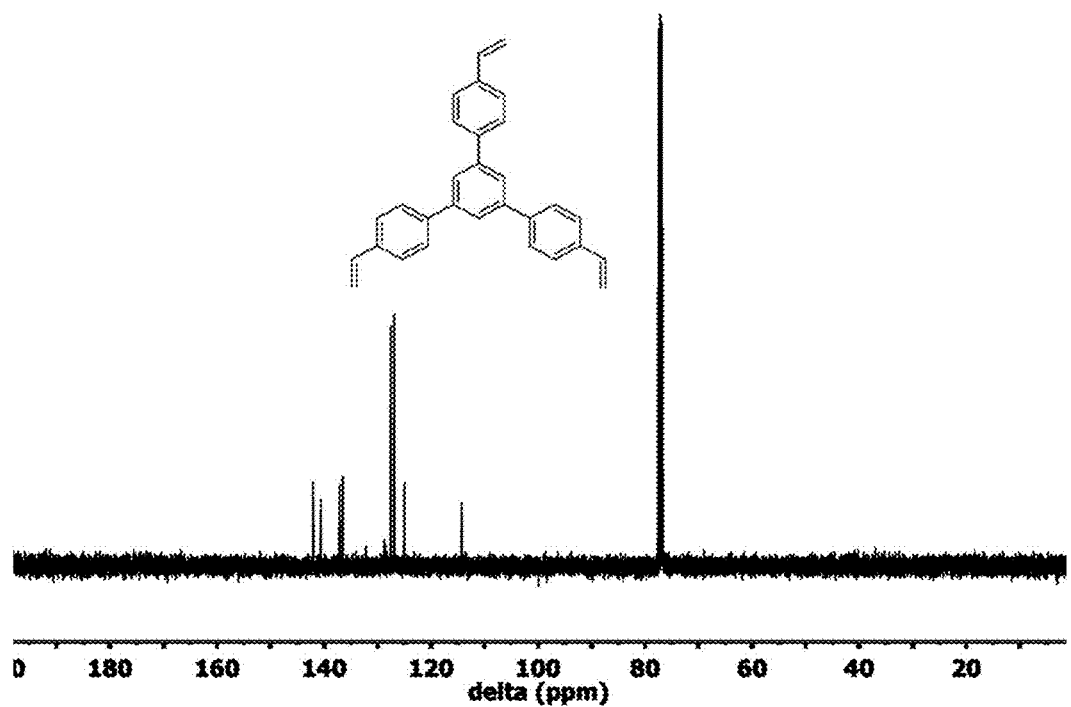
FIG. 7. $^{13}C$ NMR of 1,3,5-tri(4-vinylphenyl)-benzene 1 (100 MHz, $CDCl_3$, 298K).
Figure 29:
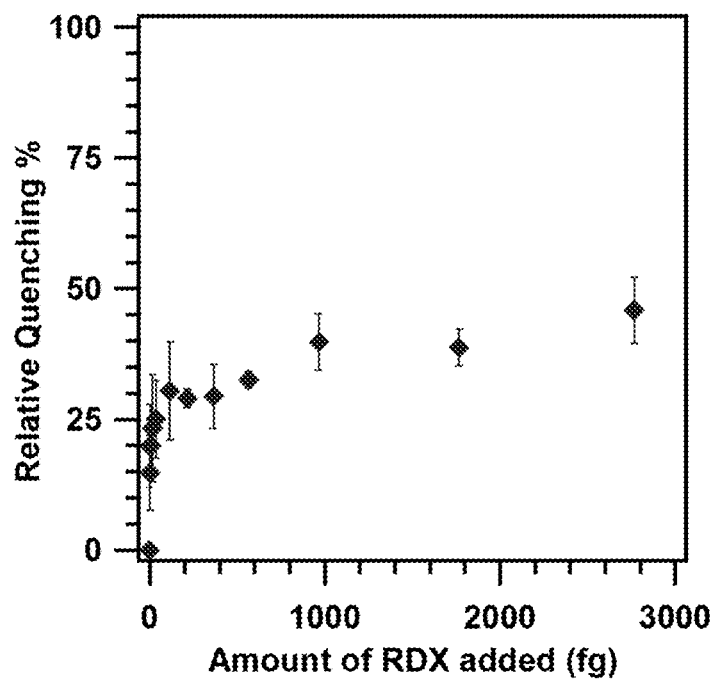
FIG. 29. Representative relative quenching % of examples of 72 hours TPV films to femtogram of RDX solution prepared from extracted RDX 4. Each point is the average of the response of three different films.
Figure 30:
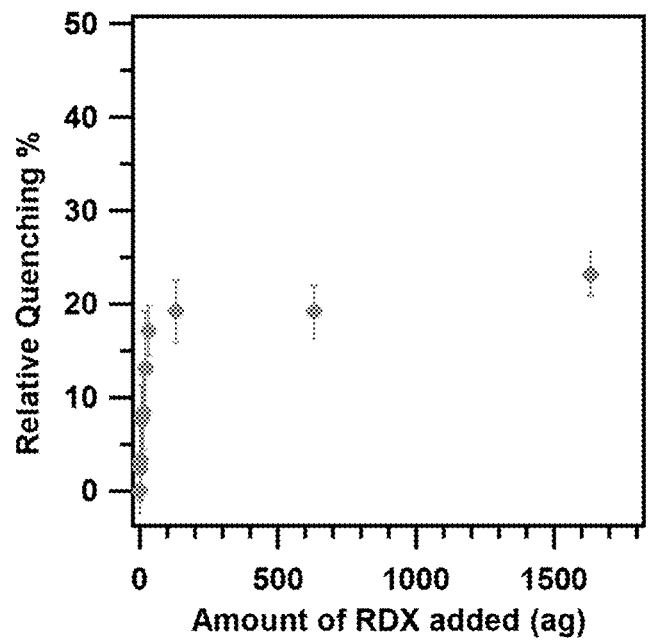
FIG. 30. Representative relative quenching % of examples of 72 hours TPV films to attogram of RDX solution prepared from extracted RDX 4. Each point is the average of the response of three different films.
Figure 31:
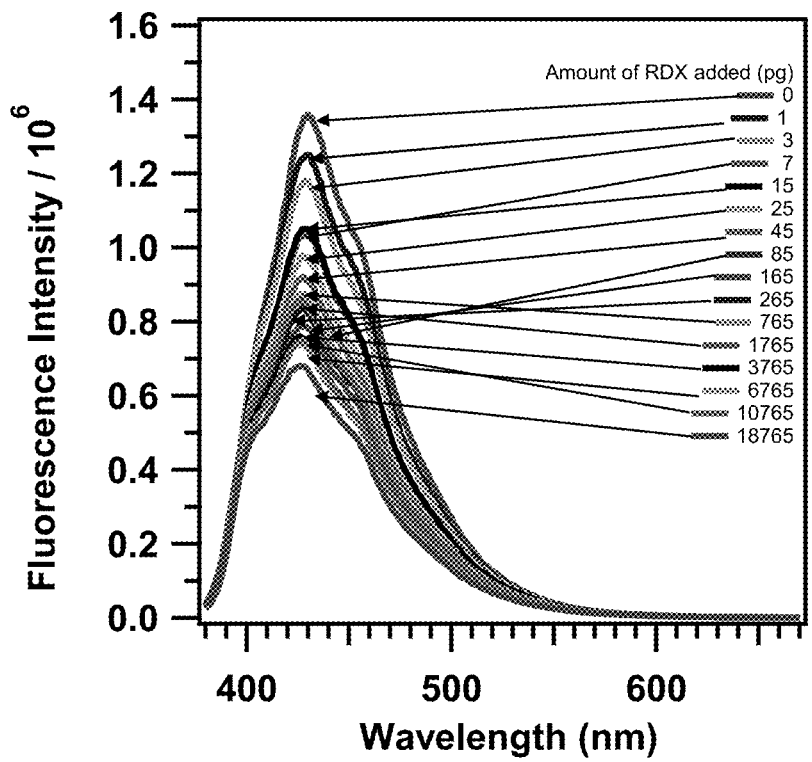
FIG. 31. Representative raw fluorescence data of examples of 72 hours TPV films exposed to irradiated RDX solution.
Figure 32:
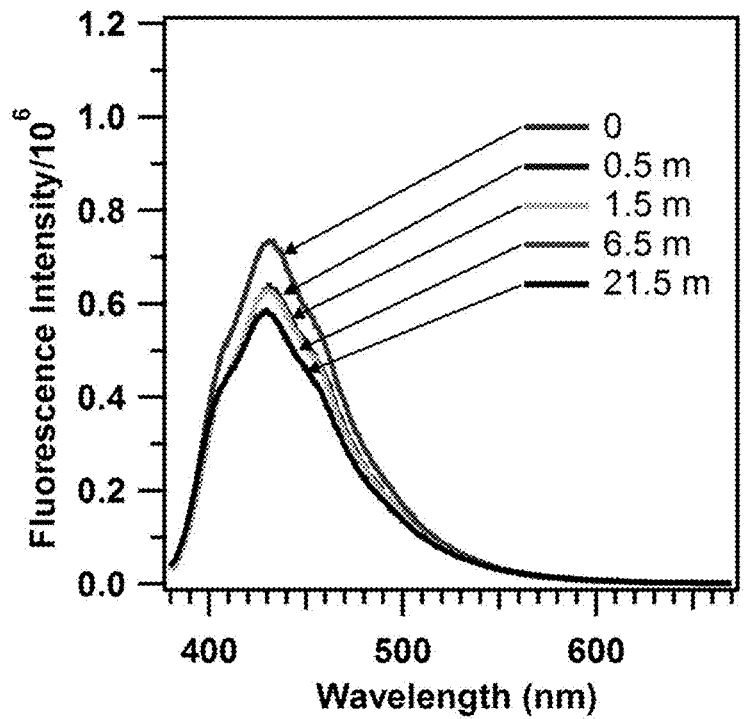
FIG. 32. Representative raw fluorescence data of examples of TPV films exposed to RDX vapors from extracted RDX 4 placed in a darkened vacuum chamber, sample 1, 24 hours.
Figure 33:
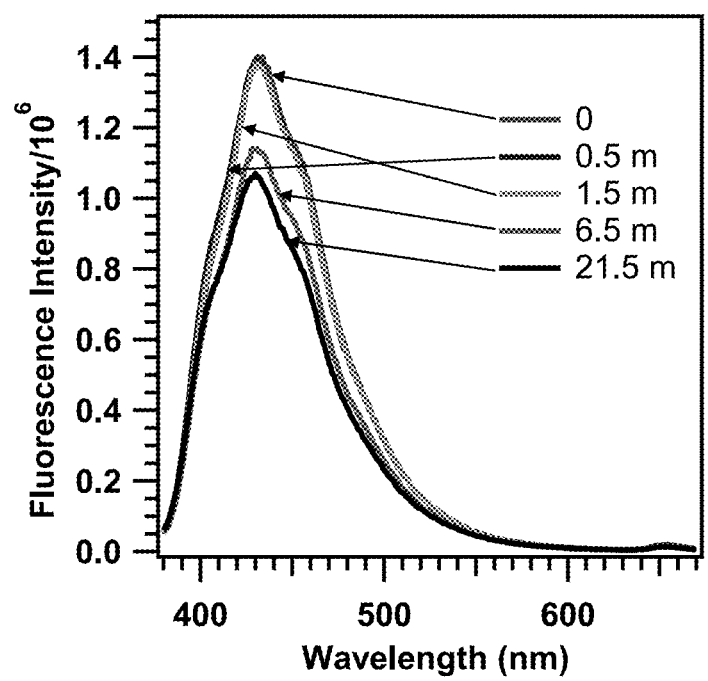
FIG. 33. Representative raw fluorescence data of examples of TPV films exposed to RDX vapors from extracted RDX 4 placed in a darkened vacuum chamber, sample 2, 24 hours.
Figure 34:
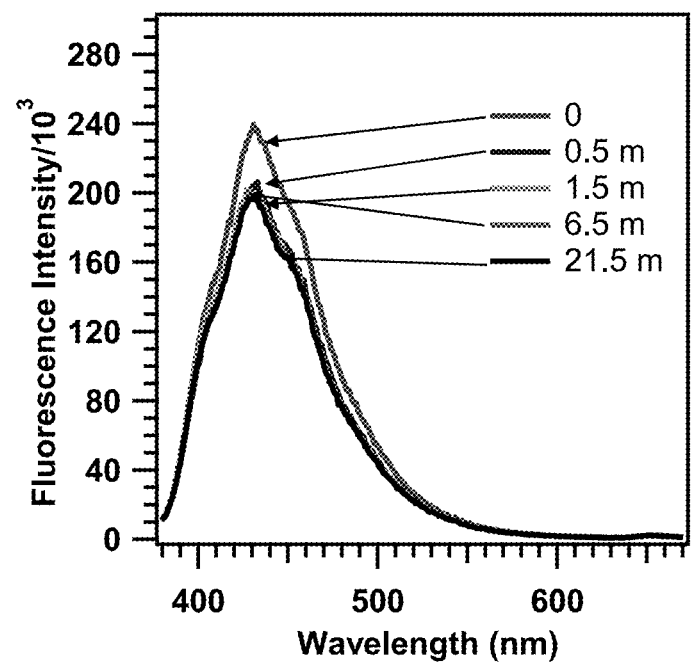
FIG. 34. Representative raw fluorescence data of examples of TPV films exposed to RDX vapors from extracted RDX 4 placed in a darkened vacuum chamber, sample 3, 24 hours.
Figure 35:
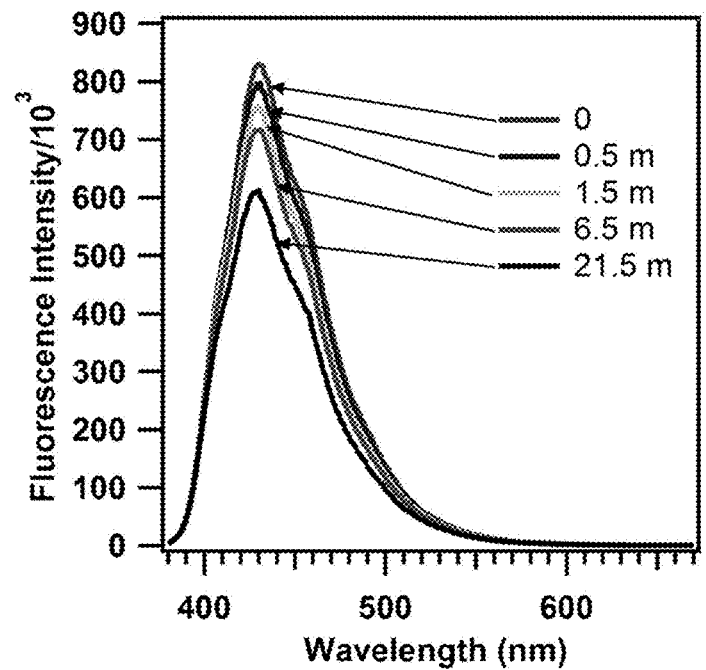
FIG. 35. Representative raw fluorescence data of examples of TPV films exposed to RDX vapors from extracted RDX 4 placed in a darkened vacuum chamber, sample 1, 48 hours.
Figure 36:
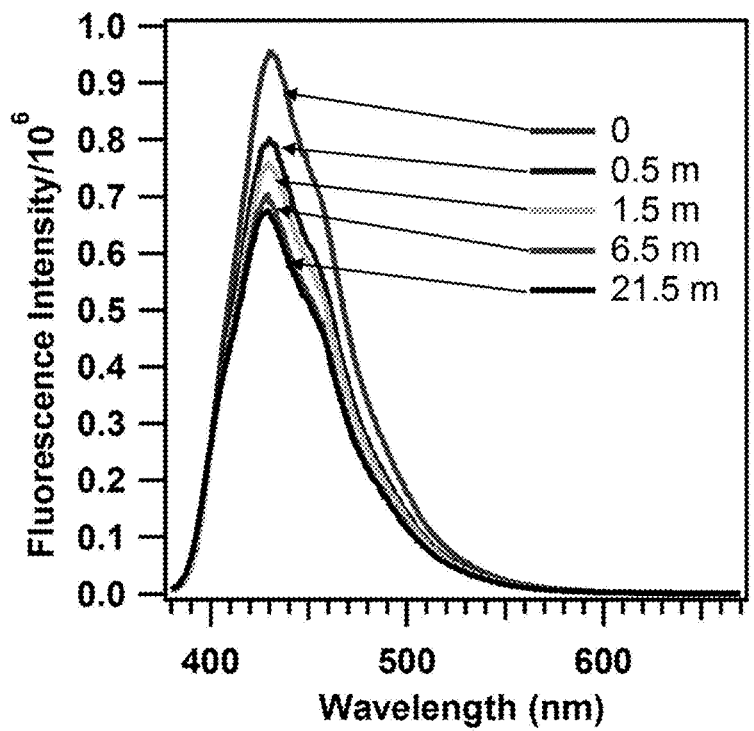
FIG. 36. Representative raw fluorescence data of examples of TPV films exposed to RDX vapors from extracted RDX 4 placed in a darkened vacuum chamber, sample 2, 48 hours.
Figure 37:
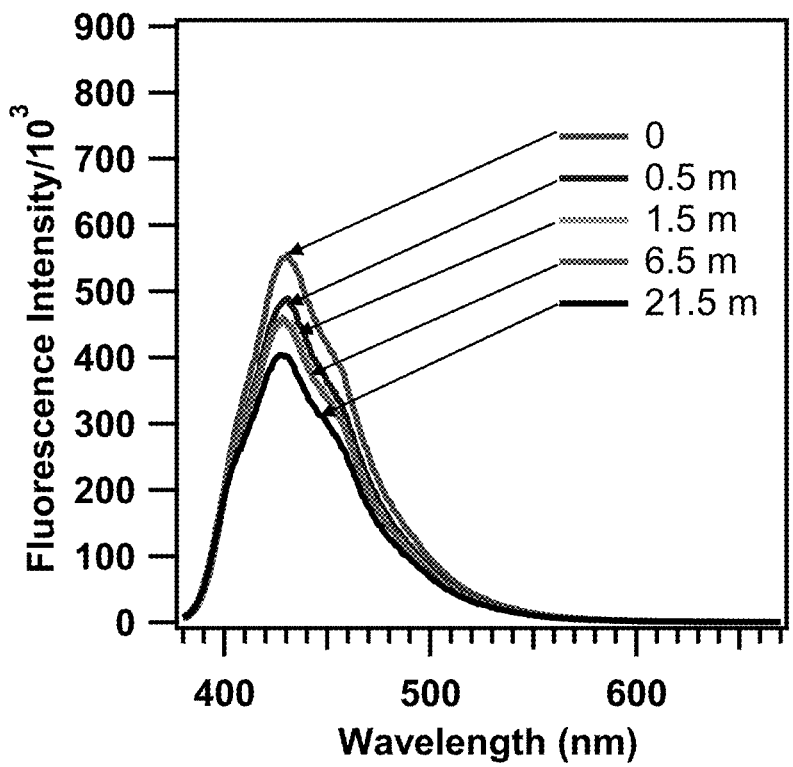
FIG. 37. Representative raw fluorescence data of examples of TPV films exposed to RDX vapors from extracted RDX 4 placed in a darkened vacuum chamber, sample 3, 48 hours.
Figure 38:
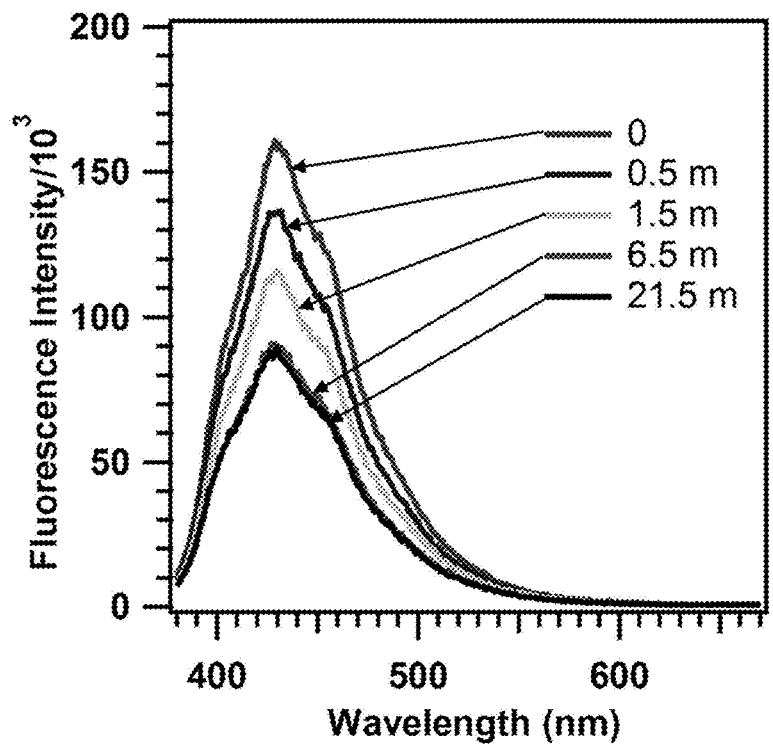
FIG. 38. Representative raw fluorescence data of examples of TPV films exposed to RDX vapors from extracted RDX 4 placed in a darkened vacuum chamber, sample 1, 72 hours.
Figure 39:
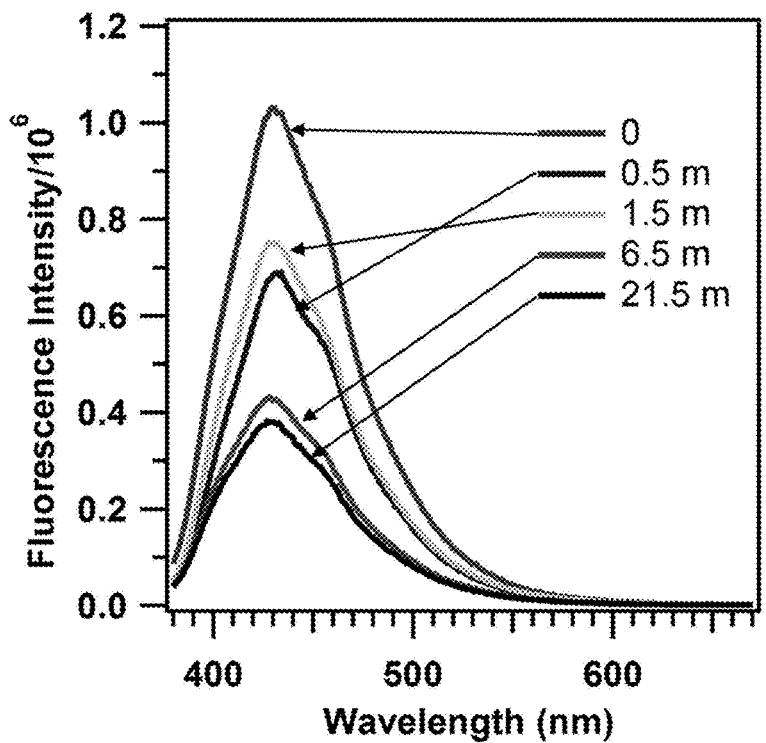
FIG. 39. Representative raw fluorescence data of examples of TPV films exposed to RDX vapors from extracted RDX 4 placed in a darkened vacuum chamber, sample 2, 72 hours.
Figure 40:
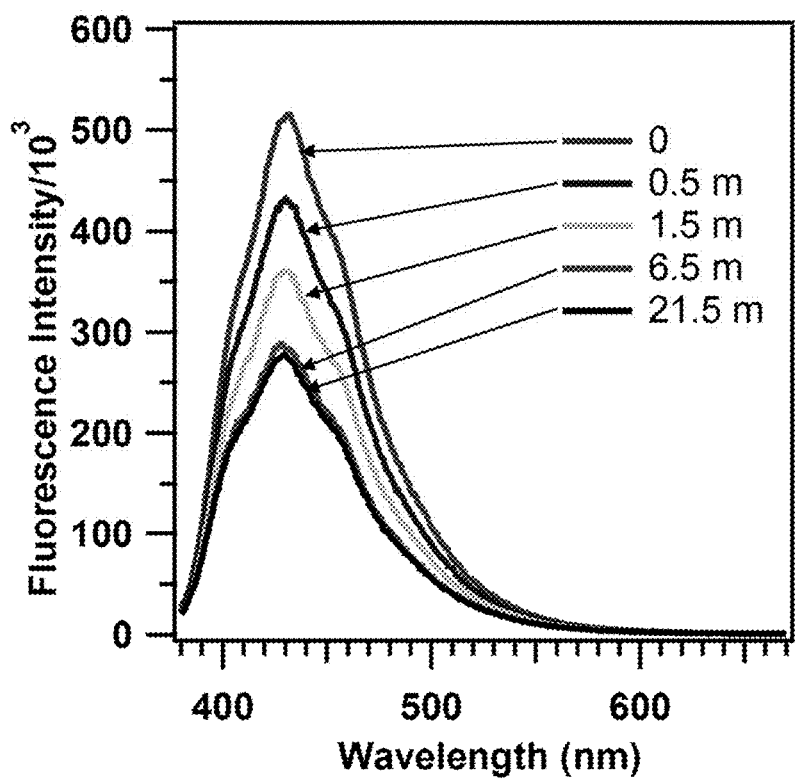
FIG. 40. Representative raw fluorescence data of examples of TPV films exposed to RDX vapors from extracted RDX 4 placed in a darkened vacuum chamber, sample 3, 72 hours.

First, the fluorescence response of TPV films polymerized for 24 hours, 48 hours, and 72 hours to RDX introduced from solution was evaluated. RDX was extracted from commercial samples of the compound adsorbed onto sand that are used to train bomb-detecting canines. RDX was crystallized twice and stored at low temperature and protected from light prior to performing quenching experiments. $^1$H NMR of the twice-crystallized material indicated the expected resonance for RDX, along with a small amount of octahydro-1,3,5,7-tetranitro-1,3,5,7-tetrazocine (HMX) (FIG. 5b). HMX is a cyclic tetranitramine explosive related to RDX and has an even lower vapor pressure. A RDX stock solution (1 mg/mL dissolved in 1:1 v/v $CH_3CN$:MeOH) was prepared and diluted further to deliver picogram quantities of RDX to the films. After recording the film's initial fluorescence, the RDX solution was introduced and the solvent was evaporated under high vacuum. The film's fluorescence was again recorded. This procedure was repeated to introduce cumulative RDX dosages between 0-18765 pg and reproduced in triplicate for films grown for 24 hours, 48 hours, and 72 hours. Each TPV film showed reduced emission intensity when exposed to even 1 pg of RDX, and this response saturated at cumulatives dose of ~1800 pg. The films exhibited increased quenching response as a function of their reaction time. The 72 hours films showed 51±15% quenching when exposed to 25 pg RDX and saturated at 71±9% at larger doses. In contrast, the 48 hours films showed 24±6% when exposed to 25 pg RDX and saturated at 53±10% while the 24 hours films showed only 9±4% when exposed to 25 pg RDX and saturated at 14±9% (FIGS. 4a-4d). Although each film responded to low picogram quantities of RDX, this response is nonlinear at this dosage. Nonlinear, reproducible quenching responses were reproducibly observed for 72 hours films exposed to dosages of 0-2900 femtograms (FIG. 29) and 0-1700 attograms of RDX (FIG. 30). Upon reducing the RDX dosage still further, 72 hours films exhibited an approximately linear quenching response over the 1-30 attogram range (FIG. 4e), a promising level of sensitivity for detecting RDX from the vapor phase. An important control experiment was performed in which the fluorescence response of TPV films grown for 72 hours were measured after sequential introduction and evaporation the same 1:1 v/v $CH_3CN$:MeOH mixture used to prepare the dilute RDX solutions. It was noted that residual amounts of these solvents induce an increase in TPV fluorescence intensity if they are not evaporated completely (FIG. 4f). Therefore, quenching observed in response to the RDX-containing solution cannot be attributed to residual solvent or the presence of trace impurities found in these solvents. It was hypothesized that the increased response of the 72 hours films compared to those grown for shorter times derives from longer exciton diffusion lengths that arise from the increased degree of polymerization of the network.

Given RDX's poor photostability, the response of the 72 hours TPV film to partially degraded samples of RDX was evaluated to determine whether the polymer responds to RDX itself or its degradation products. RDX photolysis produces a complex mixture of products: hexahydro-1-nitroso-3,5-dinitro-1,3,5-triazine (MNX), hexahydro-1,3,5-trinitroso-1,3,5-triazine (TNX), 1,3-dinitro-1,2,3,4-tetrahydro-1,3,5-triazine (MUX), 1,3,5-triazine (TUX) and perhaps others, any of which might quench the fluorescence of the TPV network (FIG. 5a). To assess this possibility, a solution of recrystallized RDX (10 mg/mL in 1:1 v/v $CD_3CN$:$CD_3OD$) was photolyzed for 88 hours using a hand-held UV lamp. $^1$H NMR analysis of the solution clearly indicated significant degradation, along with ~42% residual RDX (FIG. 5b). This solution was diluted with 1:1 v/v $CH_3CN$:$CH_3OH$ to a 10 pg/mL concentration based on the initial concentration of crystallized RDX. A 72 hours film exposed to 25 pg of RDX from this solution showed 26% quenching and saturated at 46% (FIG. 5c). The reduced saturated quenching response, despite the photolyzed solution containing significant amounts of RDX, might indicate that the photodegradation products interact with the polymer competitively with RDX, but do not quench its fluorescence. A similar reduction in quenching efficiency was observed when commercial RDX standard solutions, which had been stored for prolonged periods, were employed. The films showed 27±13% quenching on exposure to 25 pg and saturated at 53±14% (FIG. 5c). These observations suggest that TPV films respond to RDX itself and not its degradation products.

Figure 41:
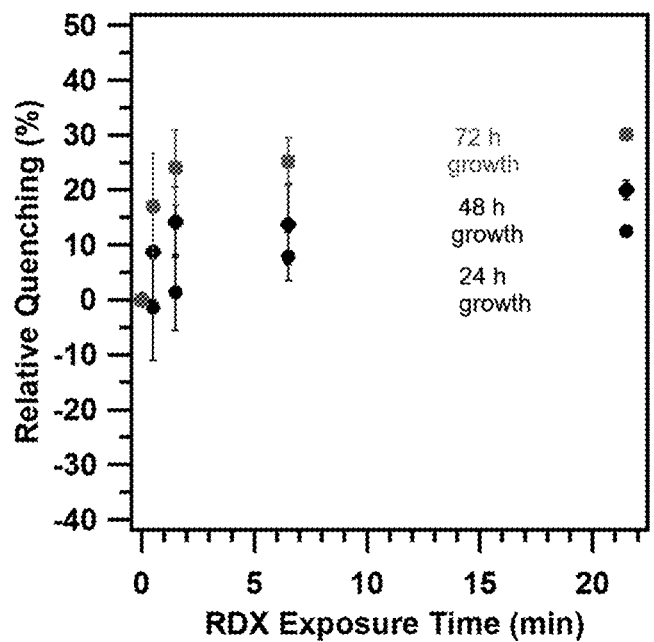
FIG. 41. Representative response of examples of 24 hours, 48 hours, 72 hours films to RDX vapor directly from K-9 training aid.
Figure 42:
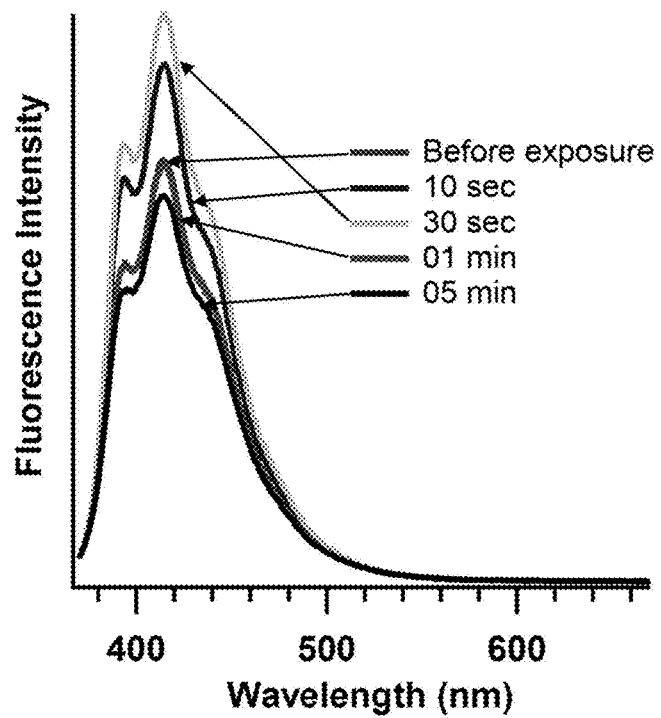
FIG. 42. Representative fluorescence control experiment. Exposure of 1 to RDX.
Figure 43:
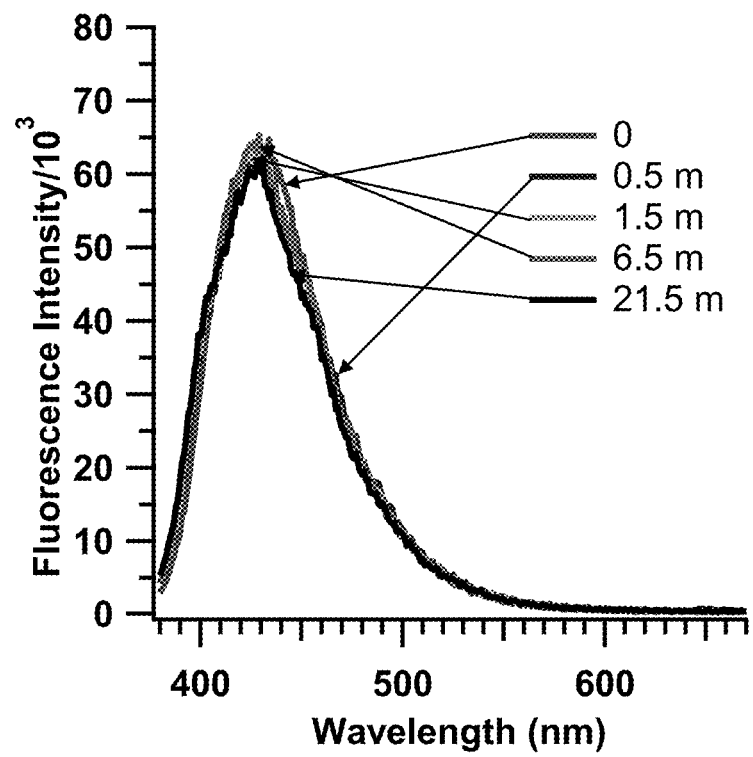
FIG. 43. Representative fluorescence control experiment. Exposure of a TPV film in $CH_2Cl_2$ to ethanol—Sample 1.
Figure 44:
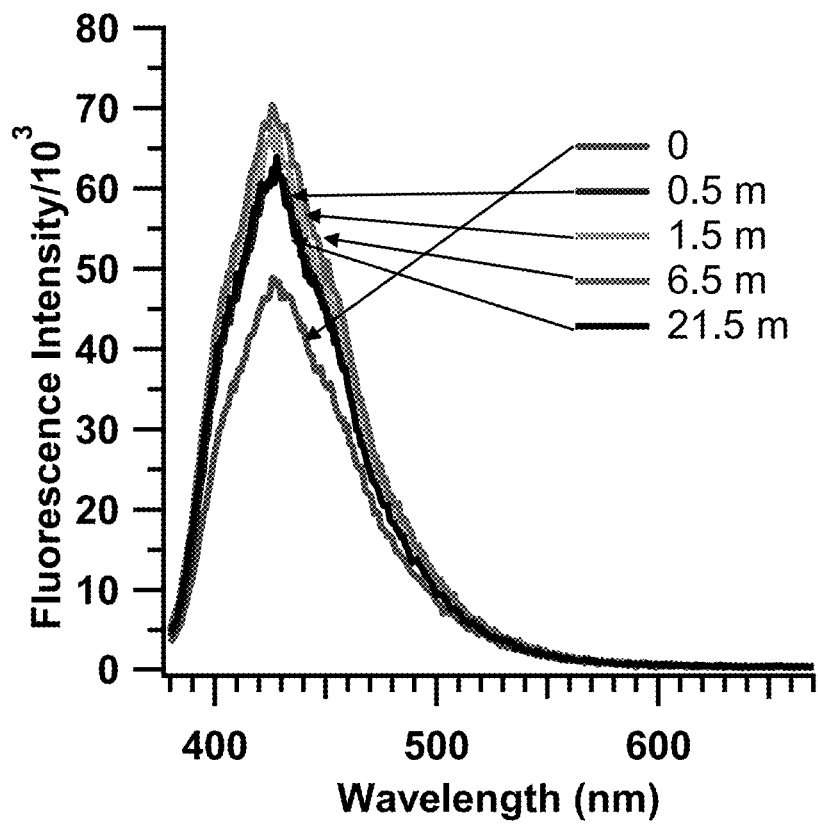
FIG. 44. Representative fluorescence control experiment. Exposure of a TPV film in $CH_2Cl_2$ to ethanol—Sample 2.
Figure 45:
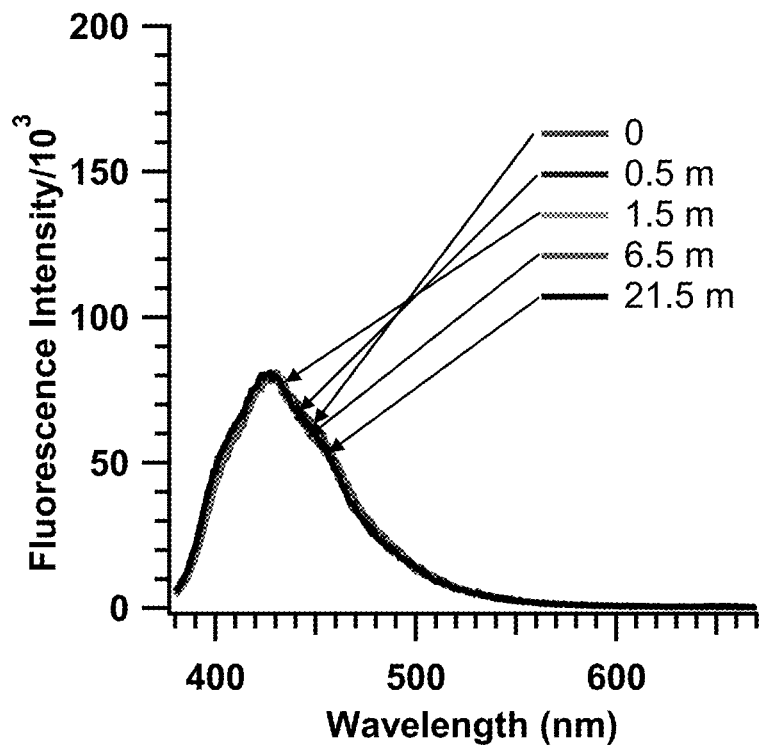
FIG. 45. Representative fluorescence control experiment. Exposure of a TPV film in $CH_2Cl_2$ to ethanol—Sample 3.
Figure 46:
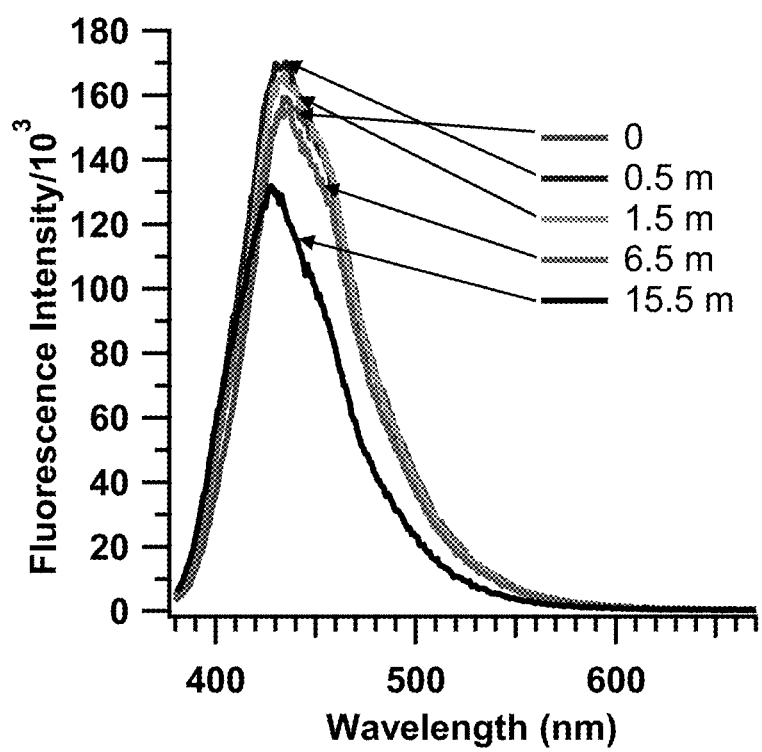
FIG. 46. Representative fluorescence control experiment. Exposure of TPV film in $CH_2Cl_2$ to lipstick—Sample 1.
Figure 47:
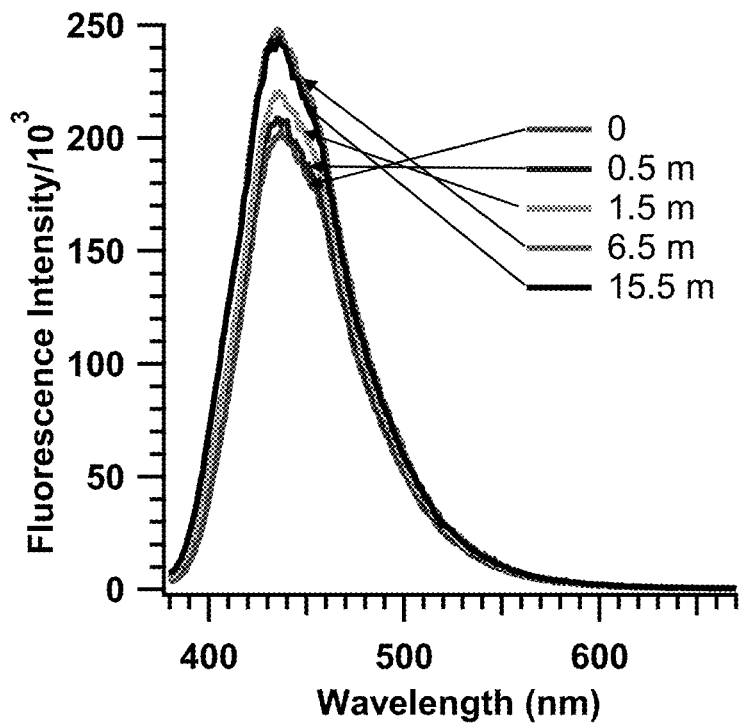
FIG. 47. Representative fluorescence control experiment. Exposure of a TPV film in $CH_2Cl_2$ to lipstick—Sample 2.
Figure 48:
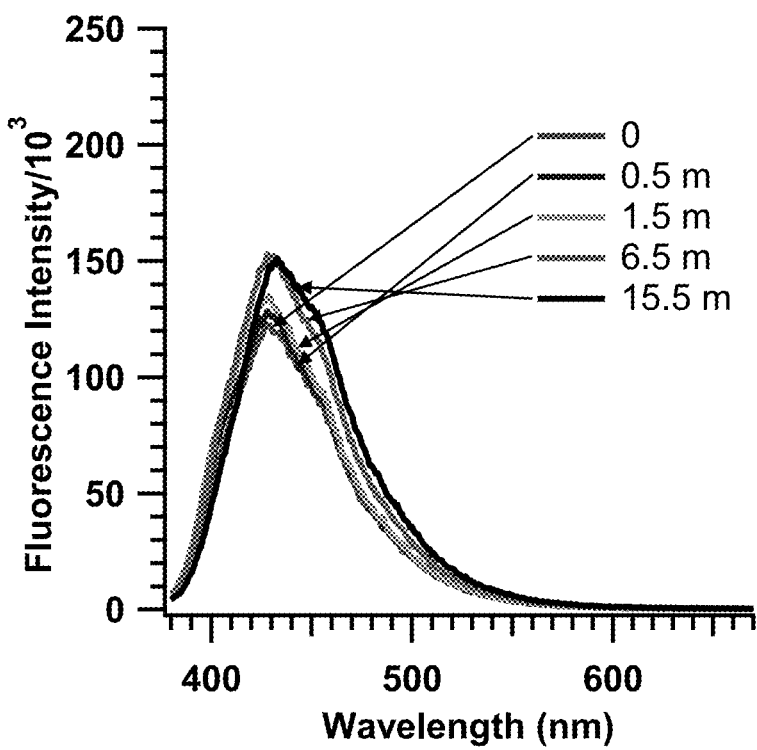
FIG. 48. Representative fluorescence control experiment. Exposure of a TPV film in $CH_2Cl_2$ to lipstick—Sample 3.
Figure 49:
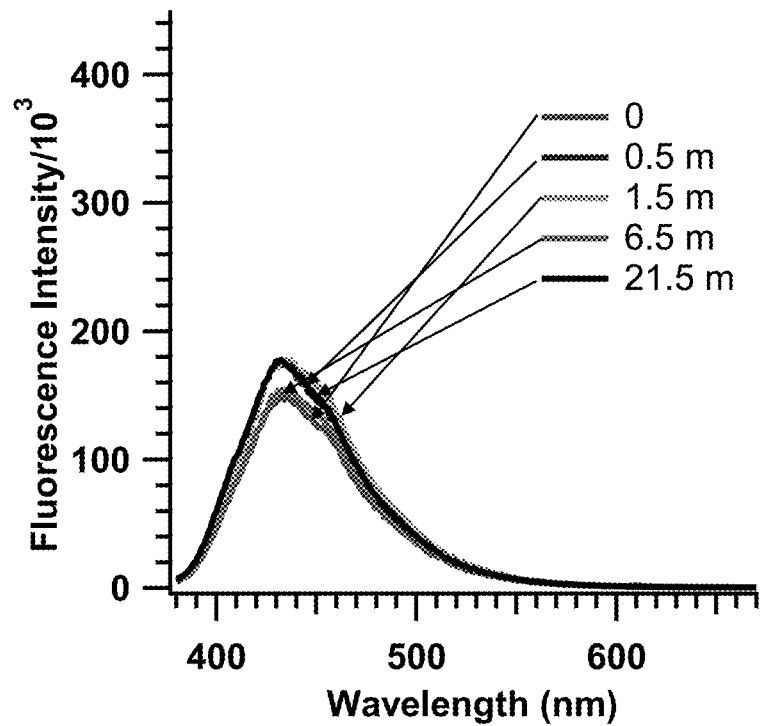
FIG. 49. Representative fluorescence control experiment. Exposure of a TPV film in $CH_2Cl_2$ to sunscreen—Sample 1.
Figure 50:
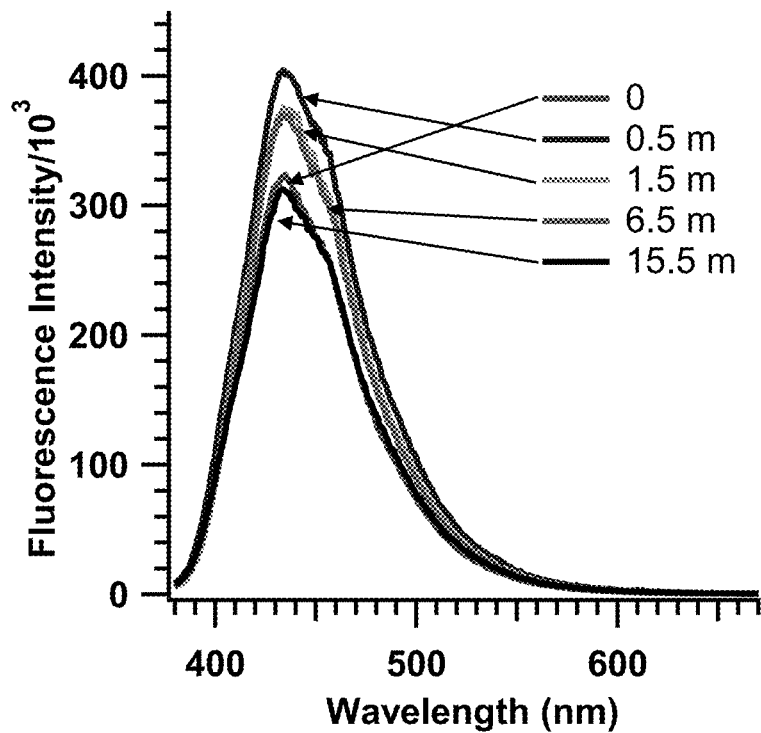
FIG. 50. Representative fluorescence control experiment. Exposure of a TPV film in $CH_2Cl_2$ to sunscreen—Sample 2.
Figure 51:
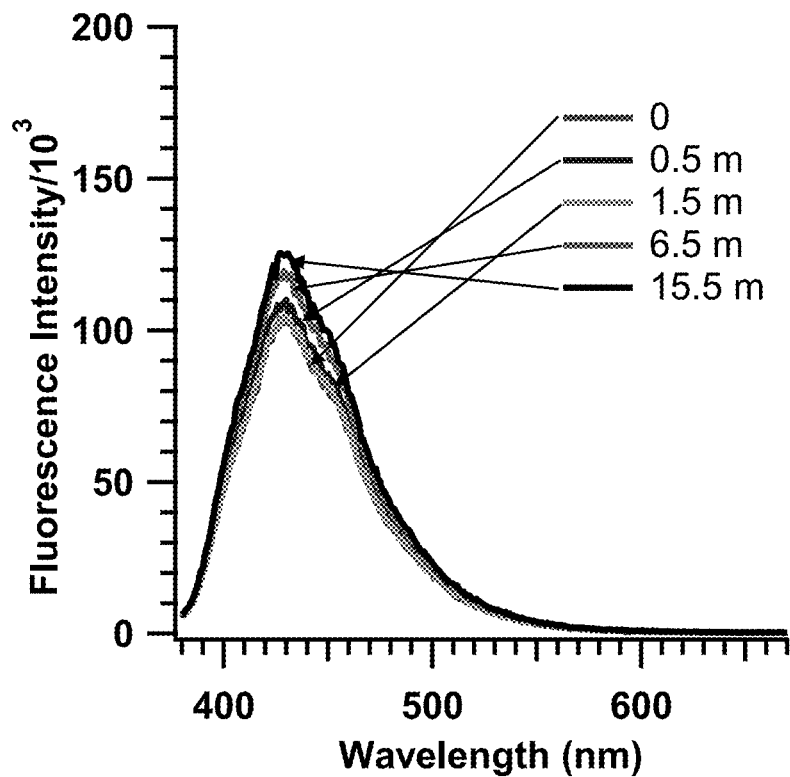
FIG. 51. Representative fluorescence control experiment. Exposure of a TPV film in $CH_2Cl_2$ to sunscreen—Sample 3.
Figure 52:
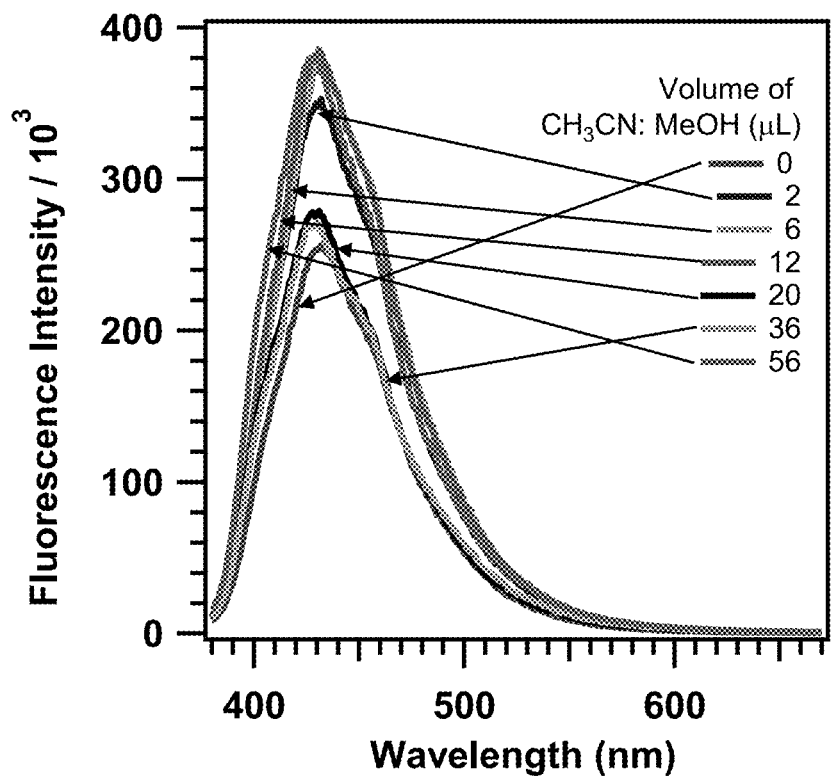
FIG. 52. Representative fluorescence control experiment. Exposure of a 72 hours TPV film in $CH_2Cl_2$ to $CH_3CN$:MeOH (1:1) solution-Sample 1.
Figure 53:
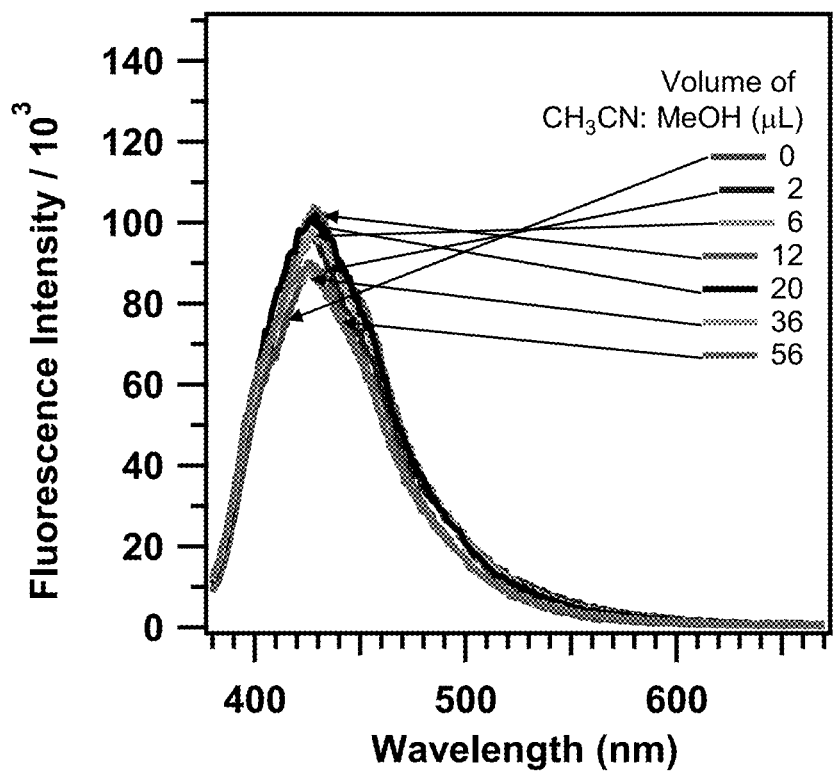
FIG. 53. Representative fluorescence control experiment. Exposure of a TPV film in $CH_2Cl_2$ to $CH_3CN$:MeOH (1:1) solution—Sample 2.
Figure 54:
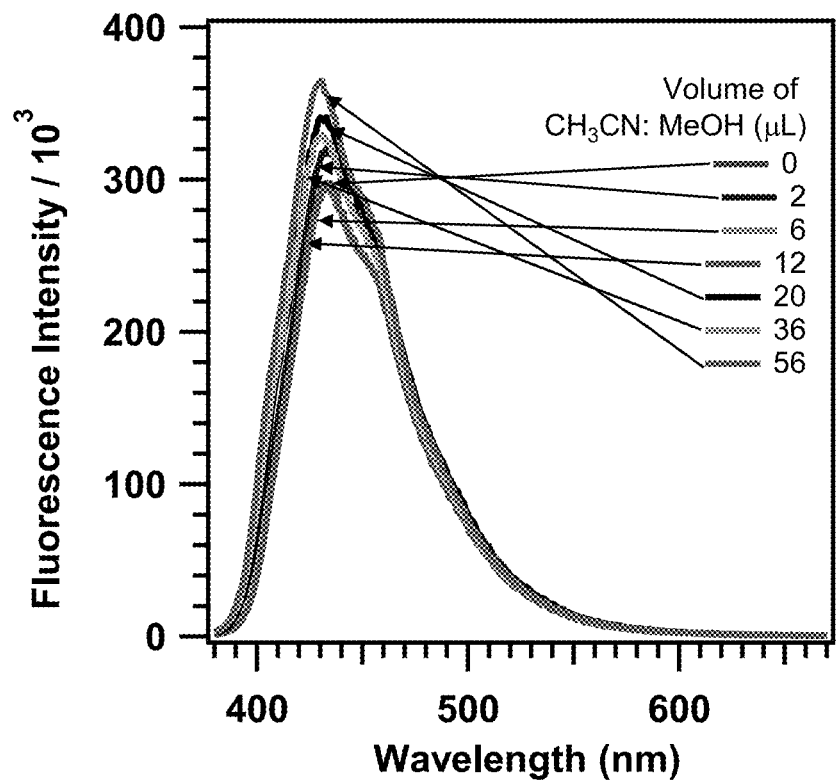
FIG. 54. Representative fluorescence control experiment. Exposure of TPV film in $CH_2Cl_2$ to $CH_3CN$:MeOH (1:1) solution—Sample 3.
Figure 55:
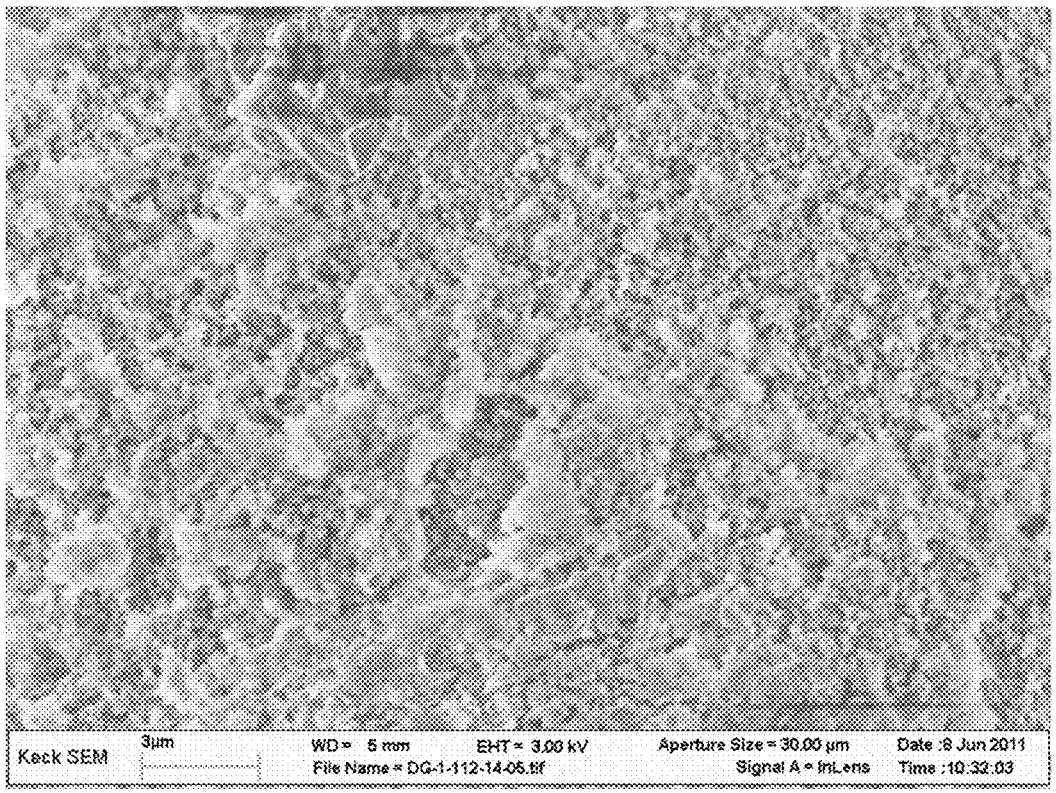
FIG. 55. Representative SEM of a TPV powder.
Figure 56:
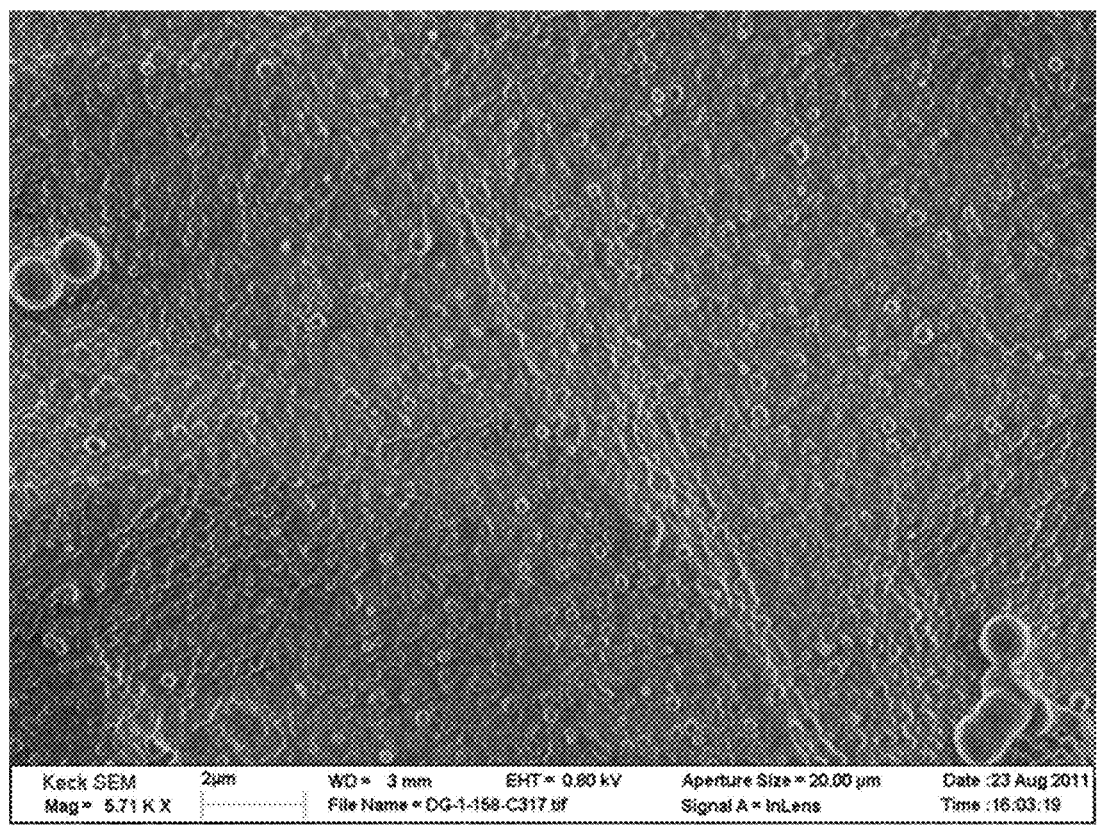
FIG. 56. Representative SEM of a TPV thin film on $SiO_2$.
Figure 60:
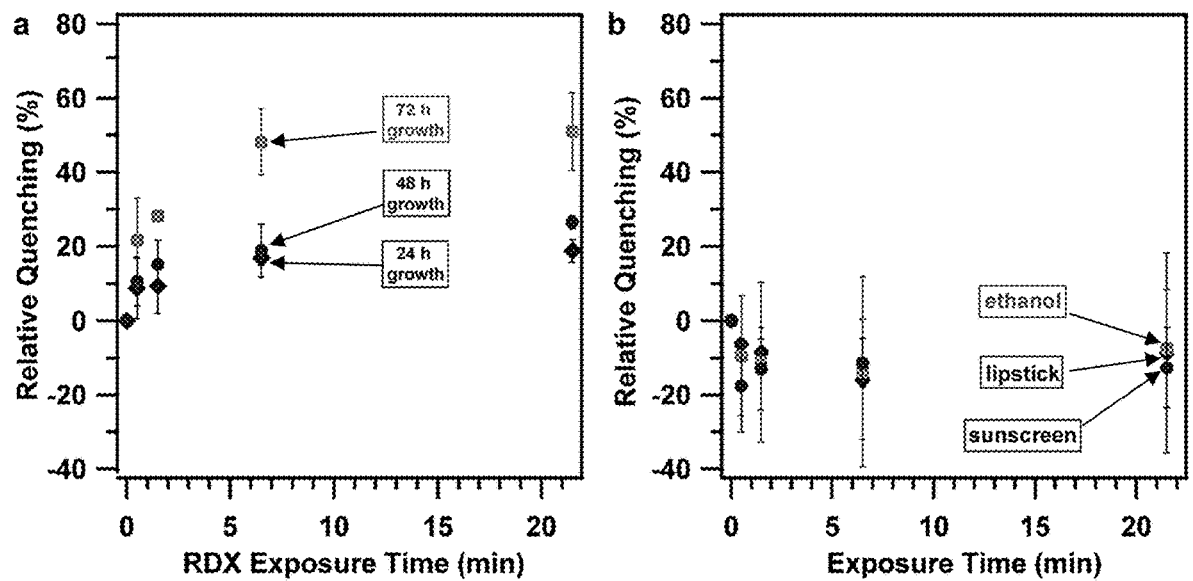
FIG. 60. Representative detection of RDX vapor, a) Response of examples of TPV films to RDX vapor exposure, b) Response of examples of 72 hours TPV films to outgassed vapors from EtOH, and household lipstick and sunscreen.

Counter terrorism applications will greatly benefit from directly detecting RDX vapor without the need for preconcentration strategies. Each of the TPV films was evaluated in this context by storing the film in the headspace of a closed glass vessel containing a sample of crystallized RDX at ambient temperature and pressure. Prior to performing the quenching experiments, the vessel containing the RDX was placed under high vacuum for 6 hours at 25° C. while protected from light exposure to minimize the presence of other volatile compounds. The fluorescence of 24 hours, 48 hours, and 72 hours films was recorded in triplicate as a function of exposure time. As before, the 72 hours film showed both the fastest and largest response, with 22±11% quenching within 30 s, which saturated at 50±11% at longer exposure times. The 48 hours and 24 hours films showed qualitatively similar quenching behavior, but with a reduced response (FIG. 60a). Also, the response of the films was evaluated directly to the canine training aids, which contain RDX, presumably alongside its degradation products. Similar, albeit reduced responses were observed (FIG. 41), which are consistent with our solution RDX degradation study. Films grown for 72 hours were subjected to vapors of compounds or household items typically encountered in airport security environments: EtOH, lipstick, and sunscreen (FIG. 60b). None of these compound mixtures quenched the fluorescence of the TPV films, which instead showed increased fluorescence intensity in each case. This response is similar to that observed when residual volatile solvents remain in the films. Electron-rich aromatics have also been shown to increase the fluorescence intensity of conjugated microporous polymers capable of sensing DNT. The reduced potential for false positives and high sensitivity to RDX make TPV polymers a potential material for commercial sensing technology. To our knowledge, these findings represent the first demonstration of RDX vapor detection by a conjugated polymer.

A conjugated polymer network was synthesized whose fluorescence is quenched by RDX vapor. Analysis of the insoluble powder form of the polymer confirmed that the olefin metathesis reactions employed in its synthesis provided the anticipated chemical linkages. Thin films of these polymers were grown on fused $SiO_2$ substrates, and UV/Vis absorption spectroscopy of these films suggested increased conversion of their reactive groups over 72 hours. The fluorescence of these films decreased upon exposure to RDX, introduced either from solution or from the vapor phase, and depended strongly on the film's growth time. Degradation studies also suggest that the films respond to RDX itself and retain most of their sensitivity to partially degraded samples. These promising findings warrant future inquiry into conjugated polymer networks, as their performance might be improved by achieving long-range order, high surface area, and improved control over film thickness.

Methods. General procedure for preparation of TPV powder. Monomer 1 (0.080 mg, 0.208 mmol) and Grubbs $2^{nd}$ Generation catalyst (0.011 g, 0.013 mmol) were added to a Kimble/Kontes trimmed-stem KIMAX-51 borosilicate glass ampoule (5 mL, body length 37 mm, outer diameter 16.75 mm, neck length 51 mm). $CH_2Cl_2$ (1.56 mL) was then added to the ampoule. Once the solids were completely dissolved, the ampoule was flash frozen in liquid N2 and the ampoule neck was flame-sealed in air using a propane torch, reducing the total length by 20-30 mm. Upon warming to room temperature, the suspension was immersed in an oil bath at 45° C. and left undisturbed for the desired reaction time. The reaction was cooled to room temperature, the ampoule was broken at the scored neck, and the dark solution was passed through a Hirsch filter funnel with a qualitative filter paper (medium porosity) and vacuum filtered. The resulting solid TPV obtained was washed with $CH_2Cl_2$ and dried under vacuum.

General procedure for preparation of TPV films. Monomer 1 (0.08 mg, 0.208 mmol), Grubbs 2nd Generation catalyst (0.011 g, 0.013 mmol) were added to a 15 mL cylindrical pressure vessel and dissolved in $CH_2Cl_2$ (1.56 mL), after which the fused $SiO_2$ substrate was added to the vessel. The sealed vessel was heated in a sand bath at 45° C. for 24 hours, 48 hours or 72 hours. The vessel was cooled to room temperature and the resulting grayish black powder was recovered by filtration and dried under vacuum. The fused $SiO_2$ substrate was submerged in $CH_2Cl_2$ for 30 min, stirred occasionally, then washed with fresh $CH_2Cl_2$ and finally dried in air.

Measurement of fluorescence response of TPV film to RDX solution in 1:1 v/v $CH_3CN:MeOH$. The fluorescence of TPV film was measured with a Horiba Jobin Yvon Fluorolog-3 fluorescence spectrophotometer equipped with a 450 W Xe lamp. A known quantity of RDX solution was then added to the film. The film was evacuated for 6 min under high vacuum to remove the solvents. The fluorescence intensity of TPV film was then recorded. This procedure was repeated for incremental values of RDX concentration starting at 1 pg and ending at a cumulative value of 18765 pg of RDX.

Measurement of fluorescence response of TPV film to RDX vapor. The fluorescence of TPV film was measured after preparation. The TPV film was exposed to RDX vapors from the crystallized RDX, placed in a vacuum chamber for 30 s. The TPV film was removed from the chamber and its fluorescence intensity was measured. This procedure was repeated for a cumulative exposure time of 21.5 min.

Materials. Unless otherwise stated, all reagents were purchased from commercial sources and used without purification. Grubbs 2nd generation catalyst was purchased from Sigma-Aldrich. THF, $CH_2Cl_2$, toluene and ethanol were purchased from commercial sources and purified using a custom-built activated alumina-based solvent purification system. Other solvents were purchased from commercial sources and used without purification. The commercial RDX standard solution was purchased from AccuStandard (1 mg/mL RDX in 1:1 v/v MeOH:CH 3 CN TRUESCENT® non-explosive RDX K-9 training aid (Signature Science LLC, Austin, TX) was used to isolate pure RDX and for RDX vapor sensing experiments. NEUTROGENA® wet skin SPF 45+ and MAYBELLIINE®, 206700 (625) Color Sensational lipstick were used for control experiments.

Instrumentation. NMR spectra were recorded on a Varian INOVA 400 MHz spectrometer using a $^1H/X$ Z-PFG probe with a 20 Hz sample spin rate. Gas chromatography/electron impact mass spectrometry was performed on an AGILENT® 6890N Network GC System with a JEOL JMS-GCmate II Mass Spectrometer (magnetic sector) using a gradient oven temperature from 60° C. to 270° C. over 30 min.

Fourier Transform Infrared Spectroscopy was performed using a Thermo Nicolet iS10 FT-IR spectrometer with a diamond ATR attachment and the spectra are uncorrected. Fourier Transform Infrared Spectroscopy on films were performed using a Bruker HYPERION® FT-IR spectrometer & microscope and are also uncorrected.

UV/Vis/NIR absorbance spectroscopy of powder samples was performed on a Cary 5000 spectrophotometer using a praying mantis diffuse reflectance accessory. The background was recorded using potassium iodide ground in a mortar and pestle. Transmission mode spectra were recorded of films grown on $SiO_2$ substrates (~1.5 cm²). The background was recorded using a similar $SiO_2$ substrate without the film.

Powder X-ray diffraction (PXRD) was performed on a Rigaku SmartLab X-Ray diffractometer in reflectance parallel beam/parallel slit alignment geometry. The measurement employed Cu Kα line focused radiation at 1760 W (40 kV, 44 mA) power and a Ge crystal detector fitted with a 1.0 mm radiation entrance slit. Samples were mounted on zero-background sample holders by dropping powders from a wide-blade spatula and then leveling the sample surface with a glass microscope slide. No sample grinding or sieving was used prior to analysis. Samples were observed using a 0.02° 2θ step scan from 2.0-34.0° at a scan speed of 5° per minute.

Photoemission and excitation experiments were performed on a Horiba Jobin Yvon Fluorolog-3 fluorescence spectrophotometer equipped with a 450 W Xe lamp, double excitation and double emission monochromators, a digital photon-counting photomultiplier, and a secondary InGaAs detector for the NIR range. Correction for variations in lamp intensity over time and wavelength was achieved with a solid-state silicon photodiode as the reference. The spectra were further corrected for variations in photomultiplier response over wavelength and for the path difference between the sample and the reference by multiplication with emission correction curves generated on the instrument. Emission from films on $SiO_2$ was observed using a front face detection accessory.

Scanning electron microscopy (SEM) was performed on a LEO 1550 FESEM. Materials were deposited onto a sticky carbon surface on a flat aluminum platform sample holder. No metal sputtering of the sample was necessary. SEM on some samples were performed on a LEO 1550 FESEM at 0.80 KeV. Materials were deposited onto a sticky carbon surface on a flat aluminum platform sample holder and vacuum-degassed at 65° C. for 1 hr.

Surface area measurements were conducted on a MICROMERITICS® ASAP 2020 Accelerated Surface Area and Porosimetry Analyzer using ca. 30 mg samples degassed at 80° C. for approximately 12 hours. N2 isotherms were generated by incremental exposure to ultra high purity N2 up to ca. 1 atm over 24-hour periods in a liquid nitrogen (77K) bath, and surface parameters were determined using Langmuir, BET and BJH adsorption models included in the instrument software (MICROMERITICS® ASAP 2020 V1.05).

X-ray photo electron spectroscopy measurements of thin films on $SiO_2$ were recorded on a Surface Science Instruments (SSI) model SSX-100 which utilizes monochromated Aluminum K-alpha x-rays (1486.6 eV) to strike a sample surface.

Synthetic Procedure. Synthesis of 1,3,5-tri(4-vinylphenyl)-benzene 1.

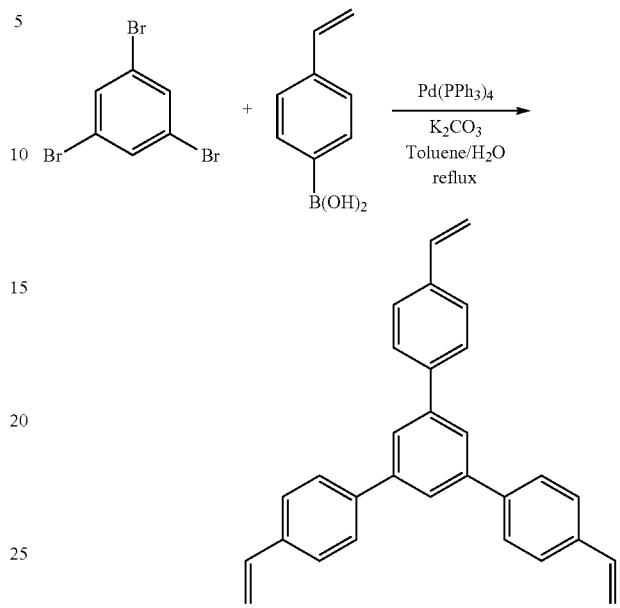

1,3,5-tribromobenzene (2.00 g, 6.35 mmol), 4-vinyl boronic acid (5.62 g, 38.1 mmol), and $K_2CO_3$ (5.27 g, 38.1 mmol) were added to a dry 250 mL 3-neck round-bottom flask, under a $N_2$ atmosphere. Toluene (24 mL) and $H_2O$ (4 mL) were added to the flask. The reaction mixture was degassed through freeze-pump-thaw cycles. $Pd(PPh_3)_4$ (0.35 g, 0.381 mmol) was added to the frozen solution and the reaction mixture was degassed through freeze-pump-thaw cycles. The reaction mixture is heated to reflux for 12 hours, and was monitored by TLC (10% EtOAc/Hexanes). Once complete the reaction mixture was filtered through celite and the solvent was removed under vacuum. The crude orange solid obtained was dissolved in $CHCl_3$ (10 mL) and triturated with MeOH (50 mL), and recovered by filtration. (2.21 g, 91%) was obtained as a grey solid. $^1$H NMR (400 MHz, $CDCl_3$, 298 K) δ 7.79 (s, central Ar—H, 3H), 7.68 (d, J=8 Hz, vinyl aryl —H, 6H), 7.52 (d, J=8 Hz, vinyl-aryl —H 6H), 6.78 (dd, J=17 Hz, 11 Hz, 2- vinyl, 3H), 5.83 (dd, J=17 Hz, ~1 Hz, 1-vinyl, 3H), 5.30 (dd, J=11 Hz, ~1 Hz, IV-vinyl, 3H). $^{13}$C NMR (100 MHz, $CDCl_3$, 298 K) δ 142.1, 140.6, 137.1, 136.5, 127.6, 126.9, 125.0, 114.3. FT-IR (ATR) 2918, 1627, 1564, 1510, 1441, 1389, 1293, 1206, 1118, 1013, 987, 905, 832, 746, 699. HRMS: EI-Calculated: 384.18780 Measured: 384.18791.

General procedure for polymerization. 1 General procedure for preparation of TPV powder. Monomer 1 (0.080 mg, 0.208 mmol) and Grubbs 2nd Generation catalyst (0.011 g, 0.013 mmol) were added to a Kimble/Kontes trimmed-stem KIMAX-51 borosilicate glass ampoule (5 mL, body length 37 mm, outer diameter 16.75 mm, neck length 51 mm). $CH_2Cl_2$ (1.56 mL) was then added to the ampoule. Once the solids were completely dissolved, the ampoule was flash frozen in liquid N2 and the ampoule neck was flame-sealed in air using a propane torch, reducing the total length by 20-30 mm. Upon warming to room temperature, the suspension was immersed in an oil bath at 45° C. and left undisturbed for the desired reaction time. The reaction was cooled to room temperature, the ampoule was broken at the scored neck, and the dark solution was passed through a Hirsch filter funnel with a qualitative filter paper (medium porosity) and vacuum filtered. The resulting solid TPV obtained was washed with $CH_2Cl_2$ and dried under vacuum. IR (powder ATR) 3024, 2921, 1191, 1593, 1572, 1510, 1455, 1434, 1393, 1251, 1168, 1125, 1033, 1015, 988, 963, 941, 905, 826, 746, 703, 658.

General procedure for preparation of TPV films. Monomer 1 (0.08 mg, 0.208 mmol), Grubbs $2^{nd}$ Generation catalyst (0.011 g, 0.013 mmol) were added to a 15 mL cylindrical pressure vessel and dissolved in $CH_2Cl_2$ (1.56 mL), after which the fused $SiO_2$ substrate was added to the vessel. The sealed vessel was heated in a sand bath at 45° C. for 24 hours, 48 hours or 72 hours. The vessel was cooled to room temperature and the resulting grayish black powder was recovered by filtration and dried under vacuum. The fused $SiO_2$ substrate was submerged in $CH_2Cl_2$ for 30 m, stirred occasionally, then washed with fresh $CH_2Cl_2$ and finally air dried.

Synthesis of 1,3,5-tris(stilbenyl) benzene 2.

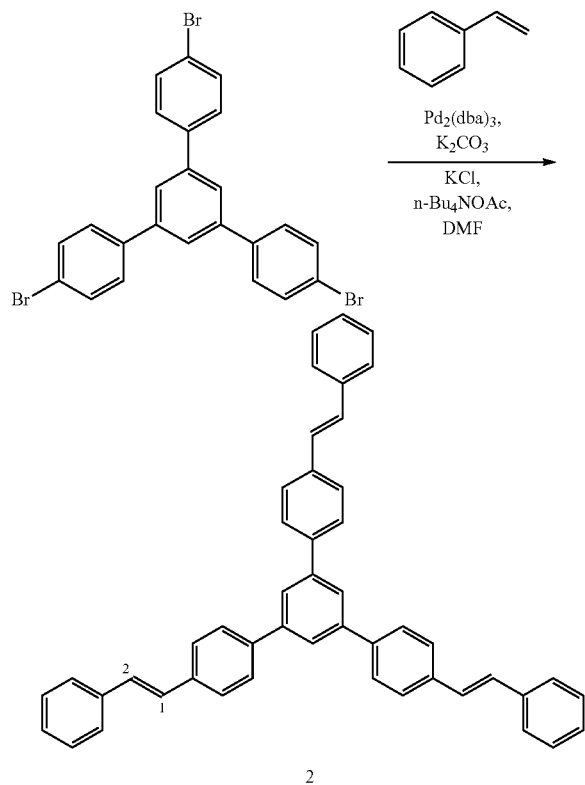

1,3,5-tris(bromophenyl)benzene (0.1 g, 0.184 mmol), styrene (0.172 g, 1.657 mmol), $K_2CO_3$ (0.038 mg, 0.276 mmol), KCl (0.014 g, 0.184 mmol), Pd 2 (dba) 3 (0.016 g, 0.017 mmol), and n-$Bu_4NOAc$ (0.111 mg, 0.368 mmol) were added to a 25 mL dry storage tube, under a $N_2$ atmosphere. DMF (0.6 mL) and styrene (0.172 g) were added to the flask. The reaction mixture was degassed through freeze-pump-thaw cycles. The reaction mixture was heated to 100° C. for 48 hours and was monitored by TLC (10% EtOAc/Hexanes). Once complete the reaction mixture was filtered through celite. The filtrate was extracted with $CH_2Cl_2$ (3×15 mL) and washed with brine solution (3×15 mL). The organic layers were collected, dried with anhydrous $MgSO_4$, and solvent was removed under vacuum. The crude brown solid obtained was run through a silica plug (10% EtOAc/Hexane 20 mL) and the solvent was removed under vacuum. 2 (0.06 g, 54%) was obtained as a grey solid. This compound was previously reported, although its characterization was limited to UV/Vis spectroscopy. The experimental max obtained for 2 matched that described here. Further characterization is provided as follows. $^1$H NMR (400 MHz, $CDCl_3$, 298 K) δ 7.90 (s, central Ar—H, 3H), 7.78 (d, J=8 Hz, 1-vinyl aryl —H, 6H), 7.72 (d, J=8 Hz, 1-vinyl-aryl —H 6H), 7.63 (d, J=7 Hz, 2-vinyl aryl —H, 6H), 7.46 (m, 2-vinyl aryl, 6H), 7.46 (m, 2-vinyl aryl —H, 3H), 7.12 (broad stilbenyl —H, 6H). $^{13}$C NMR (100 MHz, $CDCl_3$, 298 K) δ 142, 140.3, 137.4, 136.8, 129.1, 128.8, 128.3 127.9, 127.7, 127.1, 126.7, 124.9. FT-IR (ATR) 1594, 1510, 1492, 1450, 1393, 1180, 1154, 1072, 1027, 960, 857, 812, 794, 77, 724, 695.

Figure 11:
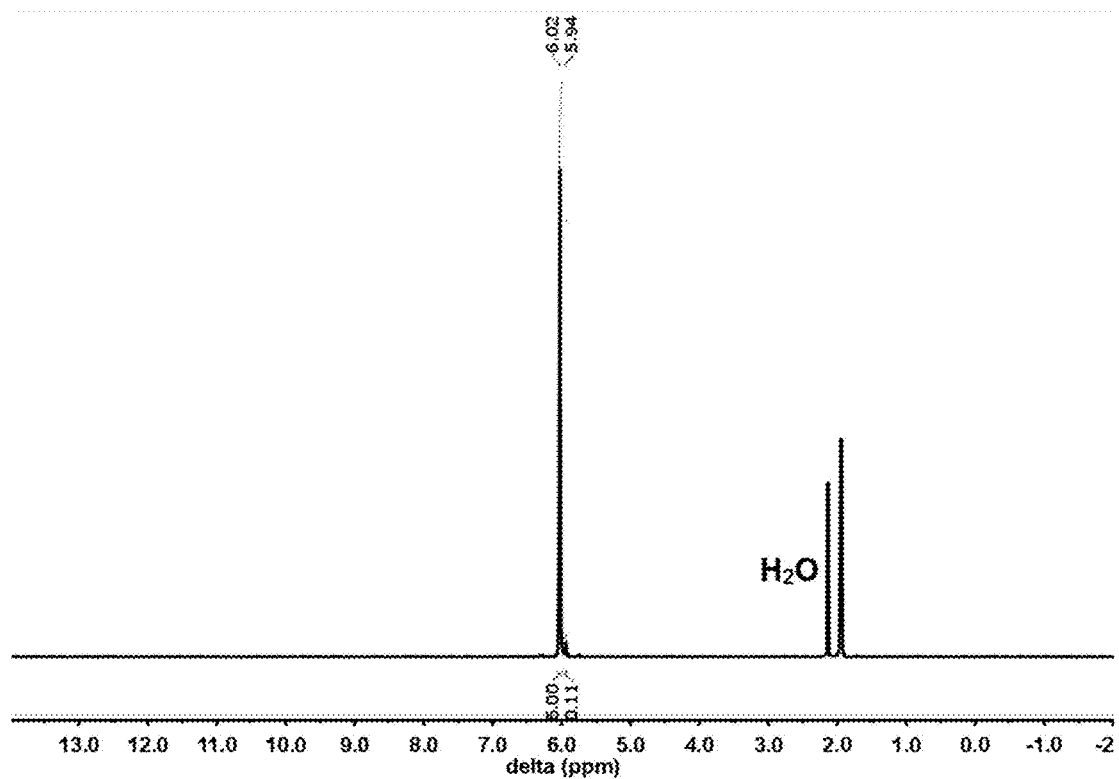
FIG. 11. $^1H$ NMR of twice-crystallized RDX 4 (300 MHz, $CD_3CN$, 298K).
Figure 12:
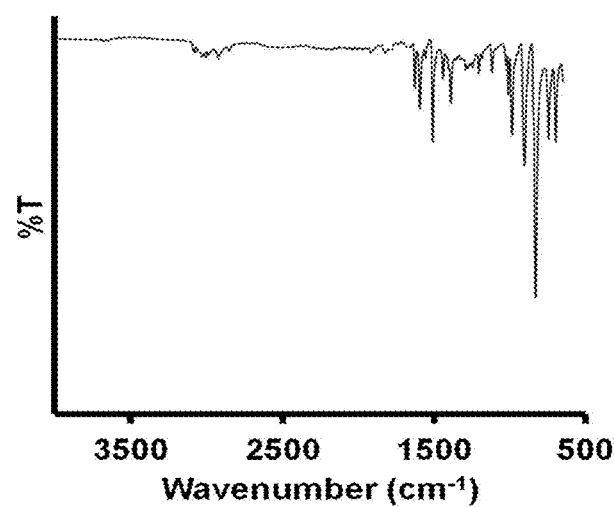
FIG. 12. Representative FT-IR spectra of 1.

Extraction of RDX from K-9 training aid. 5.2 g of training aid sample was suspended in 8 mL $CH_3CN$. After 20 min, the sand was removed by filtration through qualitative filter paper. The filtrate was concentrated to 1 mL, on a rotary evaporator, during which time RDX partially precipitated from the solution. Due to the fact that RDX poses an explosion hazard, the solution was not allowed to fully evaporate. Additional $CH_3CN$ (1 mL) was added to redissolve the solid, after which $CHCl_3$ (4 mL) was added dropwise. $CHCl_3$ addition caused RDX to crystallize from the solution. These crystals were isolated by filtration, redissolved in $CH_3CN$ (2 mL), and crystallized again by adding $CHCl_3$ dropwise. RDX was isolated as a white crystalline solid 4 (0.037 g, 0.167 mmoles), which was divided into ~10 mg portions and stored at −4° C. protected from light. $^1$H NMR analysis of the RDX indicated its identity and purity. A 2% impurity of the nitramine explosive octahydro-1,3,5,7-tetranitro-1,3,5,7-tetrazocine (HMX) was also observed in the spectrum (FIGS. 5b and 11).

Irradiation of RDX. RDX crystals 4 (0.010 g, 0.045 mmoles) were dissolved in 1 mL ($CD_3CN$:$CD_3OD$) in a NMR tube. The solution was irradiated with a hand held UV lamp (SPECTROLINE® Model ENF-260C) for 88 hours. The decomposition of RDX was observed by NMR (FIG. 5b).

TABLE 1

| $I_{358\,nm}/I_{287\,nm}$ ratio to reaction time | |
|---|---|
| $I_{358\,nm}/I_{287\,nm}$ | Reaction time (hours) |
| 0.38 | 0.5 |
| 0.87 | 1 |
| 1.06 | 2 |
| 1.18 | 24-48 |
| Shoulder | 72 |

Fluorescence response to extracted RDX 4 in 1:1 MeOH: $CH_3CN$. FIGS. 20-25 are plots are raw fluorescence data of TPV films exposed to picograms of RDX in 1:1 MeOH: $CH_3CN$. These show a decrease in the fluorescence counts as quantity of RDX in solution is increased in regular increments. The first set of data in each case is shown in FIG. 4.

Figure 26:
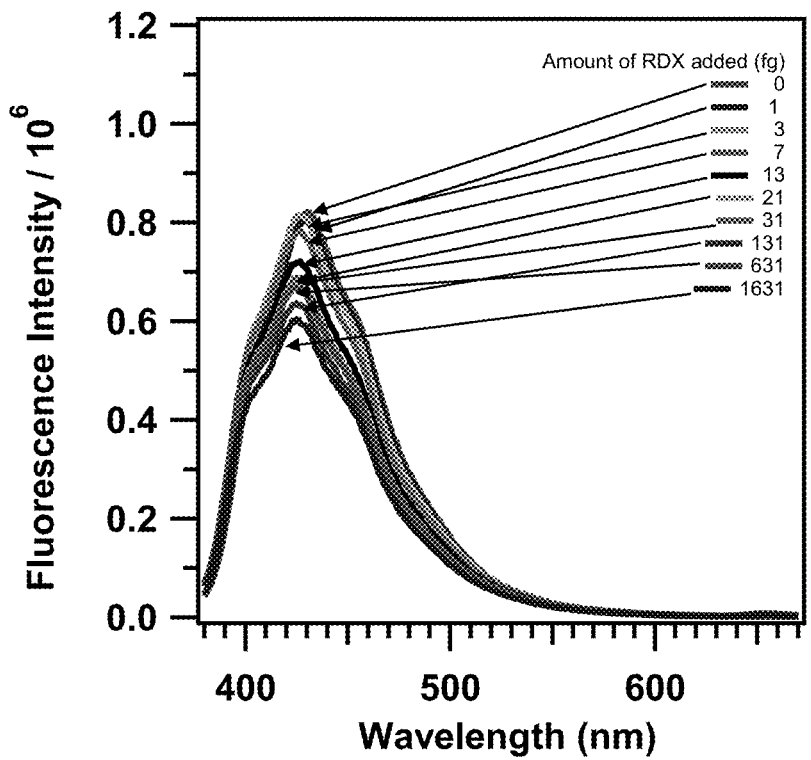
FIG. 26. Representative raw fluorescence data of examples of 72 hours TPV films exposed to attograms of RDX in 1:1 MeOH:$CH_3CN$, sample 1.
Figure 27:
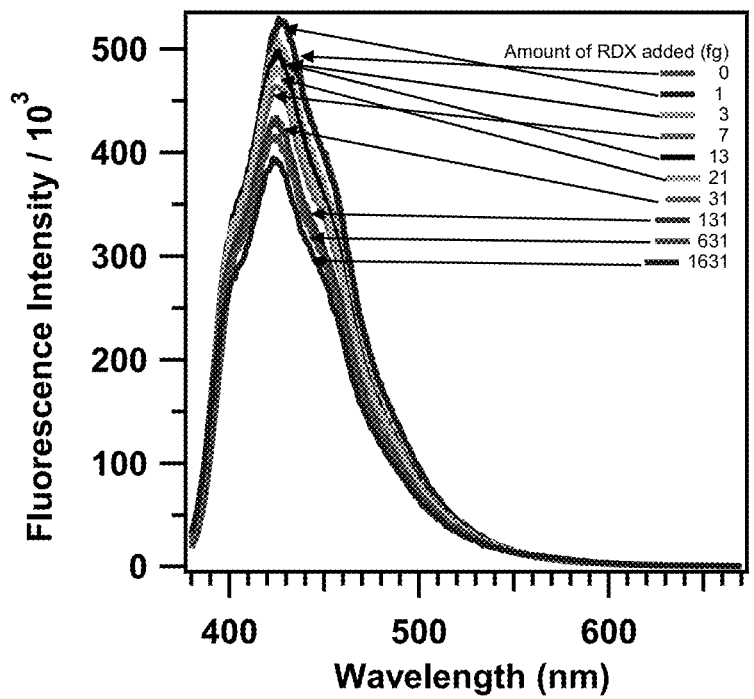
FIG. 27. Representative raw fluorescence data of examples of 72 hours TPV films exposed to attograms of RDX in 1:1 MeOH:$CH_3CN$, sample 2.
Figure 28:
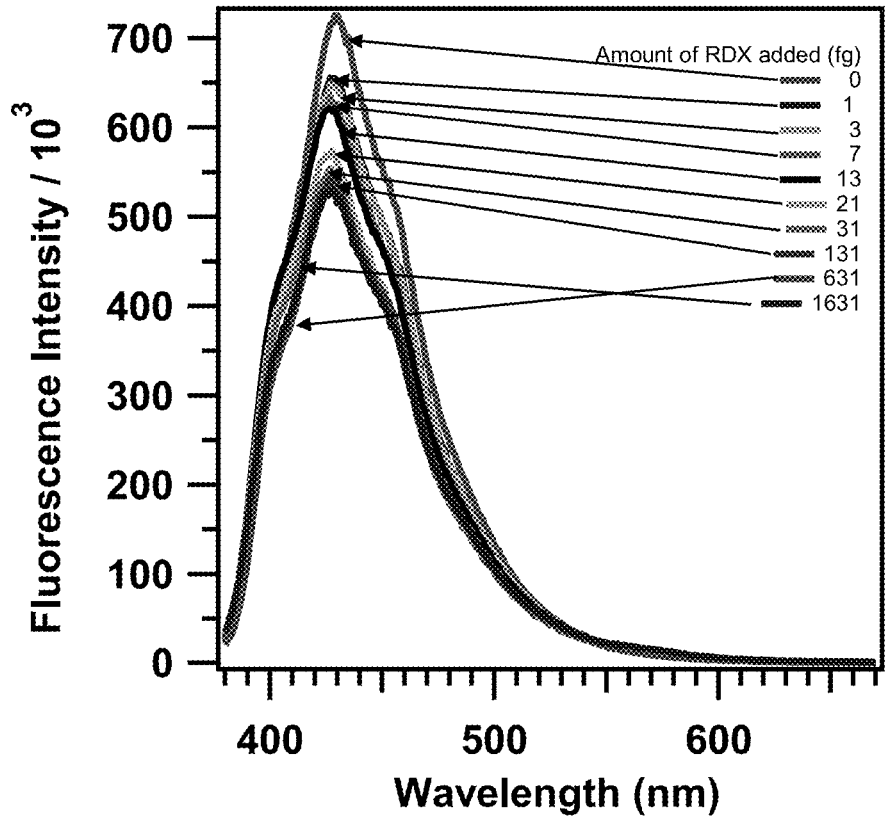
FIG. 28. Representative raw fluorescence data of examples of 72 hours TPV films exposed to attograms of RDX in 1:1 MeOH:$CH_3CN$, sample 3.

FIGS. 26-28 are plots are raw fluorescence data of 72 hours TPV films exposed to attograms of RDX in 1:1 MeOH:$CH_3CN$. These show a decrease in the fluorescence counts as amount of RDX in solution is increased in regular increments.

Exposure to RDX Vapor. FIGS. 32-41 are plots of raw fluorescence data of TPV films exposed to RDX vapors from extracted RDX 4 placed in a darkened vacuum chamber. The chamber was evacuated overnight and then the films were placed in the chamber for analysis.

Fluorescence Control Experiments (FIGS. 42-54). Exposure of 1 to RDX. A drop of ti-1,3,5-(4-vinylphenyl) benzene in o-dichlorbenzene was placed on $SiO_2$. Once the solution dried, the film was exposed to RDX for a particular time period.

EXAMPLE 2

In this example, formation of thin film of a cross-linked polymer network cross-linked to a substrate is demonstrated.

Tris (4-vinylphenyl)benzene (0.040 g, 0.104 mmoles), Grubbs 2nd generation catalyst (0.005 g, 0.006 mmoles) are added to a 15 mL pressure tube with a screw cap. Dry DCM (1.56 mL, 0.07 M) is then added to the tube. A fused $SiO_2$ chip functionalized with allyltrimethoxysilane is gently dropped in to the reaction solution. The pressure tube is sealed with the screw cap and the tube is heated to 45° C. After time "t" the reaction is stopped and the tube is cooled down to room temperature. Then the pressure tube is opened and the fused $SiO_2$ chip is removed from the reaction mixture. The chip is washed with DCM and the solution is sonicated for 15 seconds to remove any powders stuck on the film. The chip is air dried before further experiments.

EXAMPLE 3

In this example, formation of a cross-linked porphyrin network is demonstrated.

Figure 62:
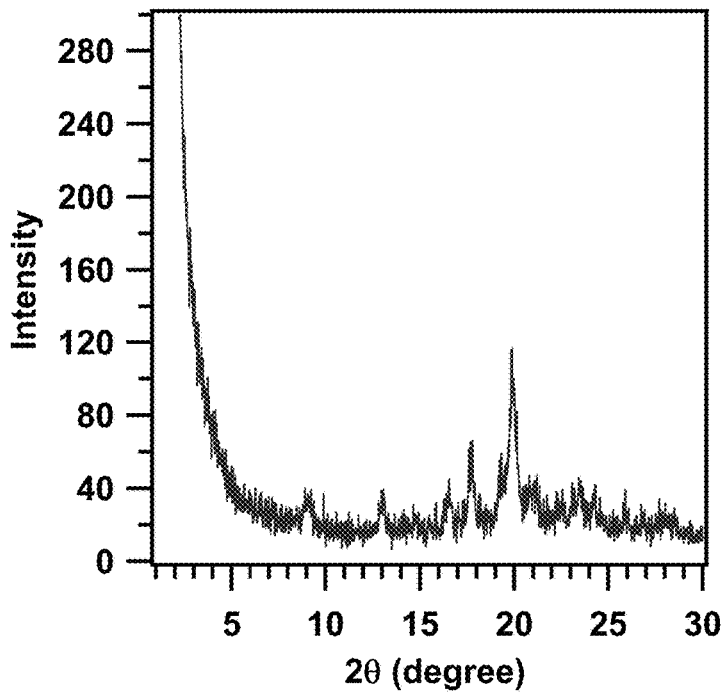
FIG. 62. Powder X ray diffraction of an example of a Porphyrin COF.
Figure 63:
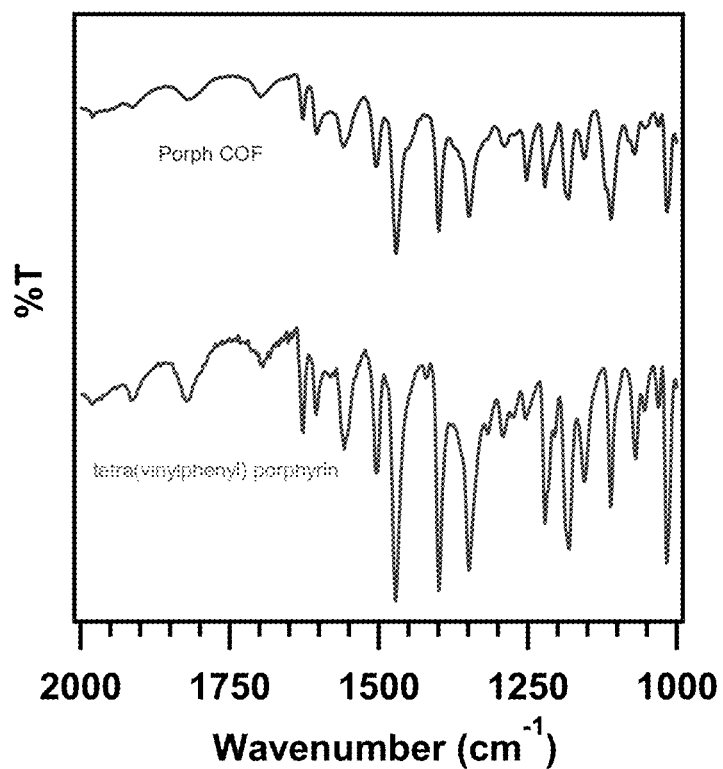
FIG. 63. Infrared spectra of an example of a Porphyrin COF and tetra(vinylphenyl) porphyrin.
Figure 64:
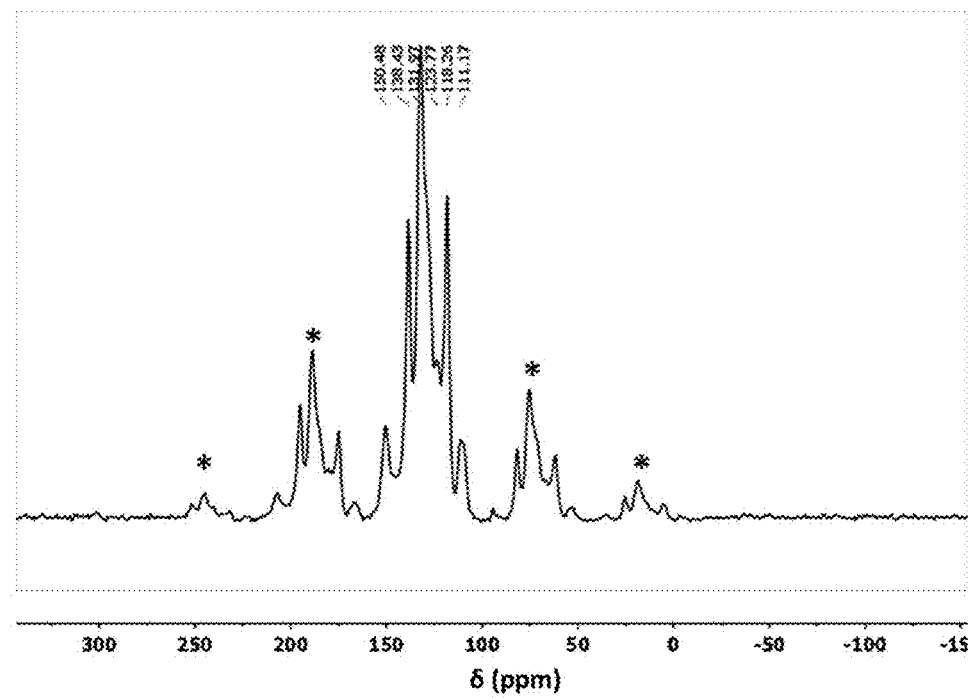
FIG. 64. $^{13}$C-CPMAS NMR spectrum of an example of a Porphyrin-COF.
Figure 65:
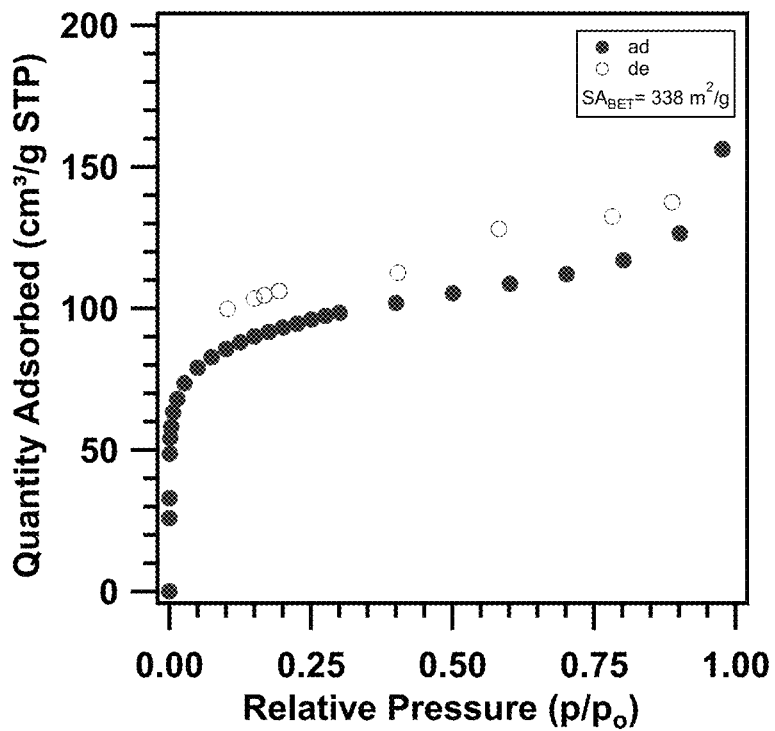
FIG. 65. N2 adsorption isotherm (77 K) of an example of a Porphyrin-COF. Inset: BET Surface Area.
Figure 66:
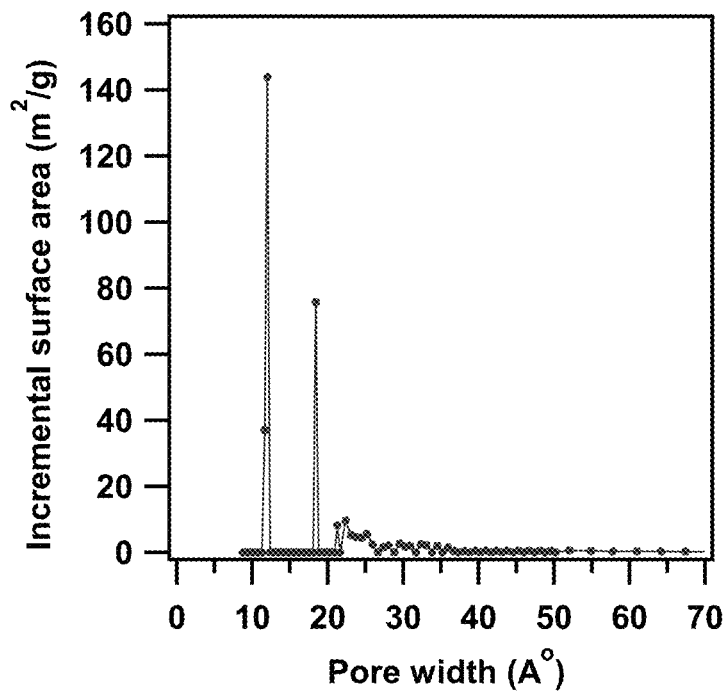
FIG. 66. Pore size distribution of an example of a Porphyrin-COF.
Figure 67:
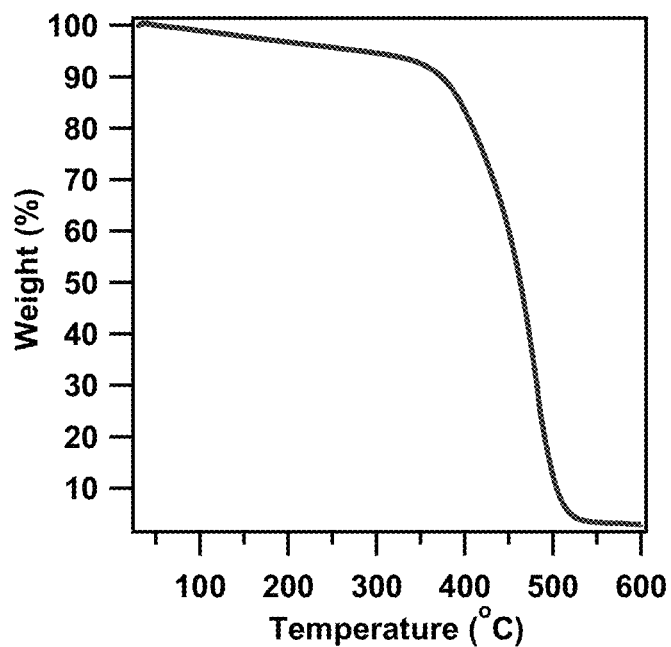
FIG. 67. Thermogravimetric analysis of an example of a Porphyrin COF.
Figure 68:
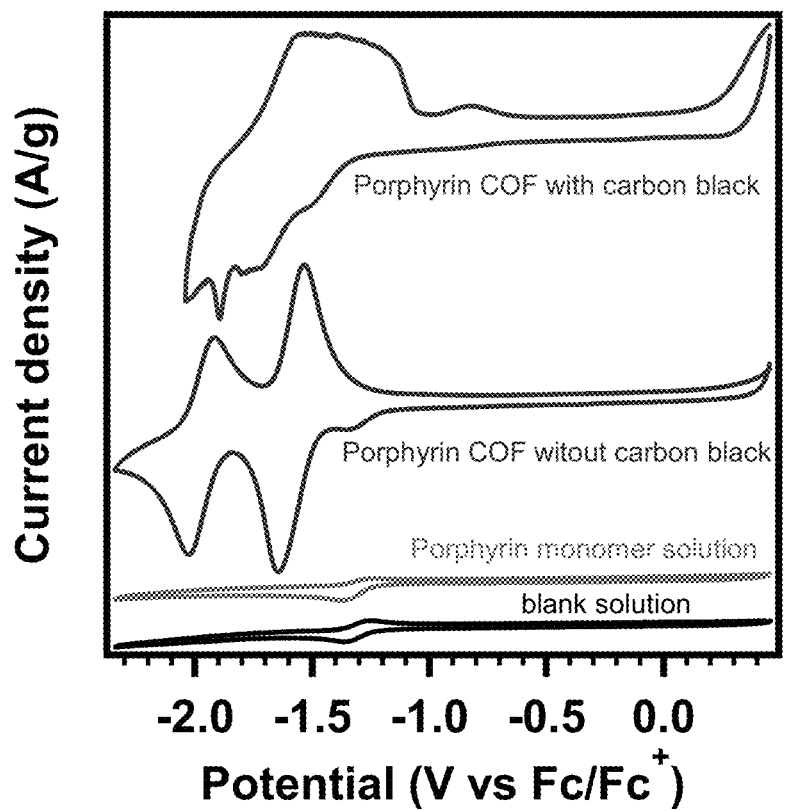
FIG. 68. Cyclic voltammograms (50 mV s$^{-1}$, 0.1 M TBAPF$_6$ in MeCN) of an example of a Porphyrin COF, tetra(vinylphenyl) porphyrin.

An alkene-linked porphyrin covalent organic framework (Porphyrin COF) was synthesized through an acyclic diene metathesis (ADMET) polymerization of a tetrafunctional porphyrin derivative (FIG. 61). Olefin metathesis was chosen for its high functional group tolerance, mild reaction conditions, benign stoichiometric byproducts (ethylene) and synthetically convenient monomers. The porphyrin was polymerized under solvothermal conditions in $CH_2Cl_2$ at 45° C. in the presence of 6 mol % of the Grubbs 2nd Generation olefin metathesis catalyst, which provided the conjugated porphyrin network (FIG. 1) as an insoluble microcrystalline powder. The porphyrin COF exhibited x-ray diffraction peaks consistent with a square, two-dimensional layered network (FIG. 62). The porphyrin network powders exhibited FT-IR spectra consistent with the formation of a network linked by stilbene moieties, whereas the porphyrin monomer exhibits bands corresponding to terminal alkene stretches and torsion peaks at 1627 $cm^{-1}$ and 982 $cm^{-1}$, respectively (FIG. 63). These peaks are attenuated in the Porphyrin COF powders, in which most of these moieties are transformed into stilbene linkages. Porphyrin COF powders were also characterized by solid-state 13C cross-polarization magic angle spinning (CP-MAS) NMR, which was also consistent with the expected stilbene-linked structure. The spectrum indicates aromatic and porphyrin resonances centered at 117, 123, 131, 138, and 150 ppm, as well as a peak corresponding to the vinylic carbons at 118 ppm (FIG. 64). The porphyrin COF powders prepared under these conditions exhibit permanent porosity, as indicated by their N2 uptake (FIG. 65), which corresponds to a BET surface area of 338 $m^2$/g, and a pore size distribution consistent with the expected structure (FIG. 66). They may be heated to 400° C. before decomposing to volatile products, as determined by thermogravimetric analysis (FIG. 67). Furthermore, the porphyrin COF powder exhibits electrochemical oxidation and reduction processes expected for porphyrin-containing materials when its powders are drop-cast onto electrodes (FIG. 68). These processes for the porphyrin COF show higher current density than solutions of the porphyrin monomer because the COF is interfaced directly to the electrode. This promising redox activity indicates that the porphyrin COF material is a candidate material for charge storage devices, such as electrochemical capacitors and batteries.

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

What is claimed is:

1. A cross-linked polymer network comprising a plurality of
monomers cross-linked as a polymer network via a plurality of vinylene and/or stilbene moieties, wherein at least one monomer of the plurality of monomers comprises a conjugated core and at least three polymerizable groups,
wherein each monomer of the plurality of monomers comprises one or more heterocycles, one or more quinones, one or more fused acenes, or any combination thereof in the core of the monomer; and,
wherein the at least one monomer is selected from porphyrins, carbazoles, thiophenes, pyridines, benzothiadiazoles, quinones, fused acenes, and combinations thereof.

2. The cross-linked polymer network of claim 1, wherein at least two of the plurality of monomers comprise a conjugated core and at least three polymerizable groups.

3. The cross-linked polymer network of claim 1, wherein each of the plurality of monomers comprises a conjugated core and at least three polymerizable groups.

4. A cross-linked polymer network comprising a plurality of monomers cross-linked as a polymer network via a plurality of vinylene and/or stilbene moieties, wherein at least one monomer of the plurality of monomers comprises a conjugated core and at least three polymerizable groups;
wherein each monomer of the plurality of monomers comprises one or more heterocycles, one or more quinones, one or more fused acenes, or any combination thereof in the core of the monomer; and,
wherein the plurality of monomers is selected from porphyrins, carbazoles, thiophenes, pyridines, benzothiadiazoles, quinones, fused acenes, and combinations thereof.

5. The cross-linked polymer network of claim 1, wherein the cross-linked polymer network is at least partially conjugated.

6. The cross-linked polymer network of claim 1, wherein the plurality of monomers are fully conjugated.

7. The cross-linked polymer network of claim 1, wherein cross-linked polymer network is a fully conjugated network.

8. The cross-linked polymer network of claim 1, wherein the polymerizable groups comprise an olefin group.

9. The cross-linked polymer network of claim 1, wherein the cross-linked polymer network comprises an arylene vinylene-linked polymer network.

10. The cross-linked polymer network of claim 1, wherein the vinylene or stilbene moieties are formed via olefin metathesis reactions.

11. The cross-linked polymer network of claim 1, wherein the vinylene or stilbene moieties are formed via polymerization using an olefin metathesis catalyst.

12. The cross-linked polymer network of claim 1, wherein the cross-linked polymer network are formed via polymerization comprising a monomer having at least three polymerizable groups, and wherein the polymerization has a degree of reaction within a range of 33% to 100%.

13. The cross-linked polymer network of claim 1, wherein the cross-linked polymer network is covalently bonded to a substrate via a linker group.

14. The cross-linked polymer network of claim 13, wherein the linker group comprises one or more alkyl moieties and one or more of a 5 or 6 member aromatic ring moiety.

15. The cross-linked polymer network of claim 1, further comprising an analyte in contact with the cross-linked polymer network, wherein the analyte is configured to change the fluorescence of the cross-linked polymer network.

16. A cross-linked polymer network comprising
a plurality of monomers cross-linked as a polymer network via a plurality of vinylene and/or stilbene moieties, wherein at least one monomer of the plurality of monomers comprises a conjugated core and at least three polymerizable groups; and
an analyte in contact with the cross-linked polymer network, wherein the analyte is configured to change the fluorescence of the cross-linked polymer network;
wherein the analyte comprises an explosive, an explosive degradation product, or an explosive taggant; and,
wherein the explosive is a nitramine or a nitroester.

17. The cross-linked polymer network of claim 16, wherein the nitramine is cyclotrimethylenetrinitramine or the nitroester is pentaerythritol tetranitrate (PETN), trinitrotoluene (TNT), dinitrotoluene (DNT), 2,4,6-triamino-1,3,5-trinitrobenzene (TATB), 2,3-dimethyl-2,3-dinitrobutane (DMNB)), or octahydro-1,3,5,7-tetranitro-1,3,5,7-tetrazocine (HMX).

18. The cross-linked polymer network of claim 16, wherein at least two of the plurality of monomers comprise a conjugated core and at least three polymerizable groups.

19. The cross-linked polymer network of claim 16, wherein each of the plurality of monomers comprises a conjugated core and at least three polymerizable groups.

20. The cross-linked polymer network of claim 16, wherein the cross-linked polymer network is at least partially conjugated.

21. The cross-linked polymer network of claim 16, wherein the plurality of monomers are fully conjugated.

22. The cross-linked polymer network of claim 16, wherein the cross-linked polymer network is a fully conjugated network.

23. The cross-linked polymer network of claim 16, wherein the polymerizable groups comprise an olefin group.

24. The cross-linked polymer network of claim 16, wherein the cross-linked polymer network comprises an arylene vinylene-linked polymer network.

25. The cross-linked polymer network of claim 16, wherein the vinylene or stilbene moieties are formed via olefin metathesis reactions.

26. The cross-linked polymer network of claim 16, wherein the vinylene or stilbene moieties are formed via polymerization using an olefin metathesis catalyst.

27. The cross-linked polymer network of claim 16, wherein the cross-linked polymer network are formed via polymerization comprising a monomer having at least three polymerizable groups, and wherein the polymerization has a degree of reaction within a range of 33% to 100%.

28. The cross-linked polymer network of claim 16, wherein the cross-linked polymer network is covalently bonded to a substrate via a linker group.

29. The cross-linked polymer network of claim 28, wherein the linker group comprises one or more alkyl moieties and one or more of a 5 or 6 member aromatic ring moiety.

30. The cross-linked polymer network of claim 16, further comprising an analyte in contact with the cross-linked polymer network, wherein the analyte is configured to change the fluorescence of the cross-linked polymer network.

* * * * *